US007745694B1

(12) United States Patent
Knutzon et al.

(10) Patent No.: US 7,745,694 B1
(45) Date of Patent: **\*Jun. 29, 2010**

(54) METHODS AND COMPOSITIONS FOR SYNTHESIS OF LONG CHAIN POLYUNSATURATED FATTY ACIDS IN PLANTS

(75) Inventors: Deborah Knutzon, Granite Bay, CA (US); Pradip Mukerji, Gahanna, OH (US); Yung-Sheng Huang, Upper Arlington, OH (US); Jennifer Thurmond, Columbus, OH (US); Sunita Chaudhary, Pearland, TX (US); Amanda Eun-Yeong Leonard, Gahanna, OH (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/355,903

(22) PCT Filed: Apr. 10, 1998

(86) PCT No.: PCT/US98/07421

§ 371 (c)(1),
(2), (4) Date: Aug. 5, 1999

(87) PCT Pub. No.: WO98/46764

PCT Pub. Date: Oct. 22, 1998

Related U.S. Application Data

(63) Continuation-in-part of application No. 08/956,985, filed on Oct. 24, 1997, now Pat. No. 6,051,754, and a continuation-in-part of application No. 08/834,655, filed on Apr. 11, 1997, now Pat. No. 5,968,809, and a continuation-in-part of application No. 08/833,610, filed on Apr. 11, 1997, now Pat. No. 5,972,664, and a continuation-in-part of application No. 08/834,033, filed on Apr. 11, 1997, now Pat. No. 6,075,183.

(51) Int. Cl.
*A01H 5/00* (2006.01)
*C12N 15/82* (2006.01)

(52) U.S. Cl. ........................ 800/281; 800/298

(58) Field of Classification Search ............... 435/189, 435/135, 410, 320.1; 514/549, 560, 552; 800/298; 536/23.1, 23.2
See application file for complete search history.

(56) References Cited

U.S. PATENT DOCUMENTS

| 3,649,295 | A | 3/1972 | Bernhart | 99/57 |
| 4,058,594 | A | 11/1977 | Williams | 424/37 |
| 4,526,793 | A | 7/1985 | Ingenbleek et al. | 426/72 |
| 4,526,902 | A | 7/1985 | Rubin | 514/560 |
| 4,614,663 | A | 9/1986 | Rule | 426/601 |
| 4,670,285 | A | 6/1987 | Clandinin et al. | 426/602 |
| 4,843,095 | A | 6/1989 | Rubin | 514/558 |
| 4,920,098 | A | 4/1990 | Cotter et al. | 514/2 |
| 4,938,984 | A | 7/1990 | Traitler et al. | 426/580 |
| 5,057,419 | A | 10/1991 | Martin | |
| 5,374,657 | A | 12/1994 | Kyle | 514/547 |
| 5,376,541 | A | 12/1994 | Kawashima | |
| 5,407,957 | A | 4/1995 | Kyle et al. | 514/547 |
| 5,443,974 | A | 8/1995 | Hilz | |
| 5,492,938 | A | 2/1996 | Kyle et al. | 514/786 |
| 5,512,482 | A | 4/1996 | Voelker et al. | 435/320.1 |
| 5,545,553 | A | 8/1996 | Gotschlich | 435/252.33 |
| 5,550,156 | A | 8/1996 | Kyle | 514/547 |
| 5,552,306 | A | 9/1996 | Thomas | |
| 5,614,393 | A | 3/1997 | Thomas | |
| 5,614,400 | A | 3/1997 | Cahoon | |
| 5,663,068 | A | 9/1997 | Thomas | |
| 5,689,050 | A | 11/1997 | Thomas | |

(Continued)

FOREIGN PATENT DOCUMENTS

EP 550162 7/1993

(Continued)

OTHER PUBLICATIONS

Ackman, "*Problems in Fish Oils and Concentrates,*" Canadian Institute of Fisheries Technology, Technical University of Nova Scotia, 189-204.
Bajpai and Bajpai, "*Arachidonic Acid Production by Microorganisms,*" Biotechnology and Applied Biochemistry 15:1-10 (1992).
Gurr, "*Alpha or Gamma: What's a Double Bond Position Between Friends?" 1. Gamma-linolenic Acid,* Lipid Technology (Mar. 1995).
Hodgson, "*Advances in Vector Systems for Gene Therapy,*" Ex. Opin. Ther. Patents 5(5):459-468 (1995).
Horrobin, "*Medical Roles of Metabolites of Precursor EFA,*" INFORM 6(4):428-434 (Apr. 1995).
Murata at al., "*Biosynthesis of gamma-Linolenic Acid in the Cyanobacterium Spiruline platensis,*" In: gamma-Linolenic Acid Metabolism and Its Roles in Nutrition and Medicine (Huang and Mills, eds.), pp. 22-32, Access Press, Champain, IL.

(Continued)

*Primary Examiner*—Elizabeth F McElwain
(74) *Attorney, Agent, or Firm*—Armstrong Teasdale LLP

(57) ABSTRACT

The present invention relates to compositions and methods for preparing polyunsaturated long chain fatty acids in plants, plant parts and plant cells, such as leaves, roots, fruits and seeds. Nucleic acid sequences and constructs encoding fatty acid desaturases, including $\Delta5$-desaturases, $\Delta6$-desaturases and $\Delta12$-desaturases, are used to generate transgenic plants, plant parts and cells which contain and express one or more transgenes encoding one or more desaturases. Expression of the desaturases with different substrate specificities in the plant system permit the large scale production of polyunsaturated long chain fatty acids such as docosahexaenoic acid, eicosapentaenoic acid, $\alpha$-linolenic acid, gamma-linolenic acid, arachidonic acid and the like for modification of the fatty acid profile of plants, plant parts and tissues. Manipulation of the fatty acid profiles allows for the production of commercial quantities of novel plant oils and products.

61 Claims, 25 Drawing Sheets

U.S. PATENT DOCUMENTS

| | | | |
|---|---|---|---|
| 5,968,809 A | 10/1999 | Knutzon et al. | 435/254.2 |
| 5,972,664 A | 10/1999 | Knutzon et al. | 435/136 |
| 6,051,754 A | 4/2000 | Knutzon et al. | 800/281 |
| 6,075,183 A | 6/2000 | Knutzon et al. | 800/281 |
| 6,136,574 A | 10/2000 | Knutzon et al. | 435/134 |
| 6,355,861 B1 | 3/2002 | Thomas | |
| 6,459,018 B1 | 10/2002 | Knutzon | 800/281 |
| 6,683,232 B1 | 1/2004 | Thomas | |
| 7,189,894 B2 | 3/2007 | Thomas | |
| 5,789,220 A | 8/1998 | Thomas | |

FOREIGN PATENT DOCUMENTS

| | | |
|---|---|---|
| EP | 0561569 A2 | 9/1993 |
| EP | 644263 | 3/1995 |
| EP | 736598 | 1/1996 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 96/10086 | 4/1996 |
| WO | WO 96/13591 | 5/1996 |
| WO | WO 96/21022 | 7/1996 |
| WO | WO 96/21037 | 7/1996 |
| WO | WO 97/30582 | 8/1997 |

OTHER PUBLICATIONS

Ratledge, "*Single cell oils-have they a biotechnological future?*" MB Tech. 11 (Jul. 1995).

Reddy and Thomas, "*Expression of a cyanobacterial $\Delta^6$-desaturase gene results in gamma-linolenic Acid Production in Transgenic Plants*," Nature Biotechnology 14:639-642 (May 1996).

Ward, "*Microbial Production of long-chain PUFAs*," INFORM 6(6):683-688 (Jun. 1995).

"*Closer to Mother's Milk*", the Gist 61:8-9 (Spring 1995).

"*Exciting Prospects for Stearidonic Acid Seed Oils*," Lipid Technology (Nov. 1996).

Takagi and Itabashi, "*cis-5-Olefinic Unusual Fatty Acids in Seed Lipids of Gymnospermae and Their Distribution in Triacygylycerols,*" Lipids 17(10):716-723(1982).

Wolff, "*New Tools to Explore Lipid Metabolism*," INFORM 8(1):116-119 (Jan. 1997).

"*Conifer Oils Offer Exciting Possibilities*," Lipid Technology (Jan. 1997).

PCT International Search Report.

L.V. Michaelson, et al., "Isolation of a $\Delta^5$-Fatty Acid Desaturase Gene from Mortierella alpina", Journal of Biological Chemistry, American Society of Biological Chemists, vol. 273, No. 30, Jul. 24, 1998, pp. 19055-19059 (XP-002076636).

Deborah S. Knutzon, et al., "Identification of $\Delta$5-Desaturase from Mortierella alpina by Heterologous Expression in Bakers' Yeast and Canola", Journal of Biological Chemistry, American Society of Biological Chemists, vol. 273, No. 45, Nov. 6, 1998, pp. 29360-29366 (XP-002106760).

Patrick S. Covello, et al., "Functional Expression of the Extraplastidial *Arabidopsis thaliana* Oleate Desaturase Gene (FAD2) in *Saccharamyces cerevisiae*", Plant Physiol., vol. 111, 1996, pp. 223-226 (XP-002075211).

U.S. Appl. No. 09/367,013, filed Apr. 10, 1998, Knutzon, et al.

Hill-Eubanks, et al.; "Structure of a G-Protein-Coupling domain of a Muscarinic Receptor Predicted by Random Saturation Mutagenesis"; The Journal of Biological Chemistry; vol. 271, No. 6, Feb. 9, 1996, pp. 3058-3065; The American Society for Biochemistry and Molecular Biology, Inc.

Shibuya, et al.; "Purification, Characterization, and cDNA Cloning of a Novel a-Galactosidase from *Mortierella vinacea*"; Biosci. Biotech. Biochem., vol. 61, No. 4, 1997; pp. 592-598.

Sambrook, et al.; "Molecular Cloning—A laboratory Manual, Second Edition"; Cold Spring Harbor Laboratory Press, 1989; pp. 8.46-8.49, 9.47-9.57 and 2.114-2.117.

U.S. Appl. No. 11/445,506 and enclosed prosecution history.

FIG. 3A

```
CGACACTCCT TCCTTCTTCT CACCCGTCCT AGTCCCCTTC AACCCCCCTC TTTGACAAAG   60
                                                                    *
ACAACAAACC ATG GCT GCT GCT CCC AGT GTG AGG ACG TTT ACT CGG GCC GAG
        Met Ala Ala Ala Pro Ser Val Arg Thr Phe Thr Arg Ala Glu
    120
     *
GTT TTG AAT GCC GAG GCT CTG AAT GAG GGC AAG AAG GAT GCC GAG GCA
Val Leu Asn Ala Glu Ala Leu Asn Glu Gly Lys Lys Asp Ala Glu Ala
                        180
                         *
CCC TTC TTG ATG ATC ATC GAC AAC AAG GTG TAC GAT GTC CGC GAG TTC
Pro Phe Leu Met Ile Ile Asp Asn Lys Val Tyr Asp Val Arg Glu Phe

GTC CCT GAT CAT CCC GGT GGA AGT GTG ATT CTC ACG CAC GTT GGC GAG
Val Pro Asp His Pro Gly Gly Ser Val Ile Leu Thr His Val Gly Glu
                240                                         300
                 *                                           *
GAC GTT ATG ACT GAC GTC TTT GAC ACT TTT CAC CCC GAG GCT GCT TGG GAG
Asp Val Met Thr Asp Val Phe Asp Thr Phe His Pro Glu Ala Ala Trp Glu

ACT CTT GCC AAC TTT TAC GTT GGT GAT ATT GAC GAG AGC GAC CGC GAT
Thr Leu Ala Asn Phe Tyr Val Gly Asp Ile Asp Glu Ser Asp Arg Asp
 360
  *
ATC AAG AAT GAT GAC TTT GCG GCC GAG GTC CGC AAG CTG CGT ACC TTG
Ile Lys Asn Asp Asp Phe Ala Ala Glu Val Arg Lys Leu Arg Thr Leu
```

```
                                                                                              840
                                                                                               *
CCC  GAC  ATT  GAC  ACC  CAC  CCT  CTG  TTG  ACC  TGG  AGT  GAG  CAT  GCG  TTG
Pro  Asp  Ile  Asp  Thr  His  Pro  Leu  Leu  Thr  Trp  Ser  Glu  His  Ala  Leu

GAG  ATG  TTC  TCG  GAT  GTC  CCA  GAT  GAG  GAG  CTG  ACC  CGC  ATG  TGG  TCG
Glu  Met  Phe  Ser  Asp  Val  Pro  Asp  Glu  Glu  Leu  Thr  Arg  Met  Trp  Ser

900
                                          *
CGT  TTC  ATG  GTC  CTG  AAC  CAG  ACC  TGG  TTT  TAC  TTC  CCC  ATT  CTC  TCG
Arg  Phe  Met  Val  Leu  Asn  Gln  Thr  Trp  Phe  Tyr  Phe  Pro  Ile  Leu  Ser

960
                                                                 *
TTT  GCC  CGT  CTC  TCC  TGC  TGG  CTC  CAG  ATT  CTC  TTT  GTG  CTG  CCT
Phe  Ala  Arg  Leu  Ser  Cys  Trp  Leu  Gln  Ile  Leu  Phe  Val  Leu  Pro

AAC  GGT  CAG  GCC  CAC  AAG  CCC  GCC  TCG  GGC  CGT  GTG  CCC  GTG  CTG  TTG
Asn  Gly  Gln  Ala  His  Lys  Pro  Ala  Ser  Gly  Arg  Val  Pro  Val  Leu  Leu

1020
                                                                        *
GTC  GAG  CAG  CTG  CTT  GCG  ATG  CCC  GTC  AAC  TGG  ACC  ATG  ATC  TCG  ACC
Val  Glu  Gln  Leu  Leu  Ala  Met  Pro  Val  Asn  Trp  Thr  Met  Ile  Ser  Thr

ATG  TTC  CTG  TTC  ATC  AAG  GAT  CCC  GTC  CAC  ATG  TGG  TAC  CTC  TTT  TTG
Met  Phe  Leu  Phe  Ile  Lys  Asp  Pro  Val  His  Met  Trp  Tyr  Leu  Phe  Leu

1080
                         *
GTG  TCG  CAG  GCG  GTG  TGC  GGA  AAC  TTG  TTG  GCG  ATC  GTG  TTC  TCG  CTC
Val  Ser  Gln  Ala  Val  Cys  Gly  Asn  Leu  Leu  Ala  Ile  Val  Phe  Ser  Leu
```

```
AAC CAC AAC GGT ATG CCT ATC GTG AAG GAG GCG GTC GAT ATG
Asn His Asn Gly Met Pro Ile Val Lys Glu Ala Val Asp Met
                        1140                1200
GAT TTC TTC ACG AAG CAG ATC ATC ACG GGT CGT GAT GTC CAC CCG GGT
Asp Phe Phe Thr Lys Gln Ile Ile Thr Gly Arg Asp Val His Pro Gly
                                                        1260
CTA TTT GCC AAC TGG TTC ACG TTC GGA TTG AAC TAT CAG ATC GAG CAC
Leu Phe Ala Asn Trp Phe Thr Phe Gly Leu Asn Tyr Gln Ile Glu His
CAC TTG TTC CCT TCG ATG CCT AAA CAC AAC TTT TCA AAG ATC CAG CCT
His Leu Phe Pro Ser Met Pro Lys His Asn Phe Ser Lys Ile Gln Pro
        1320
GCT GTC GAG ACC CTG TGC AAA AAG TAC AAT GTC CGA TAC CAC ACC ACC
Ala Val Glu Thr Leu Cys Lys Lys Tyr Asn Val Arg Tyr His Thr Thr
                            1380
GGT ATG ATC GAG GGA ACT GCA GAG GTC TTT AGC CGT CTG AAC GAG GTC
Gly Met Ile Glu Gly Thr Ala Glu Val Phe Ser Arg Leu Asn Glu Val
TCC AAG GCT GCC TCC AAG ATG GGT AAG GCG CAG TAAAAAAAAA AAACAAGGAC
Ser Lys Ala Ala Ser Lys Met Gly Lys Ala Gln
                                        1440
```

FIG. 3D

```
GTTTTTTTC GCCAGTGCCT GTGCCTGTGC CTGCTTCCCT TGTCAAGTCG AGCGTTTCTG
                                    1500
GAAAGGATCG TTCAGTGCAG TATCATCATT CTCCTTTTAC CCCCGCTCA TATCTCATTC
                                    1560
ATTTCTCTTA TTAAACAACT TGTTCCCCCC TTCACCG
```

FIG. 3E

```
Ma524     EVRKLRTLFQSLGYYDSSKAYYAFKVSFNLCIWGLSTVIVAKWGQTSTLANVLSAALLGL  90
ATTS4723  ............................VTLY-TLAFVAAMSLGVLYGVLACPSVXPHQIAAGLLGL  38
12-5      ................................-GVLYGVLACTSVFAHQIAAALLGL  24
T42806    ..........GXX...............................................  4
W28140    ............................................................  1
W53753    .......................C....................................  1
R05219    ............................................................  2

Ma524     FWQQCGWLAHDFLHHQVFQDRFWGDL-FGAFLGGVC-QGFSSSWWKDKHNTHHAAPNVHGE  119
ATTS4723  GPNLQHIP....................................................  97
12-5      LWIIQSAYIGXDSGHYVIMSNKSNNX-FAQLLSGNCLTGI-IAWWKWTHNAHHLACNSLDY  97
T42806    LWIIQSAYIGHDSGHYVIMSNKSYNR-FAQLLSGNCLTGISIAWWKWTHNAHHLACNSLDY  83
W28140    ............................................................  4
W53753    ............................................................  1
R05219    ............................................................  2
                                                                            1

Ma524     DPDIDTHPLLTWSEHALEMFSDVPDEELTRMWS----RFMVLNQTWFYFPILSFARLSW  174
ATTS4723  GPNLQHIP..................................................  105
12-5      DPDLQHIPVFAVSTK---FFSSLTSRFYDRKLTFGPVARFLVSYQHFTYYPVMCFGRINL  140
T42806    ..........................................................  4
W28140    ..........................................................  1
W53753    ..........................................................  1
R05219    ..........................................................  2
```

```
GTCCCCTGTC GCTGTCGGCA CACCCCATCC TCCCTCGCTC CCTCTGCGTT TGTCCTTGGC   60
                                                                    *
CCACCGTCTC TCCTCCACCC TCCGAGACGA CTGCAACTGT AATCAGGAAC CGACAAATAC  120
                                                                    *
ACGATTTCTT TTTACTCAGC ACCAACTCAA AATCCTCAAC CGCAACCCTT TTTCAGG ATG  180
                                                                    Met

GCA CCT CCC AAC ACT ATC GAT GCC GGT TTG ACC CAG CGT CAT ATC AGC
Ala Pro Pro Asn Thr Ile Asp Ala Gly Leu Thr Gln Arg His Ile Ser
                                  240*

ACC TCG GCC CCA AAC TCG GCC AAG CCT GCC TTC GAG CGC AAC TAC CAG
Thr Ser Ala Pro Asn Ser Ala Lys Pro Ala Phe Glu Arg Asn Tyr Gln
                              300*

CTC CCC GAG TTC ACC ATC AAG GAG ATC CGA GGT CTC TGC ATC CCT GCC
Leu Pro Glu Phe Thr Ile Lys Glu Ile Arg Gly Leu Cys Ile Pro Ala

CAC
His
360*

TGC TTT GAG CGC TCC GGT CTC TTG GGT CTC CGT GGT CTC TTC CTG GCT GCC
Cys Phe Glu Arg Ser Gly Leu Leu Gly Leu Arg Gly Leu Phe Leu Ala Ala

GTT GCC ATC GAT
Val Ala Ile Asp
         420*

CTG ACT TGG GCG TCG CTC TTG GGC GCG ACC CAG ATC GAC AAG
Leu Thr Trp Ala Ser Leu Leu Gly Ala Thr Gln Ile Asp Lys

TTT GAG AAT CCC TTG ATC CGC TAT TTG TAT CGC CCT GTT TAC TGG ATC
Phe Glu Asn Pro Leu Ile Arg Tyr Leu Tyr Arg Pro Val Tyr Trp Ile
```

FIG. 5B

```
ATG CAG GGT ATT GTC TGC ACC GGT GTC TGG GTG CTG GCT CAC GAG TGT
Met Gln Gly Ile Val Cys Thr Gly Val Trp Val Leu Ala His Glu Cys
            480*                540*

GGT CAT CAG TCC TTC TCG ACC TCC AAG ACC CTC AAC AAC ACA GTT GGT
Gly His Gln Ser Phe Ser Thr Ser Lys Thr Leu Asn Asn Thr Val Gly
                                                600*

TGG ATC TTG CAC ATG TCG CTC TTG GTC CCC TAC CAC TCC TGG AGA ATC
Trp Ile Leu His Met Ser Leu Leu Val Pro Tyr His Ser Trp Arg Ile
                                                            660*

TCG CAC AAG TCC CAC AAG CTC GCC ACT CAT GGC ACC AAG GAC CAG GAG
Ser His Lys Ser His Lys Leu Ala Thr His Gly Thr Lys Asp Gln Glu

GTC TTT GTG CCC AAG ACC CGC TCC CAG GTT GGC TTG CCT CCC AAG GAG
Val Phe Val Pro Lys Thr Arg Ser Gln Val Gly Leu Pro Pro Lys Glu

AAC GCT GCT CCC GCT GTT ACC CAG GAG GAC ATG TCC GTG CAC CTG GAT
Asn Ala Ala Pro Ala Val Thr Gln Glu Asp Met Ser Val His Leu Asp
            720*

GAG GCT GCT CCC ATT GTG ACT TTG TTC ATG ATG GTG ATC CAG TTC TTG
Glu Ala Ala Pro Ile Val Thr Leu Phe Met Met Val Ile Gln Phe Leu
                        780*

TTC GGA TGG CCC GCG TAC CTG ATT ATG AAC GCC TCT GGC CAA GAC TAC
Phe Gly Trp Pro Ala Tyr Leu Ile Met Asn Ala Ser Gly Gln Asp Tyr
                                            840*
```

FIG. 5C

```
GGC CGC TGG ACC CAC TTC CAC ACG TAC TCG CCC ATC TTT GAG CCC
Gly Arg Trp Thr His Phe His Thr Tyr Ser Pro Ile Phe Glu Pro
                                                          900*

CGC AAC TTT TTC GAC ATT ATT TCG GAC TAC TCG GTG TTG GCT GCC
Arg Asn Phe Phe Asp Ile Ile Ser Asp Tyr Ser Val Leu Ala Ala
              960*

CTC GGT GCC CTG ATC TAT GCC TCC ATG TCG GGT CTC TTG ACC GTG
Leu Gly Ala Leu Ile Tyr Ala Ser Met Ser Gly Leu Leu Thr Val
                           1020*

ACC AAG TAC TAT ATT GTC CCC TAC ATG CAG TTG TCG CTC TTG GTC
Thr Lys Tyr Tyr Ile Val Pro Tyr Met Gln Leu Ser Leu Leu Val

CTG ATC TTC TTC TTG CAG CAC CTC TTT AAC GTC TTG TGG TAC GTC
Leu Ile Phe Phe Leu Gln His Leu Phe Asn Val Leu Trp Tyr Val
                                       1080*

GAG GGT GCC TGG AAT TTC CAG GAT CCC GCT GGA CGT ATG TTC CCC
Glu Gly Ala Trp Asn Phe Gln Asp Pro Ala Gly Arg Met Phe Pro

TCG ATC AAG TGG AAG TTC GAC TTG CAC ATT TTC TAC CAC CGC CAC
Ser Ile Lys Trp Lys Phe Asp Leu His Ile Phe Tyr His Arg His
                                                      1140*

CAT TTT GGC TTG TTC TCG CAA ATG CCG GGC ATT GTC CAC ACC GCT
His Phe Gly Leu Phe Ser Gln Met Pro Gly Ile Val His Thr Ala

CAT GTG GCC CAT CAC TTG TTC TCG CAA ATG CCG GGC TTC TAC CAT
His Val Ala His His Leu Phe Ser Gln Met Pro Gly Phe Tyr His
     1200*
```

```
GAA GCT ACC TAT CAT CTC AAG AAA CTG GGA GAG TAC TAT GTG TAC
Glu Ala Thr Tyr His Leu Lys Lys Leu Gly Glu Tyr Tyr Val Tyr
                        1260
                          *
                                                    1320
                                                      *
GAC CCA TCC CCG ATC GTC GTT GCG GTC TGG AGG TCG TTC CGT GAG TGC
Asp Pro Ser Pro Ile Val Val Ala Val Trp Arg Ser Phe Arg Glu Cys
                                                    1380
                                                      *
CGA TTC GTG GAG GAT CAG GGA GAC GTG GTC TTT TTC AAG AAG TAAAAA
Arg Phe Val Glu Asp Gln Gly Asp Val Val Phe Phe Lys Lys Lys
                                                                  1440
                                                                    *
AAAAGACAAT GGACCACACA CAACCTTGTC TCTACAGACC TACGTATCAT GTAGCCATAC

CACTTCATAA AAGAACATGA GCTCTAGAGG CGTGTCATTC GCGCCTCC
```

FIG. 5D

```
         10          20          30          40          50          60
                                                                      *
LHHTYTNIAG  ADPDVSTSEP  DVRRIKPNQK  WFVNHINQHM  FVPFLYGLLA  FKVRIQDINI
         70          80          90         100         110         120
                                                                      *
LYFVKTNDAI  RVNPISTWHT  VMFWGGKAFF  VWYRLIVPLQ  YLPLGKVLLL  FTVADMVSSY
        130         140         150         160         170         180
                                                                      *
WLALTFQANY  VVEEVQWPLP  DENGIIQKDW  AAMQVETTQD  YAHDSHLWTS  ITGSLNYQXV

HHLFPH
```

FIG. 6

GCTTCCTCCA GTTCATCCTC CATTTCGCCA CCTGCATTCT TTACGACCGT TAAGCAAG

```
ATG  GGA  ACG  GAC  CAA  GGA  AAA  ACC  TTC  ACC  TGG  GAA  GAG  CTG  GCG  GCC
met  Gly  Thr  Asp  Gln  Gly  Lys  Thr  Phe  Thr  Trp  Glu  Glu  Leu  Ala  Ala
 *
 60                                                120
                                                    *

CAT  AAC  ACC  AAG  GAC  CTA  CTC  TTG  GCC  ATC  CGC  GGC  AGG  GTG  TAC
His  Asn  Thr  Lys  Asp  Leu  Leu  Leu  Ala  Ile  Arg  Gly  Arg  Val  Tyr

GAT  GTC  ACA  AAG  TTC  TTG  AGC  CGC  CAT  CCT  GGT  GGA  GTG  GAC  ACT  CTC
Asp  Val  Thr  Lys  Phe  Leu  Ser  Arg  His  Pro  Gly  Gly  Val  Asp  Thr  Leu
                                         *
                                        180                                240
                                                                            *

CTC  GGA  GCT  GGC  CGA  GAT  GTT  ACT  ATT  ATG  AAG  AAG  TAC  TAT  GAG  CAC
Leu  Gly  Ala  Gly  Arg  Asp  Val  Thr  Ile  Met  Lys  Lys  Tyr  Tyr  Glu  His

GCG  TTT  GGG  GCT  GCA  GAT  GCC  ATT  ATG  ATC  TTC  CCG  GAG  CCA  ACG  TTC  CAC
Ala  Phe  Gly  Ala  Ala  Asp  Ala  Ile  Met  Ile  Phe  Pro  Glu  Pro  Thr  Phe  His
 *
300

CTG  GTC  TCG  AAT  GAG  CTG  CCC  ATC  TTC  GAG  GGC  TAC  TTT  ACG  GAT  CGG  AAC  ATT
Leu  Val  Ser  Asn  Glu  Leu  Pro  Ile  Phe  Glu  Gly  Tyr  Phe  Thr  Asp  Arg  Asn  Ile
             *
            360

AAA  ACC  ATC  AAG  ACG  AGA  GTC
Lys  Thr  Ile  Lys  Thr  Arg  Val
```

FIG. 7A

```
GAT  CCC  AAG  AAT  AGA  CCA  GAG  ATC  TGG  GGA  CGA  TAC  GCT  CTT  ATC  TTT
Asp  Pro  Lys  Asn  Arg  Pro  Glu  Ile  Trp  Gly  Arg  Tyr  Ala  Leu  Ile  Phe
                                        420*                480*

GGA  TCC  TTG  ATC  GCT  TCC  TAC  TAC  CAG  CGA  TTT  GTG  CCT  TTC  GTT
Gly  Ser  Leu  Ile  Ala  Ser  Tyr  Tyr  Gln  Arg  Phe  Val  Pro  Phe  Val

GTC  GAA  CGC  ACA  TGG  CTT  CAG  GTG  CAG  CTC  GCA  ATC  ATG  GGA  TTT
Val  Glu  Arg  Thr  Trp  Leu  Gln  Val  Gln  Leu  Ala  Ile  Met  Gly  Phe
540*

GCG  TGC  GCA  CAA  GTC  GGA  CTC  AAC  TTT  GCA  GAT  TCT  CAC  TTT
Ala  Cys  Ala  Gln  Val  Gly  Leu  Asn  Phe  Ala  Asp  Ser  His  Phe
                         600*

TCA  GTG  ACC  CAC  AAC  CCC  ACT  GTC  CCT  CTT  CAT  GAT  GCC  ACG  CAC
Ser  Val  Thr  His  Asn  Pro  Thr  Val  Pro  Leu  His  Asp  Ala  Thr  His

GAC  TTT  TTC  AAC  GGA  GCA  TCG  TAC  TGG  AAG  ATT  CTG  GGA  TAC  CAA  CAT  ATG
Asp  Phe  Phe  Asn  Gly  Ala  Ser  Tyr  Trp  Lys  Ile  Leu  Gly  Tyr  Gln  His  Met
                                             660*

CTC  GGC  CAT  CAC  CCC  TAC  ACC  AAC  ATT  GCT  GGA  GCA  GAT  CCC  GAC  GTG
Leu  Gly  His  His  Pro  Tyr  Thr  Asn  Ile  Ala  Gly  Ala  Asp  Pro  Asp  Val
                                                            720*
```

```
Row 1 (780):  TCG ACG TCT GAG CCC GAT GTT CGT CTC ATC AAG CCC AAC CAA AAG TGG
              Ser Thr Ser Glu Pro Asp Val Arg Leu Ile Lys Pro Asn Gln Lys Trp
              *780

Row 2:        TTT GTC AAC CAC ATC AAC CAG CAC ATG TTT GTT CCT TTC CTG TAC GGA
              Phe Val Asn His Ile Asn Gln His Met Phe Val Pro Phe Leu Tyr Gly
                                           *840

Row 3:        CTG CTG GCG TTC AAG GTG CGC ATT CAC GAC ATT TTG TAC TTT
              Leu Leu Ala Phe Lys Val Arg Ile His Asp Ile Leu Tyr Phe

Row 4:        GTC AAG ACC AAT GAC GCT ATT CGT GCT GTC AAT CCC ATC TCG ACA TGG CAC
              Val Lys Thr Asn Asp Ala Ile Arg Ala Val Asn Pro Ile Ser Thr Trp His
                                                     *900

Row 5:        ACT GTG ATG TTC TGG CTG CAG TAT CCC AAG GGC GGC AAG CTG GCA TTC TAT CGC
              Thr Val Met Phe Trp Leu Gln Tyr Pro Lys Gly Gly Lys Leu Ala Phe Tyr Arg

Row 6:        ATT GTT ATG GTG TCG TAT CAG TGG GGG CCC CTG TAC TCT CTG GCG CTG GTG CTC CTG TTC
              Ile Val Met Val Ser Tyr Gln Trp Gly Pro Leu Tyr Ser Leu Ala Leu Val Leu Leu Phe
                                                                         *960

Row 7 (1020): ACG GTC GCG GAC ATG GTG TCG TAT TAC TGG TGG CTG GCG CTG ACC TTC CAG
              Thr Val Ala Asp Met Val Ser Tyr Tyr Trp Trp Leu Ala Leu Thr Phe Gln
              *1020
```

```
GCG AAC CAC GTT GTT GAG GAA GTT CAG TGG CCG TTG CCT GAC GAG AAC
Ala Asn His Val Val Glu Glu Val Gln Trp Pro Leu Pro Asp Glu Asn
            1080                        1140

GGG ATC ATC CAA AAG GAC TGG GCA GCT ATG CAG GTC GAG ACT ACG CAG
Gly Ile Ile Gln Lys Asp Trp Ala Ala Met Gln Val Glu Thr Thr Gln
                                                1200

GAT TAC GCA CAC GAT TCG CAC CTC TGG ACC ATC ACT GGC AGC TTG
Asp Tyr Ala His Asp Ser His Leu Trp Thr Ile Thr Gly Ser Leu

AAC TAC CAG GCT GTG CAC CAT CTG TTC CCC AAC ACC GTG CAG CAC CAT
Asn Tyr Gln Ala Val His His Leu Phe Pro Asn Thr Val Gln His His
1260

TAT CCC GAT ATT CTG GCC ATC AAG AAC ACC TGC AGC GAG TAC AAG
Tyr Pro Asp Ile Leu Ala Ile Lys Asn Thr Cys Ser Glu Tyr Lys
                    1320

GTT CCA TAC CTT GTC AAG GAT ACG TTT TGG CAA GCA TTT GCT TCA CAT
Val Pro Tyr Leu Val Lys Asp Thr Phe Trp Gln Ala Phe Ala Ser His
                                            1380

TTG GAG CAC TTG CGT GTT CTT GGA CTC CGT CCC AAG GAA GAG TAGA
Leu Glu His Leu Arg Val Leu Gly Leu Arg Pro Lys Glu Glu
                                        1440

AGAAAAAAAG CGCCGAATGA AGTATTGCCC CCTTTTCTC CAAGAATGGC AAAAGGAGAT

CAAGTGGACA TTCTCTATGA AGA
```

```
                 10                 20                 30                 40                 50                 60                 70
MA29      MGTDQG-KTFTW-------EELAAHNTKDDLLLAIRGRVYDVTKFLSRHPGGVDTLLLGAGRDVTPV    59
MA524     MAAAPSVRTFTRAEVLNAEALNEGKKDAEAP--FLMIIDNKVYDVREFVPDHPGGSVILTHV-GKDGTDV  67
BorD6     MA--------AQIKKYITSDELKNHDKPGDLWISIQGKAYDVSDWKDHPGGSFPLKSLAGQEVTDA    59
Sy6803D6  ML-TAE-RI-------                                                       7
Sp1D6     MTSTTS-KV-------                                                       8

80                 90                100                110                120                130                140
MA29      FEMYHAFGAADAIMKKYYVGTLVSNELPIFPEPTVFHKTIKTRVEGYFTDRNIDPKNRPEIWGRYALIFG   129
MA524     FDTFHP-EAAWETLANFYVGDIDESDRDL--KNDDFAAEV-RKLRTLFQSLGYYDSSKAYYAFKVSFNLC   133
BorD6     FVAFHP-ASTWKNLDKFFTGYYL---KDY-SVSEVSKDY-RKLVFEFSKMGLYDKK---GHIMFATLC    118
Sy6803D6        KFTQKRGFRRVLNQRVDAYFAEHGLTQRDNPSMYLKTLIVL                        49
Sp1D6           TFGKSIGFRKELNRRVNAYLEAENISPRDNPPMYLKTAILLA                       50

150                160                170                180                190                200                210
MA29      SLIASYYAQLFVPFVVERTWLQVVFAIIMGFACAQVGLNPLHDASHFSVTHNPTVWKILGATHDFFNGAS   199
MA524     IWGL--STVIVAKWGQTSLANVLSAALLGLFWQQCGW-LAHDFLHHQVFQDRFWGDLFGAFLGGVCQGF   200
BorD6     FIAMLFAMSVYGVLFCEGVLVHLFSGCLMGFLWIQSGW-IGHDAGHYMVVSDSRLNKFMGIFAANCLSGI   187
Sy6803D6  WLFSAW---AFVLFAPVIFPVRLLGCMVLAIALAAFSFNVGHDANHNAYSSINPHINRVLGMTYDFVGLS   116
Sp1D6     WVVSAW---TFVVFGPDVLMMKLLGCIVLGFGVSAVGFNISHDGNHGGYSKYQWVNYLSGILTHDAIGVSS  117
```

```
MA29      YLVWMYQ-HMLGHHPYTNIAGADPDVST------SEPDVRRIKPN--QKWFVNHINQHMFV----PFLYG  256
MA524     SSSWWKDKHNT-HHAAPNVHGEDPDIDTHPLLTWSEHALEMFSDVP-DEELT-RMWSRFMVLNQTWFYFP  267
BorD6     SIGWWKWNHN-AHHIACNSLEYDPDLQYIPFLVVSSKFFGSLTSHFYEKRLTFDSLSRFFVISYQHWTFYP  256
Sy6803D6  FL-WRYR-HNYLHHTYTNILGHDVEIHG------D--GAVRMSPE--QEHVGIYRFQQFYI----WGLYL  170
Sp1D6     YL-WKFR-HNVLHHTYTNILGHDVEIHG------D--ELVRMSPS---MEYRWYHRYQHWFI----WFVYP  171

MA29      LLAF---KVRIQDINILYFVKTNDAIRVNPISTWHTVMFWGGKAFFVWYRLIVPLOY-LPLGKVLLLFTV  322
MA524     ICFARLSWCLQSILFVLPNGQAHKPSGARVP--ISLVEQLSLAMHWTWY-LATMFLFIKDPVNMLVYFLV  335
BorD6     IMSAARLNMYVQSLIMLLTK------RNVS-YRAQELLGCLVFSIWY--PLLVSCLPNWGERIMFVIA  315
Sy6803D6  FIPF---YWFLYDVYLVLNKGKYHDHKIPPFQPLELASLLGIKLLWLGYVFGLIIPIAVGYSPLEAVIGASI  237
Sp1D6     FIPY---YWS-IADVQTMLFKRQYHDHEIPSPTWDIATLLAFKAFGVAVFLIIPIAVGYSPLEAVIGASI  238

MA29      ADMVSSYWLALTFQANHVVEEVQWPLPDE-NGIIQKDWAAMQVETTQDYAHDSHLWTSITGSLNYQAVHH  391
MA524     SQAVCGNLLAIVFISLNHNGMPVI-----SKEEAVDMDFFTKQIITGRDVHPG-LFANWFTGGLNYQIEHH  399
BorD6     SLSVTG-MQQVQFSLNHFSSSVIY-----V-GKPKGNNWFEKQTDGTLDISCP-PWMDWFHGGLQFQIEHH  377
Sy6803D6  TYMTYGIVVCTIFMLAHVLESTEFLTPDGESGAIDDEWAICQIRTTANFATNNPFWNWFCGGLNHQVTHH  307
Sp1D6     VYMTHGLVACVVFMLAHVIIEPAEFLDPDNL--HIDDEWAIAQVKTTVDFAIPNNPIINWYVGGLNYQTVHH  306
```

FIG. 8B

```
         430            440            450            460            470            480            490
          |              |              |              |              |              |              |
MA29     LFPNVSQHHYPDILALIKNTCSEYKVPYLVKDTFWQAFASHLEHLRVLGLRPKE------------           446
MA524    LFPSMPRHNFSKIQPAVETLCKKYNVRYHT-TGMIEGTAEVFSRLNEVSKAASKMGKAQ                   457
BorD6    LFPKMPRCNLRKISPYVIELCKKHNLPYNY-ASFSKANEMTLRTLRNTALQARDITKPLPKNLVWEALHT         446
Sy6803D6 LFPNICHIHYPQLENIIKDVCQEFGVEYKVYPTFKAAIASNYRWLEAMGKAS                           359
Sp1D6    LFPHICHIHYPKIAPILAEVCEEFGVNYAVHQTFFGALAANYSWLKKMSINPET····KAIEQ                365
```

FIG. 8C

SCORES INIT1: 117  INITN: 225  OPT: 256
SMITH-WATERMAN SCORE: 408; 27.0% IDENTITY IN 441 aa OVERLAP

```
                     10         20         30        40         50
ma29gcg.pep  MGTDQGKT---FTWEELAAHNTKDDLLLAIRGRVYDVTKFLSRHPGGVDTLLLGAGRDVT
             : ::  :      ::   :   : : : :  :  : :::::::      :
253538a      QGPTPRYFTWDEVAQRSGCEERWLVIDRKVYNISEFTRRHPGGSRVISHYAGQDAT
                     10         20         30        40         50

60         70         80         90        100        110
ma29gcg.pep  PVFEMYHAF-GAADAIMKKYYYVGTLVSNELPIFPEPTVFHKTIKTRVEGYFTDRNIDPKN
              ::    :   :  ::::::   : :::    : ::: :::        :
253538a      DPFVAFHINKGLVKKYMNSLLIGEL-SPEQPSF-EPTKNKELTDEFRELRATVERMGLMK
                 60         70         80         90        100        110

120        130        140        150        160        170
ma29gcg.pep  RPEIWGRYALIFGSLIASYYAQLFVPFVVERTWLQVVF-AIIMGFACAQVGLNPLHDASH
              :  :   : :     :::::   ::: ::   : :    :    :
253538a      ANHVF--FLLYLLHILLLDGAAWLTLWFGTSFLPFLLCAVLLSAVQAQAGWLQ-HDYGH
                120        130        140        150        160        170

180        190        200        210        220
ma29gcg.pep  FSVTHNPTVWKILGATHDF----FNGASYLVWMYQHMLGHHPYTNIAGADPDVSTSE---
              : : :: ::   :   :    :  :     : :   :     :
253538a      LSVYRKPK-WNHL--VHKFVIGHLKGASANWNHRH-FQHHAKPNIFHKDPDVNMLHVFV
                180        190        200        210        220
```

FIG. 9A

SCORES INIT1: 117  INITN: 225  OPT: 256
SMITH-WATERMAN SCORE: 408;  27.0% IDENTITY IN 441 aa OVERLAP

```
                    230       240       250       260       270       280
ma29gcg.pep    ----PDVRRIKPNQKWF-VNHINQHMFV--PFLYGLLAFKVRIQDINILYFVKTNDAIRV
                   : :  :  : :::   :  :::::    ::::  :  :::  :  :  :::::
253538a        LGEWQPIEYGKKKLKYLPYNHQHEYFFLIGPPLLIPMYFQYQI-----IMTMIVHKNWVDL
                    230       240       250       260           270

290       300       310       320       330       340
ma29gcg.pep    NPISTWHTVMFWGGKAFFVWYRLIVPLQYLPLGKVLLLFTVADMVSSYWLALTFQANHVV
                  :   :  :         ::    :: :::  :::::     :::   ::: : ::: :
253538a        ----AWAVSYYI---RFFITY---IPF-YGILG-ALLFLNFIRFLESHWFVWVTQMNHIV
                    280       290       300       310       320       330

350       360       370       380       390
ma29gcg.pep    EEVQWPLPDENGIIQKDWAAMQVETT----QDYAHDSHLWTSITGSLNYQAVHHLFPNVS
                  :     : :   ::::    ::: :    ::: ::::: :          :::::
253538a        MEI----DQEAY-RDWFSSQLTATCNVEQSFFND---WFS--GHLNFQIEHHLFPTMP
                    340       350       360             370

400       410       420       430       440
ma29gcg.pep    QHHYPDILAIIKNTCSEYKVPYLVKDTFWQAFASHLEHLRVLGLRPKEEX
                  :::   :  :     ::    ::::      :::::  :::::::
253538a        RHNLHKIAPLVKSLCAKHGIEYQEKPLLRALLDIIRSLKKSGKLWLDAYLHKX
                    390       400       410       420       430
```

FIG. 9B

```
SCORES   INIT1: 231   INITN: 499   OPT: 401
SMITH-WATERMAN SCORE: 620;  27.3% IDENTITY IN 455 aa OVERLAP 10        20        30        40        50
ma524gcg.pep  MAAAPSVRTFTRAEVLNAEALNEGKKDAEAPFLMIIDNKVYDVREFVPDHPGGSVILTH-
              : :::   ::   ::    ::        ::  :::::: :::  :::::::   ::
253538a              QGPTPRYFTWDEV------AQRSGCEERWLVIDRKVYNISEFTRRHPGGSRVISHY
                          10            20        30        40        50

60        70        80         90       100       110
ma524gcg.pep  VGKDGTDVFDTFHPEAAW--ETLANFYVGDIDE---SDRDIKNDDFAAEVRKLRTLFQSL
                : : ::: ::          :   :::  :     :::: :    :::::: :  :
253538a       AGQDATDPFVAFHINKGLVKKYMNSLLIGELSPEQPSFEPTKNKELTDEFRELRATVERM
               60        70        80        90       100       110

120       130       140       150       160       170
ma524gcg.pep  GYYDSSKAYYAFKVSFNLCIWGLSTVIVAKWGQTSTLANVLSAALLGLFWQQCGWLAHDF
               : :  ::  :: : :: : :: ::  :  :  : : :: :: :::::  :  ::  ::
253538a       GLMKANHVFFLLYLLHILLLDGAAWLTLWVFG-TSFLPFLLCAVLLSAVQAQAGWLQHDY
               120       130       140       150       160

180       190       200       210       220       230
ma524gcg.pep  LHHQVFQDRFWGDLFGAFLGGVCQGFSSSWWKDKHNTHHAAPNVHGEDPDIDTHPLLTWS
                :  :    ::::  :: :::     :::::   ::::::::: : :::   :: :
253538a       GHLSVYRKPKWNHLVHKFVIGHLKGASAMWNHRHFQHHAKPNIFHKDPDVN---ML--
                170       180       190       200       210       220
```

FIG. 10A

```
SCORES  INIT1: 231   INITN: 499   OPT: 401
SMITH-WATERMAN SCORE: 620;  27.3% IDENTITY IN 455 aa OVERLAP 240        250        260        270        280        290
ma524gcg.pep  EHALEMFSDVPDEELTRMWSRFMVLNQTWFYFPILS---FARLSWCLQSILFVLPNGQAH
              :::  ::    :  : : ::  :  ::: ::::::     ::: : ::: ::::: :  ::
2535538a      -HVF-VLGEWQPIEYGKKKLKYLPYNHQHEYFFLIGPPLLIPMYFQYQIIMTMI----VH
                 230        240        250        260        270

300        310        320        330        340        349
ma524gcg.pep  KPSGARVPISLVEQLSLAMHWTWYLATMFLFIK--DPVNMLVYFLVSQAVCGNLLAIVFS
              :           :  :    :    :   ::     :   :   :    :   ::
2535538a      K----NWVDLAWAVSYYIRFFITYIPFYGILGALLFLNFIRFLESHWFVWVTQ
                    280        290        300        310        320

350        360        370        380        390        400        409
ma524gcg.pep  LNHNGMPVISKEEAVDMDFFTKQIITGRDVHPGLFANWFTGGLNYQIEHHLFPSMPRHNF
              ::   ::: :::     :   ::: :::  :  :  ::    ::  ::::::::::::::
2535538a      MNHIVMEI--DQEAYR-DWFSSQLTATCNVEQSFFNDWFSGHLNFQIEHHLFPTMPRHNL
                    330        340        350        360        370        380

410        420        430        440        450
ma524gcg.pep  SKIQPAVETLCKKYNVRYHTTGMIEGTAEVFSRLNEVSKAASKMGKAQX
              ::  ::  ::::  :  :::::   :  :::::::::::::::::::::
2535538a      HKIAPLVKSLCAKHGIEYQEKPLLRALLDIIRSLKKSGKLWLDAYLHKX
                    390        400        410        420        430
```

FIG. 10B

SEQUENCE LISTING

```
<160> NUMBER OF SEQ ID NOS: 52

<210> SEQ ID NO 1
<211> LENGTH: 1617
<212> TYPE: DNA
<213> ORGANISM: Mortierella alpina
<220> FEATURE:
<221> NAME/KEY: misc_feature
<222> LOCATION: ()..()
<223> OTHER INFORMATION: Description of Combined DNA/RNA Molecule:
      Delta-6 Desaturase Nucleic Acid Sequence

<400> SEQUENCE: 1
```

-continued

```
cgacactcct tccttcttct cacccgtcct agtcccttc aaccccctc tttgacaaag      60
acaacaaacc atggctgctg ctcccagtgt gaggacgttt actcgggccg aggttttgaa    120
tgccgaggct ctgaatgagg gcaagaagga tgccgaggca cccttcttga tgatcatcga    180
caacaaggtg tacgatgtcc gcgagttcgt ccctgatcat cccggtggaa gtgtgattct    240
cacgcacgtt ggcaaggacg gcactgacgt ctttgacact tttcaccccg aggctgcttg    300
ggagactctt gccaacttt acgttggtga tattgacgag agcgaccgcg atatcaagaa    360
tgatgacttt gcggccgagg tccgcaagct gcgtaccttg ttccagtctc ttggttacta    420
cgattcttcc aaggcatact acgccttcaa ggtctcgttc aacctctgca tctggggttt    480
gtcgacggtc attgtggcca agtggggcca gacctcgacc ctcgccaacg tgctctcggc    540
tgcgcttttg ggtctgttct ggcagcagtg cggatggttg gctcacgact ttttgcatca    600
ccaggtcttc caggaccgtt tctggggtga tcttttcggc gccttcttgg gaggtgtctg    660
ccagggcttc tcgtcctcgt ggtggaagga caagcacaac actcaccacg ccgcccccaa    720
cgtccacggc gaggatcccg acattgacac ccaccctctg ttgacctgga gtgagcatgc    780
gttggagatg ttctcggatg tcccagatga ggagctgacc gcatgtggt cgcgtttcat    840
ggtcctgaac cagacctggt tttacttccc cattctctcg tttgcccgtc tctcctggtg    900
cctccagtcc attctctttg tgctgcctaa cggtcaggcc acaagccct cgggcgcgcg    960
tgtgcccatc tcgttggtcg agcagctgtc gcttgcgatg cactggacct ggtacctcgc   1020
caccatgttc ctgttcatca aggatcccgt caacatgctg gtgtacttt tggtgtcgca   1080
ggcggtgtgc ggaaacttgt tggcgatcgt gttctcgctc aaccacaacg gtatgcctgt   1140
gatctcgaag gaggaggcgg tcgatatgga ttccttcacg aagcagatca tcacgggtcg   1200
tgatgtccac ccgggtctat ttgccaactg gttcacgggt ggattgaact atcagatcga   1260
gcaccacttg ttcccttcga tgcctcgcca caacttttca aagatccagc tgctgtcga   1320
gaccctgtgc aaaaagtaca atgtccgata ccacaccacc ggtatgatcg agggaactgc   1380
agaggtcttt agccgtctga acgaggtctc caaggctgcc tccaagatgg gtaaggcgca   1440
gtaaaaaaaa aaacaaggac gtttttttc gccagtgcct gtgcctgtgc ctgcttccct   1500
tgtcaagtcg agcgtttctg gaaggatcg ttcagtgcag tatcatcatt ctccttttac   1560
ccccgctca tatctcattc atttctctta ttaaacaact tgttccccc ttcaccg       1617
```

<210> SEQ ID NO 2
<211> LENGTH: 457
<212> TYPE: PRT
<213> ORGANISM: Mortierella alpina

<400> SEQUENCE: 2

Met Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys

```
                    85                   90                  95
Asn Asp Asp Phe Ala Ala Glu Val Arg Lys Leu Arg Thr Leu Phe Gln
            100                 105                 110
Ser Leu Gly Tyr Tyr Asp Ser Ser Lys Ala Tyr Tyr Ala Phe Lys Val
            115                 120                 125
Ser Phe Asn Leu Cys Ile Trp Gly Leu Ser Thr Val Ile Val Ala Lys
            130                 135                 140
Trp Gly Gln Thr Ser Thr Leu Ala Asn Val Leu Ser Ala Ala Leu Leu
145                 150                 155                 160
Gly Leu Phe Trp Gln Gln Cys Gly Trp Leu Ala His Asp Phe Leu His
                165                 170                 175
His Gln Val Phe Gln Asp Arg Phe Trp Gly Asp Leu Phe Gly Ala Phe
            180                 185                 190
Leu Gly Gly Val Cys Gln Gly Phe Ser Ser Trp Trp Lys Asp Lys
            195                 200                 205
His Asn Thr His His Ala Ala Pro Asn Val His Gly Glu Asp Pro Asp
210                 215                 220
Ile Asp Thr His Pro Leu Leu Thr Trp Ser Glu His Ala Leu Glu Met
225                 230                 235                 240
Phe Ser Asp Val Pro Asp Glu Glu Leu Thr Arg Met Trp Ser Arg Phe
                245                 250                 255
Met Val Leu Asn Gln Thr Trp Phe Tyr Phe Pro Ile Leu Ser Phe Ala
            260                 265                 270
Arg Leu Ser Trp Cys Leu Gln Ser Ile Leu Phe Val Leu Pro Asn Gly
            275                 280                 285
Gln Ala His Lys Pro Ser Gly Ala Arg Val Pro Ile Ser Leu Val Glu
            290                 295                 300
Gln Leu Ser Leu Ala Met His Trp Thr Trp Tyr Leu Ala Thr Met Phe
305                 310                 315                 320
Leu Phe Ile Lys Asp Pro Val Asn Met Leu Val Tyr Phe Leu Val Ser
                325                 330                 335
Gln Ala Val Cys Gly Asn Leu Leu Ala Ile Val Phe Ser Leu Asn His
            340                 345                 350
Asn Gly Met Pro Val Ile Ser Lys Glu Glu Ala Val Asp Met Asp Phe
            355                 360                 365
Phe Thr Lys Gln Ile Ile Thr Gly Arg Asp Val His Pro Gly Leu Phe
            370                 375                 380
Ala Asn Trp Phe Thr Gly Gly Leu Asn Tyr Gln Ile Glu His His Leu
385                 390                 395                 400
Phe Pro Ser Met Pro Arg His Asn Phe Ser Lys Ile Gln Pro Ala Val
                405                 410                 415
Glu Thr Leu Cys Lys Lys Tyr Asn Val Arg Tyr His Thr Thr Gly Met
            420                 425                 430
Ile Glu Gly Thr Ala Glu Val Phe Ser Arg Leu Asn Glu Val Ser Lys
            435                 440                 445
Ala Ala Ser Lys Met Gly Lys Ala Gln
450                 455

<210> SEQ ID NO 3
<211> LENGTH: 1488
<212> TYPE: DNA
<213> ORGANISM: Mortierella alpina

<400> SEQUENCE: 3
```

```
gtccctgtc gctgtcggca cacccatcc tccctcgctc cctctgcgtt tgtccttggc    60
ccaccgtctc tcctccaccc tccgagacga ctgcaactgt aatcaggaac cgacaaatac   120
acgatttctt tttactcagc accaactcaa aatcctcaac cgcaacccct tttcaggatg   180
gcacctccca acactatcga tgccggtttg acccagcgtc atatcagcac ctcggcccca   240
aactcggcca gcctgccttt cgagcgcaac taccagctcc ccgagttcac catcaaggag   300
atccgagagt gcatccctgc ccactgcttt gagcgctccg gtctccgtgg tctctgccac   360
gttgccatcg atctgacttg ggcgtcgctc ttgttcctgg ctgcgaccca gatcgacaag   420
tttgagaatc ccttgatccg ctatttggcc tggcctgttt actggatcat gcagggtatt   480
gtctgcaccg gtgtctgggt gctggctcac gagtgtggtc atcagtcctt ctcgacctcc   540
aagaccctca caacacagt tggttggatc ttgcactcga tgctcttggt ccctaccac    600 tcctggagaa tctcgcactc gaagcaccac aaggccactg ccatatgac caaggaccag   660 gtctttgtgc ccaagacccg ctcccaggtt ggcttgcctc ccaaggagaa cgctgctgct   720
gccgttcagg aggaggacat gtccgtgcac ctggatgagg aggctcccat tgtgactttg   780
ttctggatgg tgatccagtt cttgttcgga tggcccgcgt acctgattat gaacgcctct   840
ggccaagact acggccgctg gacctcgcac ttccacacgt actcgcccat ctttgagccc   900
cgcaactttt tcgacattat tatctcggac ctcggtgtgt tggctgccct cggtgccctg   960
atctatgcct ccatgcagtt gtcgctcttg accgtcacca agtactatat tgtcccctac  1020
ctctttgtca acttttggtt ggtcctgatc accttcttgc agcacaccga tcccaagctg  1080
ccccattacc gcgagggtgc ctggaatttc cagcgtggag ctctttgcac cgttgaccgc  1140
tcgtttggca agttcttgga ccatatgttc cacggcattg tccacaccca tgtggcccat  1200
cacttgttct cgcaaatgcc gttctaccat gctgaggaag ctacctatca tctcaagaaa  1260
ctgctgggag agtactatgt gtacgaccca tccccgatcg tcgttgcggt ctggaggtcg  1320
ttccgtgagt gccgattcgt ggaggatcag ggagacgtgg tcttttttcaa gaagtaaaaa  1380 aaaagacaat ggaccacaca caaccttgtc tctacagacc tacgtatcat gtagccatac  1440
cacttcataa aagaacatga gctctagagg cgtgtcattc gcgcctcc              1488
```

<210> SEQ ID NO 4
<211> LENGTH: 399
<212> TYPE: PRT
<213> ORGANISM: Mortierella alpina

<400> SEQUENCE: 4

```
Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80

Lys Phe Glu Asn Pro Leu Ile Arg Tyr Leu Ala Trp Pro Val Tyr Trp
                85                  90                  95

Ile Met Gln Gly Ile Val Cys Thr Gly Val Trp Val Leu Ala His Glu
            100                 105                 110
```

-continued

```
Cys Gly His Gln Ser Phe Ser Thr Ser Lys Thr Leu Asn Asn Thr Val
        115                 120                 125
Gly Trp Ile Leu His Ser Met Leu Leu Val Pro Tyr His Ser Trp Arg
    130                 135                 140
Ile Ser His Ser Lys His His Lys Ala Thr Gly His Met Thr Lys Asp
145                 150                 155                 160
Gln Val Phe Val Pro Lys Thr Arg Ser Gln Val Gly Leu Pro Pro Lys
                165                 170                 175
Glu Asn Ala Ala Ala Ala Val Gln Glu Glu Asp Met Ser Val His Leu
            180                 185                 190
Asp Glu Glu Ala Pro Ile Val Thr Leu Phe Trp Met Val Ile Gln Phe
        195                 200                 205
Leu Phe Gly Trp Pro Ala Tyr Leu Ile Met Asn Ala Ser Gly Gln Asp
    210                 215                 220
Tyr Gly Arg Trp Thr Ser His Phe His Thr Tyr Ser Pro Ile Phe Glu
225                 230                 235                 240
Pro Arg Asn Phe Phe Asp Ile Ile Ile Ser Asp Leu Gly Val Leu Ala
                245                 250                 255
Ala Leu Gly Ala Leu Ile Tyr Ala Ser Met Gln Leu Ser Leu Leu Thr
            260                 265                 270
Val Thr Lys Tyr Tyr Ile Val Pro Tyr Leu Phe Val Asn Phe Trp Leu
        275                 280                 285
Val Leu Ile Thr Phe Leu Gln His Thr Asp Pro Lys Leu Pro His Tyr
    290                 295                 300
Arg Glu Gly Ala Trp Asn Phe Gln Arg Gly Ala Leu Cys Thr Val Asp
305                 310                 315                 320
Arg Ser Phe Gly Lys Phe Leu Asp His Met Phe His Gly Ile Val His
                325                 330                 335
Thr His Val Ala His His Leu Phe Ser Gln Met Pro Phe Tyr His Ala
            340                 345                 350
Glu Glu Ala Thr Tyr His Leu Lys Lys Leu Leu Gly Glu Tyr Tyr Val
        355                 360                 365
Tyr Asp Pro Ser Pro Ile Val Val Ala Val Trp Arg Ser Phe Arg Glu
    370                 375                 380
Cys Arg Phe Val Glu Asp Gln Gly Asp Val Val Phe Phe Lys Lys
385                 390                 395

<210> SEQ ID NO 5
<211> LENGTH: 1483
<212> TYPE: DNA
<213> ORGANISM: Mortierella alpina

<400> SEQUENCE: 5
gcttcctcca gttcatcctc catttcgcca cctgcattct ttacgaccgt taagcaagat      60
gggaacggac caaggaaaaa ccttcacctg gaagagctg gcggcccata acaccaagga     120
cgacctactc ttggccatcc gcggcagggt gtacgatgtc acaaagttct tgagccgcca     180
tcctggtgga gtggacactc tcctgctcgg agctggccga gatgttactc cggtctttga     240
gatgtatcac gcgtttgggg ctgcagatgc cattatgaag aagtactatg tcggtacact     300
ggtctcgaat gagctgccca tcttcccgga gccaacggtg ttccacaaaa ccatcaagac     360
gagagtcgag ggctactta cggatcggaa cattgatccc aagaatagac cagagatctg     420
gggacgatac gctcttatct ttggatcctt gatcgcttcc tactacgcgc agctctttgt     480
gcctttcgtt gtcgaacgca catggcttca ggtggtgttt gcaatcatca tgggatttgc     540
```

-continued

```
gtgcgcacaa gtcggactca accctcttca tgatgcgtct cacttttcag tgacccacaa      600
ccccactgtc tggaagattc tgggagccac gcacgacttt ttcaacggag catcgtacct      660
ggtgtggatg taccaacata tgctcggcca tcaccectac accaacattg ctggagcaga      720
tcccgacgtg tcgacgtctg agcccgatgt tcgtcgtatc aagcccaacc aaaagtggtt      780
tgtcaaccac atcaaccagc acatgtttgt tcctttcctg tacggactgc tggcgttcaa      840
ggtgcgcatt caggacatca acattttgta ctttgtcaag accaatgacg ctattcgtgt      900
caatcccatc tcgacatggc acactgtgat gttctgggc ggcaaggctt tctttgtctg       960
gtatcgcctg attgttcccc tgcagtatct gccoctgggc aaggtgctgc tcttgttcac     1020
ggtcgcggac atggtgtcgt cttactggct ggcgctgacc ttccaggcga accacgttgt     1080
tgaggaagtt cagtggccgt tgcctgacga gaacgggatc atccaaaagg actgggcagc     1140
tatgcaggtc gagactacgc aggattacgc acacgattcg cacctctgga ccagcatcac     1200
tggcagcttg aactaccagg ctgtgcacca tctgttcccc aacgtgtcgc agcaccatta     1260
tcccgatatt ctggccatca tcaagaacac ctgcagcgag tacaaggttc atacccttgt     1320
caaggatacg tttttggcaag catttgcttc acatttggag cacttgcgtg ttcttggact     1380
ccgtcccaag gaagagtaga agaaaaaaag cgccgaatga agtattgccc ccttttcctc     1440
caagaatggc aaaaggagat caagtggaca ttctctatga aga                        1483
```

<210> SEQ ID NO 6
<211> LENGTH: 446
<212> TYPE: PRT
<213> ORGANISM: Mortierella alpina

<400> SEQUENCE: 6

```
Met Gly Thr Asp Gln Gly Lys Thr Phe Thr Trp Glu Glu Leu Ala Ala
1               5                   10                  15

His Asn Thr Lys Asp Asp Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205
```

-continued

```
Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 7
<211> LENGTH: 355
<212> TYPE: PRT
<213> ORGANISM: Mortierella alpina

<400> SEQUENCE: 7

Glu Val Arg Lys Leu Arg Thr Leu Phe Gln Ser Leu Gly Tyr Tyr Asp
1               5                   10                  15

Ser Ser Lys Ala Tyr Tyr Ala Phe Lys Val Ser Phe Asn Leu Cys Ile
            20                  25                  30

Trp Gly Leu Ser Thr Val Ile Val Ala Lys Trp Gly Gln Thr Ser Thr
        35                  40                  45

Leu Ala Asn Val Leu Ser Ala Ala Leu Leu Gly Leu Phe Trp Gln Gln
    50                  55                  60

Cys Gly Trp Leu Ala His Asp Phe Leu His His Gln Val Phe Gln Asp
65                  70                  75                  80

Arg Phe Trp Gly Asp Leu Phe Gly Ala Phe Leu Gly Gly Val Cys Gln
                85                  90                  95

Gly Phe Ser Ser Trp Trp Lys Asp Lys His Asn Thr His His Ala
            100                 105                 110

Ala Pro Asn Val His Gly Glu Asp Pro Asp Ile Asp Thr His Pro Leu
        115                 120                 125

Leu Thr Trp Ser Glu His Ala Leu Glu Met Phe Ser Asp Val Pro Asp
```

```
                    130                 135                 140
Glu Glu Leu Thr Arg Met Trp Ser Arg Phe Met Val Leu Asn Gln Thr
145                 150                 155                 160

Trp Phe Tyr Phe Pro Ile Leu Ser Phe Ala Arg Leu Ser Trp Cys Leu
                165                 170                 175

Gln Ser Ile Leu Phe Val Leu Pro Asn Gly Gln Ala His Lys Pro Ser
                180                 185                 190

Gly Ala Arg Val Pro Ile Ser Leu Val Glu Gln Leu Ser Leu Ala Met
                195                 200                 205

His Trp Thr Trp Tyr Leu Ala Thr Met Phe Leu Phe Ile Lys Asp Pro
                210                 215                 220

Val Asn Met Leu Val Tyr Phe Leu Val Ser Gln Ala Val Cys Gly Asn
225                 230                 235                 240

Leu Leu Ala Ile Val Phe Ser Leu Asn His Asn Gly Met Pro Val Ile
                245                 250                 255

Ser Lys Glu Glu Ala Val Asp Met Asp Phe Phe Thr Lys Gln Ile Ile
                260                 265                 270

Thr Gly Arg Asp Val His Pro Gly Leu Phe Ala Asn Trp Phe Thr Gly
                275                 280                 285

Gly Leu Asn Tyr Gln Ile Glu His His Leu Phe Pro Ser Met Pro Arg
                290                 295                 300

His Asn Phe Ser Lys Ile Gln Pro Ala Val Glu Thr Leu Cys Lys Lys
305                 310                 315                 320

Tyr Asn Val Arg Tyr His Thr Thr Gly Met Ile Glu Gly Thr Ala Glu
                325                 330                 335

Val Phe Ser Arg Leu Asn Glu Val Ser Lys Ala Ala Ser Lys Met Gly
                340                 345                 350

Lys Ala Gln
        355

<210> SEQ ID NO 8
<211> LENGTH: 104
<212> TYPE: PRT
<213> ORGANISM: Arabidopsis thaliana
<220> FEATURE:
<221> NAME/KEY: UNSURE
<222> LOCATION: (1)..(104)
<223> OTHER INFORMATION: Amino acids 27, 48, and 63 uncertain of
      sequence

<400> SEQUENCE: 8

Val Thr Leu Tyr Thr Leu Ala Phe Val Ala Ala Asn Ser Leu Gly Val
1               5                   10                  15

Leu Tyr Gly Val Leu Ala Cys Pro Ser Val Xaa Pro His Gln Ile Ala
                20                  25                  30

Ala Gly Leu Leu Gly Leu Leu Trp Ile Gln Ser Ala Tyr Ile Gly Xaa
                35                  40                  45

Asp Ser Gly His Tyr Val Ile Met Ser Asn Lys Ser Asn Asn Xaa Phe
50                  55                  60

Ala Gln Leu Leu Ser Gly Asn Cys Leu Thr Gly Ile Ile Ala Trp Trp
65                  70                  75                  80

Lys Trp Thr His Asn Ala His His Leu Ala Cys Asn Ser Leu Asp Tyr
                85                  90                  95

Gly Pro Asn Leu Gln His Ile Pro
                100
```

```
<210> SEQ ID NO 9
<211> LENGTH: 252
<212> TYPE: PRT
<213> ORGANISM: Arabidopsis thaliana

<400> SEQUENCE: 9

Gly Val Leu Tyr Gly Val Leu Ala Cys Thr Ser Val Phe Ala His Gln
1               5                   10                  15

Ile Ala Ala Leu Leu Gly Leu Leu Trp Ile Gln Ser Ala Tyr Ile
            20                  25                  30

Gly His Asp Ser Gly His Tyr Val Ile Met Ser Asn Lys Ser Tyr Asn
            35                  40                  45

Arg Phe Ala Gln Leu Leu Ser Gly Asn Cys Leu Thr Gly Ile Ser Ile
        50                  55                  60

Ala Trp Trp Lys Trp Thr His Asn Ala His His Leu Ala Cys Asn Ser
65                  70                  75                  80

Leu Asp Tyr Asp Pro Asp Leu Gln His Ile Pro Val Phe Ala Val Ser
                85                  90                  95

Thr Lys Phe Phe Ser Ser Leu Thr Ser Arg Phe Tyr Asp Arg Lys Leu
            100                 105                 110

Thr Phe Gly Pro Val Ala Arg Phe Leu Val Ser Tyr Gln His Phe Thr
        115                 120                 125

Tyr Tyr Pro Val Asn Cys Phe Gly Arg Ile Asn Leu Phe Ile Gln Thr
    130                 135                 140

Phe Leu Leu Leu Phe Ser Lys Arg Glu Val Pro Asp Arg Ala Leu Asn
145                 150                 155                 160

Phe Ala Gly Ile Leu Val Phe Trp Thr Trp Phe Pro Leu Leu Val Ser
                165                 170                 175

Cys Leu Pro Asn Trp Pro Glu Arg Phe Phe Val Phe Thr Ser Phe
            180                 185                 190

Thr Val Thr Ala Leu Gln His Ile Gln Phe Thr Leu Asn His Phe Ala
        195                 200                 205

Ala Asp Val Tyr Val Gly Pro Pro Thr Gly Ser Asp Trp Phe Glu Lys
    210                 215                 220

Gln Ala Ala Gly Thr Ile Asp Ile Ser Cys Arg Ser Tyr Met Asp Trp
225                 230                 235                 240

Phe Phe Gly Gly Leu Gln Phe Gln Leu Glu His His
                245                 250

<210> SEQ ID NO 10
<211> LENGTH: 125
<212> TYPE: PRT
<213> ORGANISM: Arabidopsis thaliana
<220> FEATURE:
<221> NAME/KEY: UNSURE
<222> LOCATION: (1)..(125)
<223> OTHER INFORMATION: Amino acids 2, 3, 30, 121, and 125 uncertain of
      sequence

<400> SEQUENCE: 10

Gly Xaa Xaa Asn Phe Ala Gly Ile Leu Val Phe Trp Thr Trp Phe Pro
1               5                   10                  15

Leu Leu Val Ser Cys Leu Pro Asn Trp Pro Glu Arg Phe Xaa Phe Val
            20                  25                  30

Phe Thr Gly Phe Thr Val Thr Ala Leu Gln His Ile Gln Phe Thr Leu
        35                  40                  45

Asn His Phe Ala Ala Asp Val Tyr Val Gly Pro Pro Thr Gly Ser Asp
    50                  55                  60
```

```
Trp Phe Glu Lys Gln Ala Ala Gly Thr Ile Asp Ile Ser Cys Arg Ser
 65                  70                  75                  80

Tyr Met Asp Trp Phe Phe Cys Gly Leu Gln Phe Gln Leu Glu His His
                 85                  90                  95

Leu Phe Pro Arg Leu Pro Arg Cys His Leu Arg Lys Val Ser Pro Val
            100                 105                 110

Gly Gln Arg Gly Phe Gln Arg Lys Xaa Asn Leu Ser Xaa
            115                 120                 125

<210> SEQ ID NO 11
<211> LENGTH: 131
<212> TYPE: PRT
<213> ORGANISM: HUMAN
<220> FEATURE:
<221> NAME/KEY: UNSURE
<222> LOCATION: (1)..(131)
<223> OTHER INFORMATION: Amino acid 110 uncertain of sequence

<400> SEQUENCE: 11

Pro Ala Thr Glu Val Gly Gly Leu Ala Trp Met Ile Thr Phe Tyr Val
 1               5                  10                  15

Arg Phe Phe Leu Thr Tyr Val Pro Leu Gly Leu Lys Ala Phe Leu
                 20                  25                  30

Gly Leu Phe Phe Ile Val Arg Phe Leu Glu Ser Asn Trp Phe Val Trp
             35                  40                  45

Val Thr Gln Met Asn His Ile Pro Met His Ile Asp His Asp Arg Asn
 50                  55                  60

Met Asp Trp Val Ser Thr Gln Leu Gln Ala Thr Cys Asn Val His Lys
 65                  70                  75                  80

Ser Ala Phe Asn Asp Trp Phe Ser Gly His Leu Asn Phe Gln Ile Glu
                 85                  90                  95

His His Leu Phe Pro Thr Met Pro Arg His Asn Tyr His Xaa Val Ala
            100                 105                 110

Pro Leu Val Gln Ser Leu Cys Ala Lys His Gly Ile Glu Tyr Gln Ser
            115                 120                 125

Lys Pro Leu
    130

<210> SEQ ID NO 12
<211> LENGTH: 87
<212> TYPE: PRT
<213> ORGANISM: Caenorhabditis elegans

<400> SEQUENCE: 12

Cys Ser Pro Lys Ser Ser Pro Thr Arg Asn Met Thr Pro Ser Pro Phe
 1               5                  10                  15

Ile Asp Trp Leu Trp Gly Gly Leu Asn Tyr Gln Ile Glu His His Leu
                 20                  25                  30

Phe Pro Thr Met Pro Arg Cys Asn Leu Asn Arg Cys Met Lys Tyr Val
             35                  40                  45

Lys Glu Trp Cys Ala Glu Asn Asn Leu Pro Tyr Leu Val Asp Asp Tyr
 50                  55                  60

Phe Val Gly Tyr Asn Leu Asn Leu Gln Gln Leu Lys Asn Met Ala Glu
 65                  70                  75                  80

Leu Val Gln Ala Lys Ala Ala
                 85
```

```
<210> SEQ ID NO 13
<211> LENGTH: 143
<212> TYPE: PRT
<213> ORGANISM: MOUSE
<220> FEATURE:
<221> NAME/KEY: UNSURE
<222> LOCATION: (1)..(143)
<223> OTHER INFORMATION: Amino acid 125 uncertain of sequence

<400> SEQUENCE: 13

Arg His Glu Ala Ala Arg Gly Gly Thr Arg Leu Ala Tyr Met Leu Val
 1               5                  10                  15

Cys Met Gln Trp Thr Asp Leu Leu Trp Ala Ala Ser Phe Tyr Ser Arg
            20                  25                  30

Phe Phe Leu Ser Tyr Ser Pro Phe Tyr Gly Ala Thr Gly Thr Leu Leu
        35                  40                  45

Leu Phe Val Ala Val Arg Val Leu Glu Ser His Trp Phe Val Trp Ile
 50                  55                  60

Thr Gln Met Asn His Ile Pro Lys Glu Ile Gly His Glu Lys His Arg
65                  70                  75                  80

Asp Trp Ala Ser Ser Gln Leu Ala Ala Thr Cys Asn Val Glu Pro Ser
                85                  90                  95

Leu Phe Ile Asp Trp Phe Ser Gly His Leu Asn Phe Gln Ile Glu His
            100                 105                 110

His Leu Phe Pro Thr Met Thr Arg His Asn Tyr Arg Xaa Val Ala Pro
        115                 120                 125

Leu Val Lys Ala Phe Cys Ala Lys His Gly Leu His Tyr Glu Val
    130                 135                 140

<210> SEQ ID NO 14
<211> LENGTH: 186
<212> TYPE: PRT
<213> ORGANISM: Mortierella alpina
<220> FEATURE:
<221> NAME/KEY: UNSURE
<222> LOCATION: (1)..(186)
<223> OTHER INFORMATION: Amino acid 179 uncertain of sequence

<400> SEQUENCE: 14

Leu His His Thr Tyr Thr Asn Ile Ala Gly Ala Asp Pro Asp Val Ser
 1               5                  10                  15

Thr Ser Glu Pro Asp Val Arg Arg Ile Lys Pro Asn Gln Lys Trp Phe
            20                  25                  30

Val Asn His Ile Asn Gln His Met Phe Val Pro Phe Leu Tyr Gly Leu
        35                  40                  45

Leu Ala Phe Lys Val Arg Ile Gln Asp Ile Asn Ile Leu Tyr Phe Val
 50                  55                  60

Lys Thr Asn Asp Ala Ile Arg Val Asn Pro Ile Ser Thr Trp His Thr
65                  70                  75                  80

Val Met Phe Trp Gly Gly Lys Ala Phe Phe Val Trp Tyr Arg Leu Ile
                85                  90                  95

Val Pro Leu Gln Tyr Leu Pro Leu Gly Lys Val Leu Leu Leu Phe Thr
            100                 105                 110

Val Ala Asp Met Val Ser Ser Tyr Trp Leu Ala Leu Thr Phe Gln Ala
        115                 120                 125

Asn Tyr Val Val Glu Glu Val Gln Trp Pro Leu Pro Asp Glu Asn Gly
    130                 135                 140

Ile Ile Gln Lys Asp Trp Ala Ala Met Gln Val Glu Thr Thr Gln Asp
145                 150                 155                 160
```

```
Tyr Ala His Asp Ser His Leu Trp Thr Ser Ile Thr Gly Ser Leu Asn
            165                 170                 175

Tyr Gln Xaa Val His His Leu Phe Pro His
        180                 185

<210> SEQ ID NO 15
<211> LENGTH: 5
<212> TYPE: PRT
<213> ORGANISM: Unknown organism
<220> FEATURE:
<221> NAME/KEY: misc_feature
<222> LOCATION: ()..()
<223> OTHER INFORMATION: Description of Unknown Organism: Organism with
      gene encoding a membrane-bound desaturase
<221> NAME/KEY: UNSURE
<222> LOCATION: (1)..(5)
<223> OTHER INFORMATION: Amino acids in positions 2 and 3 vary in the
      histidine box

<400> SEQUENCE: 15

His Xaa Xaa His His
1               5

<210> SEQ ID NO 16
<211> LENGTH: 446
<212> TYPE: PRT
<213> ORGANISM: BORAGE

<400> SEQUENCE: 16

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Val Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240
```

```
Ser Leu Ser Arg Phe Phe Val Ser Tyr Gln His Trp Thr Phe Tyr Pro
            245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala Gln Glu Leu Leu Gly
            275                 280                 285

Cys Leu Val Phe Ser Ile Trp Tyr Pro Leu Leu Val Ser Cys Leu Pro
            290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
            325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
            355                 360                 365

Gly Leu Gln Phe Gln Ile Glu His His Leu Phe Pro Lys Met Pro Arg
            370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
            405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr
            435                 440                 445

<210> SEQ ID NO 17
<211> LENGTH: 359
<212> TYPE: PRT
<213> ORGANISM: Synechocystis sp.

<400> SEQUENCE: 17

Met Leu Thr Ala Glu Arg Ile Lys Phe Thr Gln Lys Arg Gly Phe Arg
1               5                   10                  15

Arg Val Leu Asn Gln Arg Val Asp Ala Tyr Phe Ala Glu His Gly Leu
            20                  25                  30

Thr Gln Arg Asp Asn Pro Ser Met Tyr Leu Lys Thr Leu Ile Ile Val
            35                  40                  45

Leu Trp Leu Phe Ser Ala Trp Ala Phe Val Leu Phe Ala Pro Val Ile
    50                  55                  60

Phe Pro Val Arg Leu Leu Gly Cys Met Val Leu Ala Ile Ala Leu Ala
65                  70                  75                  80

Ala Phe Ser Phe Asn Val Gly His Asp Ala Asn His Asn Ala Tyr Ser
            85                  90                  95

Ser Asn Pro His Ile Asn Arg Val Leu Gly Met Thr Tyr Asp Phe Val
            100                 105                 110

Gly Leu Ser Ser Phe Leu Trp Arg Tyr Arg His Asn Tyr Leu His His
            115                 120                 125

Thr Tyr Thr Asn Ile Leu Gly His Asp Val Glu Ile His Gly Asp Gly
            130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
```

```
                165                 170                 175
Phe Leu Tyr Asp Val Tyr Leu Val Leu Asn Lys Gly Lys Tyr His Asp
            180                 185                 190

His Lys Ile Pro Pro Phe Gln Pro Leu Glu Leu Ala Ser Leu Leu Gly
            195                 200                 205

Ile Lys Leu Leu Trp Leu Gly Tyr Val Phe Gly Pro Leu Ala Leu
            210                 215                 220

Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
            260                 265                 270

Asp Glu Trp Ala Ile Cys Gln Ile Arg Thr Thr Ala Asn Phe Ala Thr
            275                 280                 285

Asn Asn Pro Phe Trp Asn Trp Phe Cys Gly Gly Leu Asn His Gln Val
            290                 295                 300

Thr His His Leu Phe Pro Asn Ile Cys His Ile His Tyr Pro Gln Leu
305                 310                 315                 320

Glu Asn Ile Ile Lys Asp Val Cys Gln Glu Phe Gly Val Glu Tyr Lys
                325                 330                 335

Val Tyr Pro Thr Phe Lys Ala Ala Ile Ala Ser Asn Tyr Arg Trp Leu
            340                 345                 350

Glu Ala Met Gly Lys Ala Ser
            355

<210> SEQ ID NO 18
<211> LENGTH: 365
<212> TYPE: PRT
<213> ORGANISM: Spirulina sp.

<400> SEQUENCE: 18

Met Thr Ser Thr Thr Ser Lys Val Thr Phe Gly Lys Ser Ile Gly Phe
1               5                   10                  15

Arg Lys Glu Leu Asn Arg Arg Val Asn Ala Tyr Leu Glu Ala Glu Asn
            20                  25                  30

Ile Ser Pro Arg Asp Asn Pro Met Tyr Leu Lys Thr Ala Ile Ile
            35                  40                  45

Leu Ala Trp Val Val Ser Ala Trp Thr Phe Val Phe Gly Pro Asp
    50                  55                  60

Val Leu Trp Met Lys Leu Leu Gly Cys Ile Val Leu Gly Phe Gly Val
65                  70                  75                  80

Ser Ala Val Gly Phe Asn Ile Ser His Asp Gly Asn His Gly Gly Tyr
                85                  90                  95

Ser Lys Tyr Gln Trp Val Asn Tyr Leu Ser Gly Leu Thr His Asp Ala
            100                 105                 110

Ile Gly Val Ser Ser Tyr Leu Trp Lys Phe Arg His Asn Val Leu His
            115                 120                 125

His Thr Tyr Thr Asn Ile Leu Gly His Asp Val Glu Ile His Gly Asp
130                 135                 140

Glu Leu Val Arg Met Ser Pro Ser Met Glu Tyr Arg Trp Tyr His Arg
145                 150                 155                 160

Tyr Gln His Trp Phe Ile Trp Phe Val Tyr Pro Phe Ile Pro Tyr Tyr
                165                 170                 175
```

Trp Ser Ile Ala Asp Val Gln Thr Met Leu Phe Lys Arg Gln Tyr His
            180                 185                 190

Asp His Glu Ile Pro Ser Pro Thr Trp Val Asp Ile Ala Thr Leu Leu
            195                 200                 205

Ala Phe Lys Ala Phe Gly Val Ala Val Phe Leu Ile Ile Pro Ile Ala
210                 215                 220

Val Gly Tyr Ser Pro Leu Glu Ala Val Ile Gly Ala Ser Ile Val Tyr
225                 230                 235                 240

Met Thr His Gly Leu Val Ala Cys Val Val Phe Met Leu Ala His Val
            245                 250                 255

Ile Glu Pro Ala Glu Phe Leu Asp Pro Asp Asn Leu His Ile Asp Asp
            260                 265                 270

Glu Trp Ala Ile Ala Gln Val Lys Thr Thr Val Asp Phe Ala Pro Asn
            275                 280                 285

Asn Thr Ile Ile Asn Trp Tyr Val Gly Gly Leu Asn Tyr Gln Thr Val
            290                 295                 300

His His Leu Phe Pro His Ile Cys His Ile His Tyr Pro Lys Ile Ala
305                 310                 315                 320

Pro Ile Leu Ala Glu Val Cys Glu Glu Phe Gly Val Asn Tyr Ala Val
            325                 330                 335

His Gln Thr Phe Phe Gly Ala Leu Ala Ala Asn Tyr Ser Trp Leu Lys
            340                 345                 350

Lys Met Ser Ile Asn Pro Glu Thr Lys Ala Ile Glu Gln
            355                 360                 365

<210> SEQ ID NO 19
<211> LENGTH: 35
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence: PCR Primer

<400> SEQUENCE: 19
ccaagcttct gcaggagctc ttttttttt ttttt                               35

<210> SEQ ID NO 20
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer
<221> NAME/KEY: misc_feature
<222> LOCATION: ()..()
<223> OTHER INFORMATION: n at positions 21 and 27 may be a, c, g, or t/u

<400> SEQUENCE: 20
cuacuacuac uacaycayac ntayacnaay at                                 32

<210> SEQ ID NO 21
<211> LENGTH: 27
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer
<221> NAME/KEY: misc_feature

```
<222> LOCATION: ()..()
<223> OTHER INFORMATION: n at positions 13 and 19 may be a, c, g, or t/u

<400> SEQUENCE: 21
caucaucauc aunggraana rrtgrtg                                        27

<210> SEQ ID NO 22
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 22
cuacuacuac uaggagtcct ctacggtgtt ttg                                 33

<210> SEQ ID NO 23
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 23
caucaucauc auatgatgct caagctgaaa ctg                                 33

<210> SEQ ID NO 24
<211> LENGTH: 5
<212> TYPE: PRT
<213> ORGANISM: Mortierella alpina
<220> FEATURE:
<221> NAME/KEY: UNSURE
<222> LOCATION: (1)..(5)
<223> OTHER INFORMATION: Amino acids in positions 2 and 3 vary in the
      histidine box

<400> SEQUENCE: 24

Gln Xaa Xaa His His
1               5

<210> SEQ ID NO 25
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 25
cuacuacuac uactcgagca agatgggaac ggaccaagg                           39

<210> SEQ ID NO 26
<211> LENGTH: 39
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer
```

```
<400> SEQUENCE: 26
caucaucauc auctcgagct actcttcctt gggacggag                                  39

<210> SEQ ID NO 27
<211> LENGTH: 47
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 27
cuacuacuac uatctagact cgagaccatg gctgctgctc cagtgtg                         47

<210> SEQ ID NO 28
<211> LENGTH: 40
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 28
caucaucauc ataggcctcg agttactgcg ccttacccat                                 40

<210> SEQ ID NO 29
<211> LENGTH: 36
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 29
cuacuacuac uaggatccat ggcacctccc aacact                                     36

<210> SEQ ID NO 30
<211> LENGTH: 41
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Combined DNA/RNA Molecule: PCR
      Primer

<400> SEQUENCE: 30
caucaucauc auggtacctc gagttacttc ttgaaaaaga c                               41

<210> SEQ ID NO 31
<211> LENGTH: 1219
<212> TYPE: DNA
<213> ORGANISM: Homo sapiens

<400> SEQUENCE: 31
gcacgccgac cggcgccggg agatcctggc aaagtatcca gagataaagt ccttgatgaa           60
acctgatccc aatttgatat ggattataat tatgatggtt ctcacccagt tgggtgcatt          120
ttacatagta aaagacttgg actggaaatg ggtcatattt ggggcctatg cgtttggcag          180
ttgcattaac cactcaatga ctctggctat tcatgagatt gcccacaatg ctgcctttgg          240
```

```
caactgcaaa gcaatgtgga atcgctggtt tggaatgttt gctaatcttc ctattgggat        300
tccatattca atttccttta agaggtatca catggatcat catcggtacc ttggagctga        360
tggcgtcgat gtagatattc ctaccgattt tgagggctgg ttcttctgta ccgctttcag        420
aaagtttata tgggttattc ttcagcctct cttttatgcc tttcgacctc tgttcatcaa        480
ccccaaacca attacgtatc tggaagttat caataccgtg cacaggtca cttttgacat         540 tttaatttat tacttttttgg gaattaaatc cttagtctac atgttggcag catctttact       600
tggcctgggt ttgcacccaa tttctggaca ttttatagct gagcattaca tgttcttaaa        660
gggtcatgaa acttactcat attatgggcc tctgaattta cttaccttca atgtgggtta       720
tcataatgaa catcatgatt tccccaacat tcctggaaaa agtcttccac tggtgaggaa        780
aatagcagct gaatactatg acaacctccc tcactacaat tcctggataa agtactgta        840 tgattttgtg atggatgata caataagtcc ctactcaaga atgaagaggc accaaaaagg       900
agagatggtg ctggagtaaa tatcattagt gccaaaggga ttcttctcca aaactttaga       960
tgataaaatg gaattttttgc attattaaac ttgagaccag tgatgctcag aagctccccct    1020 ggcacaattt cagagtaaga gctcggtgat accaagaagt gaatctggct tttaaacagt     1080
cagcctgact ctgtactgct cagtttcact cacaggaaac ttgtgacttg tgtattatcg     1140
tcattgagga tgtttcactc atgtctgtca ttttataagc atatcattta aaaagcttct     1200
aaaaagctat ttcgccagg                                                  1219

<210> SEQ ID NO 32
<211> LENGTH: 655
<212> TYPE: DNA
<213> ORGANISM: Homo sapiens

<400> SEQUENCE: 32
ttaccttcta cgtccgcttc ttcctcactt atgtgccact attggggctg aaagcttcct        60 gggcctttttc ttcatagtca ggttcctgga aagcaactgg tttgtgtggg tgacacagat      120
gaaccatatt cccatgcaca ttgatcatga ccggaacatg gactgggttt ccacccagct      180
ccaggccaca tgcaatgtcc acaagtctgc cttcaatgac tggttcagtg gacacctcaa     240
cttccagatt gagcaccatc tttttcccac gatgcctcga cacaattacc acaaagtggc    300
tcccctggtg cagtccttgt gtgccaagca tggcatagag taccagtcca gcccctgct     360 gtcagccttc gccgacatca tccactcact aaaggagtca gggcagctct ggctagatgc    420
ctatcttcac caataacaac agccaccctg cccagtctgg aagaagagga ggaagactct   480
ggagccaagg cagaggggag cttgaggac aatgccacta tagtttaata ctcagagggg     540
gttgggtttg gggacataaa gcctctgact caaactcctc cctttatct tctagccaca     600 gttctaagac ccaaagtggg gggtggacac agaagtccct aggagggaag gagct          655

<210> SEQ ID NO 33
<211> LENGTH: 304
<212> TYPE: DNA
<213> ORGANISM: Homo sapiens

<400> SEQUENCE: 33 gtctttact ttggcaatgg ctggattcct accctcatca cggcctttgt ccttgctacc         60
tctcaggccc aagctggatg gctgcaacat gattatggcc acctgtcgt ctacagaaaa       120 cccaagtgga accaccttgt ccacaaattc gtcattggcc acttaaaggg tgcctctgcc      180
```

```
aactggtgga atcatcgcca cttccagcac cacgccaagc ctaacatctt ccacaaggat    240
cccgatgtga acatgctgca cgtgtttgtt ctgggcgaat ggcagcccat cgagtacggc    300
aaga                                                                 304
```

```
<210> SEQ ID NO 34
<211> LENGTH: 918
<212> TYPE: DNA
<213> ORGANISM: Homo sapiens

<400> SEQUENCE: 34
cagggaccta ccccgcgcta cttcacctgg gacgaggtgg cccagcgctc agggtgcgag     60
gagcggtggc tagtgatcga ccgtaaggtg tacaacatca gcgagttcac ccgccggcat    120 ccaggggggct cccgggtcat cagccactac gccgggcagg atgccacgga tccctttgtg   180
gccttccaca tcaacaaggg ccttgtgaag aagtatatga actctctcct gattggagaa    240
ctgtctccag agcagcccag ctttgagccc accaagaata aagagctgac agatgagttc    300
cgggagctgc gggccacagt ggagcggatg gggctcatga aggccaacca tgtcttcttc    360
ctgctgtacc tgctgcacat cttgctgctg atggtgcag cctggctcac cctttgggtc     420
tttgggacgt ccttttttgcc cttcctcctc tgtgcggtgc tgctcagtgc agttcaggcc   480
caggctggct ggctgcagca tgactttggg cacctgtcgg tcttcagcac ctcaaagtgg    540
aaccatctgc tacatcattt tgtgattggc cacctgaagg gggccccgc cagttggtgg     600 aaccacatgc acttccagca ccatgccaag cccaactgct ccgcaaaga cccagacatc     660 aacatgcatc ccttcttctt tgccttgggg aagatcctct ctgtggagct tgggaaacag    720
aagaaaaaat atatgccgta caaccaccag cacaratact tcttcctaat tgggcccca     780 gccttgctgc ctctctactt ccagtggtat attttctatt ttgttatcca gcgaaagaag    840
tgggtggact ggcctggat cagcaaacag gaatacgatg aagccgggct tccattgtcc     900
accgcaaatg cttctaaa                                                  918
```

```
<210> SEQ ID NO 35
<211> LENGTH: 1686
<212> TYPE: DNA
<213> ORGANISM: Homo sapiens

<400> SEQUENCE: 35
gccacttaaa gggtgcctct gccaactggt ggaatcatcg ccacttccag caccacgcca     60
agcctaacat cttccacaag gatcccgatg tgaacatgct gcacgtgttt gttctgggcg    120
aatggcagcc catcgagtac ggcaagaaga agctgaaata cctgccctac aatcaccagc    180
acgaatactt cttcctgatt gggccgccgc tgctcatccc catgtatttc cagtaccaga    240
tcatcatgac catgatcgtc cataagaact gggtggacct ggcctgggcc gtcagctact    300
acatccggtt cttcatcacc tacatccctt tctacggcat cctgggagcc ctccttttcc    360
tcaacttcat caggttcctg gagagccact ggtttgtgtg ggtcacacag atgaatcaca    420
tcgtcatgga gattgaccag gaggcctacc gtgactggtt cagtagccag ctgacagcca    480
cctgcaacgt ggagcagtcc ttcttcaacg actggttcag tggacacctt aacttccaga    540
ttgagcacca cctcttcccc accatgcccc ggcacaactt acacaagatc gccccgctgg    600
tgaagtctct atgtgccaag catggcattg aataccagga gaagccgcta ctgagggccc    660
tgctggacat catcaggtcc ctgaagaagt ctggaagct gtggctggac gcctaccttc    720
acaaatgaag ccacagcccc cgggacaccg tggggaaggg gtgcaggtgg ggtgatggcc    780
```

-continued

```
agaggaatga tgggcttttg ttctgagggg tgtccgagag gctggtgtat gcactgctca      840
cggaccccat gttggatctt tctcccttc cctctcctt tttctcttca catctcccc          900 atagcaccct gccctcatgg gacctgccct ccctcagccg tcagccatca gccatggccc      960
tcccagtgcc tcctagcccc ttcttccaag gagcagagag gtggccaccg ggggtggctc     1020
tgtcctacct ccactctctg cccctaaaga tgggaggaga ccagcggtcc atgggtctgg     1080
cctgtgagtc tccccttgca gcctggtcac taggcatcac ccccgctttg gttcttcaga     1140
tgctcttggg gttcataggg gcaggtccta gtcgggcagg gccctgacc ctcccggcct      1200 ggcttcactc tccctgacgg ctgccattgg tccacccttt catagagagg cctgctttgt     1260
tacaaagctc gggtctccct cctgcagctc ggttaagtac ccgaggcctc tcttaagatg     1320
tccagggccc caggcccgcg ggcacagcca gcccaaacct tgggccctgg aagagtcctc     1380
caccccatca ctagagtgct ctgaccctgg gctttcacgg gccccattcc accgcctccc     1440
caacttgagc ctgtgacctt gggaccaaag ggggagtccc tcgtctcttg tgactcagca     1500
gaggcagtgg ccacgttcag ggaggggccg gctggcctgg aggctcagcc caccctccag     1560
cttttcctca gggtgtcctg aggtccaaga ttctggagca atctgaccct tctccaaagg     1620
ctctgttatc agctgggcag tgccagccaa tccctggcca tttggcccca ggggacgtgg     1680
gccctg                                                                1686

<210> SEQ ID NO 36
<211> LENGTH: 1843
<212> TYPE: DNA
<213> ORGANISM: Homo sapiens

<400> SEQUENCE: 36
gtcttttact ttggcaatgg ctggattcct accctcatca cggcctttgt ccttgctacc       60
tctcaggccc aagctggatg gctgcaacat gattatggcc acctgtctgt ctacagaaaa      120
cccaagtgga accaccttgt ccacaaattc gtcattggcc acttaaaggg tgcctctgcc      180
aactggtgga atcatcgcca cttccagcac cacgccaagc ctaacatctt ccacaaggat      240
cccgatgtga acatgctgca cgtgtttgtt ctgggcgaat ggcagcccat cgagtacggc      300
aagaagaagc tgaaatacct gccctacaat caccagcacg aatacttctt cctgattggg      360
ccgccgctgc tcatccccat gtatttccag taccagatca tcatgaccat gatcgtccat      420
aagaactggg tggacctggc ctgggccgtc agctactaca tccggttctt catcacctac      480
atccctttct acggcatcct gggagccctc cttttcctca acttcatcag gttcctggag      540
agccactggt ttgtgtgggt cacacagatg aatcacatcg tcatggagat tgaccaggag      600
gcctaccgtg actggttcag tagccagctg acagccacct gcaacgtgga gcagtccttc      660
ttcaacgact ggttcagtgg acaccttaac ttccagattg agcaccacct cttcccacc       720 atgcccccggc acaacttaca caagatcgcc ccgctggtga agtctctatg tgccaagcat      780
ggcattgaat accaggagaa gccgctactg agggccctgc tggacatcat caggtccctg      840
aagaagtctg ggaagctgtg gctggacgcc taccttcaca aatgaagcca cagccccgg       900 gacaccgtgg ggaaggggtg caggtggggt gatggccaga ggaatgatgg cttttgttc       960 tgaggggtgt ccgagaggct ggtgtatgca ctgctcacgg accccatgtt ggatctttct     1020
ccctttctcc tctcctttt ctcttcacat ctccccata gcaccctgcc ctcatgggac       1080
ctgccctccc tcagccgtca gccatcagcc atggccctcc cagtgcctcc tagcccttc      1140
```

-continued

| | |
|---|---|
| ttccaaggag cagagaggtg gccaccgggg gtggctctgt cctacctcca ctctctgccc | 1200 |
| ctaaagatgg gaggagacca gcggtccatg ggtctggcct gtgagtctcc ccttgcagcc | 1260 |
| tggtcactag gcatcacccc cgctttggtt cttcagatgc tcttggggtt catagggggca | 1320 |
| ggtcctagtc gggcagggcc cctgaccctc ccggcctggc ttcactctcc ctgacggctg | 1380 |
| ccattggtcc acccttcat agagaggcct gctttgttac aaagctcggg tctccctcct | 1440 |
| gcagctcggt taagtacccg aggcctctct taagatgtcc agggcccag gcccgcgggc | 1500 |
| acagccagcc caaaccttgg gccctggaag agtcctccac cccatcacta gagtgctctg | 1560 |
| accctgggct ttcacgggcc ccattccacc gcctccccaa cttgagcctg tgaccttggg | 1620 |
| accaaagggg gagtccctcg tctcttgtga ctcagcagag gcagtggcca cgttcaggga | 1680 |
| ggggccggct ggcctggagg ctcagcccac cctccagctt ttcctcaggg tgtcctgagg | 1740 |
| tccaagattc tggagcaatc tgaccccttct ccaaaggctc tgttatcagc tgggcagtgc | 1800 |
| cagccaatcc ctggccattt ggccccaggg gacgtgggcc ctg | 1843 |

<210> SEQ ID NO 37
<211> LENGTH: 2257
<212> TYPE: DNA
<213> ORGANISM: Homo sapiens

<400> SEQUENCE: 37

| | |
|---|---|
| cagggaccta ccccgcgcta cttcacctgg gacgaggtgg cccagcgctc agggtgcgag | 60 |
| gagcggtggc tagtgatcga ccgtaaggtg tacaacatca gcgagttcac ccgccggcat | 120 |
| ccaggggggct cccgggtcat cagccactac gccgggcagg atgccacgga tccctttgtg | 180 |
| gccttccaca tcaacaaggg ccttgtgaag aagtatatga actctctcct gattggagaa | 240 |
| ctgtctccag agcagcccag cttttgagccc accaagaata aagagctgac agatgagttc | 300 |
| cgggagctgc gggccacagt ggagcggatg gggctcatga aggccaacca tgtcttcttc | 360 |
| ctgctgtacc tgctgcacat cttgctgctg gatggtgcag cctggctcac cctttgggtc | 420 |
| tttgggacgt cctttttgcc cttcctcctc tgtgcggtgc tgctcagtgc agttcagcag | 480 |
| gcccaagctg gatggctgca acatgattat ggccaccctgt ctgtctacag aaaacccaag | 540 |
| tggaaccacc ttgtccacaa attcgtcatt ggccacttaa agggtgcctc tgccaactgg | 600 |
| tggaatcatc gccacttcca gcaccacgcc aagcctaaca tcttccacaa ggatcccgat | 660 |
| gtgaacatgc tgcacgtgtt tgttctgggc gaatggcagc ccatcgagta cggcaagaag | 720 |
| aagctgaaat acctgccta caataccag cacgaatact tcttcctgat tgggccgccg | 780 |
| ctgctcatcc ccatgtattt ccagtaccag atcatcatga ccatgatcgt ccataagaac | 840 |
| tgggtggacc tggcctgggc cgtcagctac tacatccggt tcttcatcac ctacatccct | 900 |
| ttctacgca tcctgggagc cctccttttc ctcaacttca tcaggttcct ggagagccac | 960 |
| tggtttgtgt gggtcacaca gatgaatcac atcgtcatgg agattgacca ggaggcctac | 1020 |
| cgtgactggt tcagtagcca gctgacagcc acctgcaacg tggagcagtc cttcttcaac | 1080 |
| gactggttca gtggacacct taacttccag attgagcacc acctcttccc caccatgccc | 1140 |
| cggcacaact tacacaagat cgccccgctg gtgaagtctc tatgtgccaa gcatggcatt | 1200 |
| gaataccagg agaagccgct actgagggcc ctgctggaca tcatcaggtc cctgaagaag | 1260 |
| tctgggaagc tgtggctgga cgcctacctt cacaaatgaa gccacagccc ccgggacacc | 1320 |
| gtggggaagg ggtgcaggtg gggtgatggc cagaggaatg atgggctttt gttctgaggg | 1380 |
| gtgtccgaga ggctggtgta tgcactgctc acggacccca tgttggatct ttctcccttt | 1440 |

-continued

```
ctcctctcct ttttctcttc acatctcccc catagcaccc tgccctcatg ggacctgccc      1500
tccctcagcc gtcagccatc agccatggcc ctccagtgc ctcctagccc cttcttccaa       1560
ggagcagaga ggtggccacc gggggtggct ctgtcctacc tccactctct gcccctaaag      1620
atgggaggag accagcggtc catgggtctg gcctgtgagt ctccccttgc agcctggtca      1680
ctaggcatca ccccgctttt ggttcttcag atgctcttgg ggttcatagg ggcaggtcct      1740
agtcgggcag ggcccctgac cctcccggcc tggcttcact ctccctgacg gctgccattg      1800 gtccacccctt tcatagagag gcctgctttg ttacaaagct cgggtctccc tcctgcagct     1860
cggttaagta cccgaggcct ctcttaagat gtccagggcc ccaggcccgc gggcacagcc      1920
agcccaaacc ttgggccctg gaagagtcct ccaccccatc actagagtgc tctgaccctg      1980
ggctttcacg ggccccattc caccgcctcc ccaacttgag cctgtgacct tgggaccaaa      2040 ggggggagtcc ctcgtctctt gtgactcagc agaggcagtg gccacgttca gggaggggcc    2100
ggctggcctg gaggctcagc ccacctcca gcttttcctc agggtgtcct gaggtccaag       2160
attctggagc aatctgaccc ttctccaaag gctctgttat cagctgggca gtgccagcca     2220
atccctggcc atttggcccc aggggacgtg ggccctg                               2257
```

<210> SEQ ID NO 38
<211> LENGTH: 406
<212> TYPE: PRT
<213> ORGANISM: Homo sapiens
<220> FEATURE:
<221> NAME/KEY: UNSURE
<222> LOCATION: (1)..(406)
<223> OTHER INFORMATION: Amino acids 306, 329, 331, 334, 358, 375, and 382 uncertain of sequence

<400> SEQUENCE: 38

```
His Ala Asp Arg Arg Glu Ile Leu Ala Lys Tyr Pro Glu Ile Lys
1               5                   10                  15

Ser Leu Met Lys Pro Asp Pro Asn Leu Ile Trp Ile Ile Met Met
                20                  25                  30

Val Leu Thr Gln Leu Gly Ala Phe Tyr Ile Val Lys Asp Leu Asp Trp
            35                  40                  45

Lys Trp Val Ile Phe Gly Ala Tyr Ala Phe Gly Ser Cys Ile Asn His
    50                  55                  60

Ser Met Thr Leu Ala Ile His Glu Ile Ala His Asn Ala Ala Phe Gly
65                  70                  75                  80

Asn Cys Lys Ala Met Trp Asn Arg Trp Phe Gly Met Phe Ala Asn Leu
                85                  90                  95

Pro Ile Gly Ile Pro Tyr Ser Ile Ser Phe Lys Arg Tyr His Met Asp
            100                 105                 110

His His Arg Tyr Leu Gly Ala Asp Gly Val Asp Val Asp Ile Pro Thr
        115                 120                 125

Asp Phe Glu Gly Trp Phe Phe Cys Thr Ala Phe Arg Lys Phe Ile Trp
    130                 135                 140

Val Ile Leu Gln Pro Leu Phe Tyr Ala Phe Arg Pro Leu Phe Ile Asn
145                 150                 155                 160

Pro Lys Pro Ile Thr Tyr Leu Glu Val Ile Asn Thr Val Ala Gln Val
                165                 170                 175

Thr Phe Asp Ile Leu Ile Tyr Tyr Phe Leu Gly Ile Lys Ser Leu Val
            180                 185                 190

Tyr Met Leu Ala Ala Ser Leu Leu Gly Leu Gly Leu His Pro Ile Ser
```

-continued

```
                195                 200                 205
Gly His Phe Ile Ala Glu His Tyr Met Phe Leu Lys Gly His Glu Thr
    210                 215                 220
Tyr Ser Tyr Tyr Gly Pro Leu Asn Leu Leu Thr Phe Asn Val Gly Tyr
225                 230                 235                 240
His Asn Glu His His Asp Phe Pro Asn Ile Pro Gly Lys Ser Leu Pro
                245                 250                 255
Leu Val Arg Lys Ile Ala Ala Glu Tyr Tyr Asp Asn Leu Pro His Tyr
                260                 265                 270
Asn Ser Trp Ile Lys Val Leu Tyr Asp Phe Val Met Asp Asp Thr Ile
                275                 280                 285
Ser Pro Tyr Ser Arg Met Lys Arg His Gln Lys Gly Glu Met Val Leu
                290                 295                 300
Glu Xaa Ile Ser Leu Val Pro Lys Gly Phe Phe Ser Lys Thr Leu Asp
305                 310                 315                 320
Asp Lys Met Glu Phe Leu His Tyr Xaa Thr Xaa Asp Gln Xaa Cys Ser
                325                 330                 335
Glu Ala Pro Leu Ala Gln Phe Gln Ser Lys Ser Ser Val Ile Pro Arg
                340                 345                 350
Ser Glu Ser Gly Phe Xaa Thr Val Ser Leu Thr Leu Tyr Cys Ser Val
                355                 360                 365
Ser Leu Thr Gly Asn Leu Xaa Leu Val Tyr Tyr Arg His Xaa Gly Cys
                370                 375                 380
Phe Thr His Val Cys His Phe Ile Ser Ile Ser Phe Lys Lys Leu Leu
385                 390                 395                 400
Lys Ser Tyr Phe Ala Arg
                405

<210> SEQ ID NO 39
<211> LENGTH: 218
<212> TYPE: PRT
<213> ORGANISM: Homo sapiens
<220> FEATURE:
<221> NAME/KEY: UNSURE
<222> LOCATION: (1)..(218)
<223> OTHER INFORMATION: Amino acids 145, 168, 174, 186, 189, 198, and
      202 uncertain of sequence

<400> SEQUENCE: 39

Tyr Leu Leu Arg Pro Leu Pro His Leu Cys Ala Thr Ile Gly Ala
1               5                   10                  15
Glu Ser Phe Leu Gly Leu Phe Phe Ile Val Arg Phe Leu Glu Ser Asn
                20                  25                  30
Trp Phe Val Trp Val Thr Gln Met Asn His Ile Pro Met His Ile Asp
                35                  40                  45
His Asp Arg Asn Met Asp Trp Val Ser Thr Gln Leu Gln Ala Thr Cys
                50                  55                  60
Asn Val His Lys Ser Ala Phe Asn Asp Trp Phe Ser Gly His Leu Asn
65              70                  75                  80
Phe Gln Ile Glu His Leu Phe Pro Thr Met Pro Arg His Asn Tyr
                85                  90                  95
His Lys Val Ala Pro Leu Val Gln Ser Leu Cys Ala Lys His Gly Ile
                100                 105                 110
Glu Tyr Gln Ser Lys Pro Leu Leu Ser Ala Phe Ala Asp Ile Ile His
                115                 120                 125
Ser Leu Lys Glu Ser Gly Gln Leu Trp Leu Asp Ala Tyr Leu His Gln
```

```
              130                 135                 140
Xaa Gln Gln Pro Pro Cys Pro Val Trp Lys Lys Arg Arg Lys Thr Leu
145                 150                 155                 160

Glu Pro Arg Gln Arg Gly Ala Xaa Gly Thr Met Pro Leu Xaa Phe Asn
                165                 170                 175

Thr Gln Arg Gly Leu Gly Leu Gly Thr Xaa Ser Leu Xaa Leu Lys Leu
            180                 185                 190

Leu Pro Phe Ile Phe Xaa Pro Gln Phe Xaa Asp Pro Lys Trp Gly Val
        195                 200                 205

Asp Thr Glu Val Pro Arg Arg Glu Gly Ala
    210                 215

<210> SEQ ID NO 40
<211> LENGTH: 87
<212> TYPE: PRT
<213> ORGANISM: Homo sapiens
<220> FEATURE:
<221> NAME/KEY: UNSURE
<222> LOCATION: (1)..(87)
<223> OTHER INFORMATION: Amino acid 87 uncertain of sequence

<400> SEQUENCE: 40

Val Phe Tyr Phe Gly Asn Gly Trp Ile Pro Thr Leu Ile Thr Ala Phe
1               5                   10                  15

Val Leu Ala Thr Ser Gln Ala Gln Ala Gly Trp Leu Gln His Asp Tyr
            20                  25                  30

Gly His Leu Ser Val Tyr Arg Lys Pro Lys Trp Asn His Leu Val His
        35                  40                  45

Lys Phe Val Ile Gly His Leu Lys Gly Ala Ser Ala Asn Trp Trp Asn
    50                  55                  60

His Arg His Phe Gln His His Ala Lys Pro Asn Leu Gly Glu Trp Gln
65                  70                  75                  80

Pro Ile Glu Tyr Gly Lys Xaa
                85

<210> SEQ ID NO 41
<211> LENGTH: 306
<212> TYPE: PRT
<213> ORGANISM: Homo sapiens
<220> FEATURE:
<221> NAME/KEY: UNSURE
<222> LOCATION: (1)..(306)
<223> OTHER INFORMATION: Amino acid 252 uncertain of sequence

<400> SEQUENCE: 41

Gln Gly Pro Thr Pro Arg Tyr Phe Thr Trp Asp Glu Val Ala Gln Arg
1               5                   10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60

Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
                100                 105                 110
```

```
Met Lys Ala Asn His Val Phe Phe Leu Leu Tyr Leu Leu His Ile Leu
        115                 120                 125
Leu Leu Asp Gly Ala Ala Trp Leu Thr Leu Trp Val Phe Gly Thr Ser
    130                 135                 140
Phe Leu Pro Phe Leu Leu Cys Ala Val Leu Leu Ser Ala Val Gln Ala
145                 150                 155                 160
Gln Ala Gly Trp Leu Gln His Asp Phe Gly His Leu Ser Val Phe Ser
                165                 170                 175
Thr Ser Lys Trp Asn His Leu Leu His His Phe Val Ile Gly His Leu
            180                 185                 190
Lys Gly Ala Pro Ala Ser Trp Trp Asn His Met His Phe Gln His His
        195                 200                 205
Ala Lys Pro Asn Cys Phe Arg Lys Asp Pro Asp Ile Asn Met His Pro
    210                 215                 220
Phe Phe Phe Ala Leu Gly Lys Ile Leu Ser Val Glu Leu Gly Lys Gln
225                 230                 235                 240
Lys Lys Lys Tyr Met Pro Tyr Asn His Gln His Xaa Tyr Phe Phe Leu
                245                 250                 255
Ile Gly Pro Pro Ala Leu Leu Pro Leu Tyr Phe Gln Trp Tyr Ile Phe
            260                 265                 270
Tyr Phe Val Ile Gln Arg Lys Lys Trp Val Asp Leu Ala Trp Ile Ser
        275                 280                 285
Lys Gln Glu Tyr Asp Glu Ala Gly Leu Pro Leu Ser Thr Ala Asn Ala
    290                 295                 300
Ser Lys
305

<210> SEQ ID NO 42
<211> LENGTH: 562
<212> TYPE: PRT
<213> ORGANISM: Homo sapiens
<220> FEATURE:
<221> NAME/KEY: UNSURE
<222> LOCATION: (1)..(562)
<223> OTHER INFORMATION: Amino acids 242, 268, 405, 438, 464, 482, 497,
      and 562 uncertain of sequence

<400> SEQUENCE: 42

His Leu Lys Gly Ala Ser Ala Asn Trp Trp Asn His Arg His Phe Gln
1               5                   10                  15
His His Ala Lys Pro Asn Ile Phe His Lys Asp Pro Asp Val Asn Met
            20                  25                  30
Leu His Val Phe Val Leu Gly Glu Trp Gln Pro Ile Glu Tyr Gly Lys
        35                  40                  45
Lys Lys Leu Lys Tyr Leu Pro Tyr Asn His Gln His Glu Tyr Phe Phe
    50                  55                  60
Leu Ile Gly Pro Pro Leu Leu Ile Pro Met Tyr Phe Gln Tyr Gln Ile
65                  70                  75                  80
Ile Met Thr Met Ile Val His Lys Asn Trp Val Asp Leu Ala Trp Ala
                85                  90                  95
Val Ser Tyr Tyr Ile Arg Phe Phe Ile Thr Tyr Ile Pro Phe Tyr Gly
            100                 105                 110
Ile Leu Gly Ala Leu Leu Phe Leu Asn Phe Ile Arg Phe Leu Glu Ser
        115                 120                 125
His Trp Phe Val Trp Val Thr Gln Met Asn His Ile Val Met Glu Ile
    130                 135                 140
```

-continued

```
Asp Gln Glu Ala Tyr Arg Asp Trp Phe Ser Ser Gln Leu Thr Ala Thr
145                 150                 155                 160

Cys Asn Val Glu Gln Ser Phe Phe Asn Asp Trp Phe Ser Gly His Leu
                165                 170                 175

Asn Phe Gln Ile Glu His His Leu Phe Pro Thr Met Pro Arg His Asn
            180                 185                 190

Leu His Lys Ile Ala Pro Leu Val Lys Ser Leu Cys Ala Lys His Gly
        195                 200                 205

Ile Glu Tyr Gln Glu Lys Pro Leu Leu Arg Ala Leu Leu Asp Ile Ile
    210                 215                 220

Arg Ser Leu Lys Lys Ser Gly Lys Leu Trp Leu Asp Ala Tyr Leu His
225                 230                 235                 240

Lys Xaa Ser His Ser Pro Arg Asp Thr Val Gly Lys Gly Cys Arg Trp
                245                 250                 255

Gly Asp Gly Gln Arg Asn Asp Gly Leu Leu Phe Xaa Gly Val Ser Glu
                260                 265                 270

Arg Leu Val Tyr Ala Leu Leu Thr Asp Pro Met Leu Asp Leu Ser Pro
                275                 280                 285

Phe Leu Leu Ser Phe Phe Ser Ser His Leu Pro His Ser Thr Leu Pro
290                 295                 300

Ser Trp Asp Leu Pro Ser Leu Ser Arg Gln Pro Ser Ala Met Ala Leu
305                 310                 315                 320

Pro Val Pro Pro Ser Pro Phe Phe Gln Gly Ala Glu Arg Trp Pro Pro
                325                 330                 335

Gly Val Ala Leu Ser Tyr Leu His Ser Leu Pro Leu Lys Met Gly Gly
                340                 345                 350

Asp Gln Arg Ser Met Gly Leu Ala Cys Glu Ser Pro Leu Ala Ala Trp
                355                 360                 365

Ser Leu Gly Ile Thr Pro Ala Leu Val Leu Gln Met Leu Leu Gly Phe
370                 375                 380

Ile Gly Ala Gly Pro Ser Arg Ala Gly Pro Leu Thr Leu Pro Ala Trp
385                 390                 395                 400

Leu His Ser Pro Xaa Arg Leu Pro Leu Val His Pro Phe Ile Glu Arg
                405                 410                 415

Pro Ala Leu Leu Gln Ser Ser Gly Leu Pro Pro Ala Ala Arg Leu Ser
                420                 425                 430

Thr Arg Gly Leu Ser Xaa Asp Val Gln Gly Pro Arg Pro Ala Gly Thr
                435                 440                 445

Ala Ser Pro Asn Leu Gly Pro Trp Lys Ser Pro Pro His His Xaa
                450                 455                 460

Ser Ala Leu Thr Leu Gly Phe His Gly Pro His Ser Thr Ala Ser Pro
465                 470                 475                 480

Thr Xaa Ala Cys Asp Leu Gly Thr Lys Gly Val Pro Arg Leu Leu
                485                 490                 495

Xaa Leu Ser Arg Gly Ser Gly His Val Gln Gly Gly Ala Gly Trp Pro
                500                 505                 510

Gly Gly Ser Ala His Pro Pro Ala Phe Pro Gln Gly Val Leu Arg Ser
                515                 520                 525

Lys Ile Leu Glu Gln Ser Asp Pro Ser Pro Lys Ala Leu Leu Ser Ala
                530                 535                 540

Gly Gln Cys Gln Pro Ile Pro Gly His Leu Ala Pro Gly Asp Val Gly
545                 550                 555                 560
```

Pro Xaa

<210> SEQ ID NO 43
<211> LENGTH: 615
<212> TYPE: PRT
<213> ORGANISM: Homo sapiens
<220> FEATURE:
<221> NAME/KEY: UNSURE
<222> LOCATION: (1)..(615)
<223> OTHER INFORMATION: Amino acids 295, 321, 458, 491, 517, 535, 550, and 615 uncertain of sequence

<400> SEQUENCE: 43

```
Val Phe Tyr Phe Gly Asn Gly Trp Ile Pro Thr Leu Ile Thr Ala Phe
  1               5                  10                  15

Val Leu Ala Thr Ser Gln Ala Gln Ala Gly Trp Leu Gln His Asp Tyr
                 20                  25                  30

Gly His Leu Ser Val Tyr Arg Lys Pro Lys Trp Asn His Leu Val His
             35                  40                  45

Lys Phe Val Ile Gly His Leu Lys Gly Ala Ser Ala Asn Trp Trp Asn
 50                  55                  60

His Arg His Phe Gln His Ala Lys Pro Asn Ile Phe His Lys Asp
 65                  70                  75                  80

Pro Asp Val Asn Met Leu His Val Phe Val Leu Gly Glu Trp Gln Pro
                 85                  90                  95

Ile Glu Tyr Gly Lys Lys Lys Leu Lys Tyr Leu Pro Tyr Asn His Gln
            100                 105                 110

His Glu Tyr Phe Phe Leu Ile Gly Pro Pro Leu Leu Ile Pro Met Tyr
            115                 120                 125

Phe Gln Tyr Gln Ile Ile Met Thr Met Ile Val His Lys Asn Trp Val
130                 135                 140

Asp Leu Ala Trp Ala Val Ser Tyr Tyr Ile Arg Phe Ile Thr Tyr
145                 150                 155                 160

Ile Pro Phe Tyr Gly Ile Leu Gly Ala Leu Leu Phe Leu Asn Phe Ile
                165                 170                 175

Arg Phe Leu Glu Ser His Trp Phe Val Trp Val Thr Gln Met Asn His
            180                 185                 190

Ile Val Met Glu Ile Asp Gln Glu Ala Tyr Arg Asp Trp Phe Ser Ser
            195                 200                 205

Gln Leu Thr Ala Thr Cys Asn Val Glu Gln Ser Phe Phe Asn Asp Trp
210                 215                 220

Phe Ser Gly His Leu Asn Phe Gln Ile Glu His His Leu Phe Pro Thr
225                 230                 235                 240

Met Pro Arg His Asn Leu His Lys Ile Ala Pro Leu Val Lys Ser Leu
                245                 250                 255

Cys Ala Lys His Gly Ile Glu Tyr Gln Glu Lys Pro Leu Leu Arg Ala
            260                 265                 270

Leu Leu Asp Ile Ile Arg Ser Leu Lys Lys Ser Gly Lys Leu Trp Leu
            275                 280                 285

Asp Ala Tyr Leu His Lys Xaa Ser His Ser Pro Arg Asp Thr Val Gly
290                 295                 300

Lys Gly Cys Arg Trp Gly Asp Gly Gln Arg Asn Asp Gly Leu Leu Phe
305                 310                 315                 320

Xaa Gly Val Ser Glu Arg Leu Val Tyr Ala Leu Leu Thr Asp Pro Met
                325                 330                 335

Leu Asp Leu Ser Pro Phe Leu Leu Ser Phe Phe Ser Ser His Leu Pro
```

```
                    340                 345                 350
His Ser Thr Leu Pro Ser Trp Asp Leu Pro Ser Leu Ser Arg Gln Pro
            355                 360                 365

Ser Ala Met Ala Leu Pro Val Pro Pro Ser Pro Phe Phe Gln Gly Ala
            370                 375                 380

Glu Arg Trp Pro Pro Gly Val Ala Leu Ser Tyr Leu His Ser Leu Pro
385                 390                 395                 400

Leu Lys Met Gly Gly Asp Gln Arg Ser Met Gly Leu Ala Cys Glu Ser
                405                 410                 415

Pro Leu Ala Ala Trp Ser Leu Gly Ile Thr Pro Ala Leu Val Leu Gln
            420                 425                 430

Met Leu Leu Gly Phe Ile Gly Ala Gly Pro Ser Arg Ala Gly Pro Leu
            435                 440                 445

Thr Leu Pro Ala Trp Leu His Ser Pro Xaa Arg Leu Pro Leu Val His
            450                 455                 460

Pro Phe Ile Glu Arg Pro Ala Leu Leu Gln Ser Ser Gly Leu Pro Pro
465                 470                 475                 480

Ala Ala Arg Leu Ser Thr Arg Gly Leu Ser Xaa Asp Val Gln Gly Pro
                485                 490                 495

Arg Pro Ala Gly Thr Ala Ser Pro Asn Leu Gly Pro Trp Lys Ser Pro
            500                 505                 510

Pro Pro His His Xaa Ser Ala Leu Thr Leu Gly Phe His Gly Pro His
            515                 520                 525

Ser Thr Ala Ser Pro Thr Xaa Ala Cys Asp Leu Gly Thr Lys Gly Gly
            530                 535                 540

Val Pro Arg Leu Leu Xaa Leu Ser Arg Gly Ser Gly His Val Gln Gly
545                 550                 555                 560

Gly Ala Gly Trp Pro Gly Gly Ser Ala His Pro Ala Phe Pro Gln
                565                 570                 575

Gly Val Leu Arg Ser Lys Ile Leu Glu Gln Ser Asp Pro Ser Pro Lys
            580                 585                 590

Ala Leu Leu Ser Ala Gly Gln Cys Gln Pro Ile Pro Gly His Leu Ala
            595                 600                 605

Pro Gly Asp Val Gly Pro Xaa
        610                 615

<210> SEQ ID NO 44
<211> LENGTH: 753
<212> TYPE: PRT
<213> ORGANISM: Homo sapiens
<220> FEATURE:
<221> NAME/KEY: UNSURE
<222> LOCATION: (1)..(753)
<223> OTHER INFORMATION: Amino acids 433, 459, 596, 629, 655, 673, 688,
      and 753 uncertain of sequence

<400> SEQUENCE: 44

Gln Gly Pro Thr Pro Arg Tyr Phe Thr Trp Asp Glu Val Ala Gln Arg
1               5                   10                  15

Ser Gly Cys Glu Glu Arg Trp Leu Val Ile Asp Arg Lys Val Tyr Asn
                20                  25                  30

Ile Ser Glu Phe Thr Arg Arg His Pro Gly Gly Ser Arg Val Ile Ser
            35                  40                  45

His Tyr Ala Gly Gln Asp Ala Thr Asp Pro Phe Val Ala Phe His Ile
        50                  55                  60

Asn Lys Gly Leu Val Lys Lys Tyr Met Asn Ser Leu Leu Ile Gly Glu
```

-continued

```
            65                  70                  75                  80
Leu Ser Pro Glu Gln Pro Ser Phe Glu Pro Thr Lys Asn Lys Glu Leu
                    85                  90                  95
Thr Asp Glu Phe Arg Glu Leu Arg Ala Thr Val Glu Arg Met Gly Leu
                100                 105                 110
Met Lys Ala Asn His Val Phe Phe Leu Leu Tyr Leu Leu His Ile Leu
                115                 120                 125
Leu Leu Asp Gly Ala Ala Trp Leu Thr Leu Trp Val Phe Gly Thr Ser
            130                 135                 140
Phe Leu Pro Phe Leu Leu Cys Ala Val Leu Leu Ser Ala Val Gln Gln
145                 150                 155                 160
Ala Gln Ala Gly Trp Leu Gln His Asp Tyr Gly His Leu Ser Val Tyr
                165                 170                 175
Arg Lys Pro Lys Trp Asn His Leu Val His Lys Phe Val Ile Gly His
                180                 185                 190
Leu Lys Gly Ala Ser Ala Asn Trp Trp Asn His Arg His Phe Gln His
                195                 200                 205
His Ala Lys Pro Asn Ile Phe His Lys Asp Pro Asp Val Asn Met Leu
            210                 215                 220
His Val Phe Val Leu Gly Glu Trp Gln Pro Ile Glu Tyr Gly Lys Lys
225                 230                 235                 240
Lys Leu Lys Tyr Leu Pro Tyr Asn His Gln His Glu Tyr Phe Phe Leu
                245                 250                 255
Ile Gly Pro Pro Leu Leu Ile Pro Met Tyr Phe Gln Tyr Gln Ile Ile
                260                 265                 270
Met Thr Met Ile Val His Lys Asn Trp Val Asp Leu Ala Trp Ala Val
            275                 280                 285
Ser Tyr Tyr Ile Arg Phe Phe Ile Thr Tyr Ile Pro Phe Tyr Gly Ile
            290                 295                 300
Leu Gly Ala Leu Leu Phe Leu Asn Phe Ile Arg Phe Leu Glu Ser His
305                 310                 315                 320
Trp Phe Val Trp Val Thr Gln Met Asn His Ile Val Met Glu Ile Asp
                325                 330                 335
Gln Glu Ala Tyr Arg Asp Trp Phe Ser Ser Gln Leu Thr Ala Thr Cys
                340                 345                 350
Asn Val Glu Gln Ser Phe Phe Asn Asp Trp Phe Ser Gly His Leu Asn
                355                 360                 365
Phe Gln Ile Glu His His Leu Phe Pro Thr Met Pro Arg His Asn Leu
            370                 375                 380
His Lys Ile Ala Pro Leu Val Lys Ser Leu Cys Ala Lys His Gly Ile
385                 390                 395                 400
Glu Tyr Gln Glu Lys Pro Leu Leu Arg Ala Leu Leu Asp Ile Ile Arg
                405                 410                 415
Ser Leu Lys Lys Ser Gly Lys Leu Trp Leu Asp Ala Tyr Leu His Lys
                420                 425                 430
Xaa Ser His Ser Pro Arg Asp Thr Val Gly Lys Gly Cys Arg Trp Gly
            435                 440                 445
Asp Gly Gln Arg Asn Asp Gly Leu Leu Phe Xaa Gly Val Ser Glu Arg
            450                 455                 460
Leu Val Tyr Ala Leu Leu Thr Asp Pro Met Leu Asp Leu Ser Pro Phe
465                 470                 475                 480
Leu Leu Ser Phe Phe Ser Ser His Leu Pro His Ser Thr Leu Pro Ser
                485                 490                 495
```

```
Trp Asp Leu Pro Ser Leu Ser Arg Gln Pro Ser Ala Met Ala Leu Pro
            500                 505                 510
Val Pro Pro Ser Pro Phe Phe Gln Gly Ala Glu Arg Trp Pro Pro Gly
        515                 520                 525
Val Ala Leu Ser Tyr Leu His Ser Leu Pro Leu Lys Met Gly Gly Asp
    530                 535                 540
Gln Arg Ser Met Gly Leu Ala Cys Glu Ser Pro Leu Ala Ala Trp Ser
545                 550                 555                 560
Leu Gly Ile Thr Pro Ala Leu Val Leu Gln Met Leu Leu Gly Phe Ile
                565                 570                 575
Gly Ala Gly Pro Ser Arg Ala Gly Pro Leu Thr Leu Pro Ala Trp Leu
            580                 585                 590
His Ser Pro Xaa Arg Leu Pro Leu Val His Pro Phe Ile Glu Arg Pro
        595                 600                 605
Ala Leu Leu Gln Ser Ser Gly Leu Pro Ala Ala Arg Leu Ser Thr
    610                 615                 620
Arg Gly Leu Ser Xaa Asp Val Gln Gly Pro Arg Pro Ala Gly Thr Ala
625                 630                 635                 640
Ser Pro Asn Leu Gly Pro Trp Lys Ser Pro Pro His His Xaa Ser
                645                 650                 655
Ala Leu Thr Leu Gly Phe His Gly Pro His Ser Thr Ala Ser Pro Thr
            660                 665                 670
Xaa Ala Cys Asp Leu Gly Thr Lys Gly Gly Val Pro Arg Leu Leu Xaa
        675                 680                 685
Leu Ser Arg Gly Ser Gly His Val Gln Gly Gly Ala Gly Trp Pro Gly
    690                 695                 700
Gly Ser Ala His Pro Pro Ala Phe Pro Gln Gly Val Leu Arg Ser Lys
705                 710                 715                 720
Ile Leu Glu Gln Ser Asp Pro Ser Pro Lys Ala Leu Leu Ser Ala Gly
                725                 730                 735
Gln Cys Gln Pro Ile Pro Gly His Leu Ala Pro Gly Asp Val Gly Pro
            740                 745                 750
Xaa

<210> SEQ ID NO 45
<211> LENGTH: 746
<212> TYPE: DNA
<213> ORGANISM: Dictyostelium discoideum

<400> SEQUENCE: 45
cgtatgtcac tccattccaa actcgttcat ggtatcataa atatcaacac atttacgctc      60
cactcctcta tggtatttac acactcaaat atcgtactca agattgggaa gcttttgtaa     120
aggatggtaa aaatggtgca attcgtgtta gtgtcgccac aaatttcgat aaggccgctt     180
acgtcattgg taaattgtct tttgttttct tccgtttcat ccttccactc cgttatcata     240
gctttacaga tttaatttgt tatttcctca ttgctgaatt cgtctttggt tggtatctca     300
caattaattt ccaagttagt catgtcgctg aagatctcaa attctttgct acccctgaaa     360
gaccagatga accatctcaa atcaatgaag attgggcaat ccttcaactt aaaactactc     420
aagattatgg tcatggttca ctcctttgta cctttttag tggttcttta aatcatcaag     480
ttgttcatca tttattccca tcaattgctc aagattccta cccacaactt gtaccaattg     540
taaaagaagt ttgtaaagaa cataacatta cttaccacat taaaccaaac ttcactgaag     600
```

-continued

```
ctattatgtc acacattaat tacctttaca aaatgggtaa tgatccagat tatgttaaaa      660
aaccattagc ctcaaaagat gattaaatga aataacttaa aaaccaatta tttactttg       720 acaaacagta atattaataa atacaa                                           746
```

<210> SEQ ID NO 46
<211> LENGTH: 228
<212> TYPE: PRT
<213> ORGANISM: Dictyostelium discoideum
<220> FEATURE:
<221> NAME/KEY: UNSURE
<222> LOCATION: (1)..(228)
<223> OTHER INFORMATION: Amino acid 228 uncertain of sequence

<400> SEQUENCE: 46

```
Tyr Val Thr Pro Phe Gln Thr Arg Ser Trp Tyr His Lys Tyr Gln His
1               5                   10                  15

Ile Tyr Ala Pro Leu Leu Tyr Gly Ile Tyr Thr Leu Lys Tyr Arg Thr
            20                  25                  30

Gln Asp Trp Glu Ala Phe Val Lys Asp Gly Lys Asn Gly Ala Ile Arg
        35                  40                  45

Val Ser Val Ala Thr Asn Phe Asp Lys Ala Ala Tyr Val Ile Gly Lys
50                  55                  60

Leu Ser Phe Val Phe Phe Arg Phe Ile Leu Pro Leu Arg Tyr His Ser
65                  70                  75                  80

Phe Thr Asp Leu Ile Cys Tyr Phe Leu Ile Ala Glu Phe Val Phe Gly
                85                  90                  95

Trp Tyr Leu Thr Ile Asn Phe Gln Val Ser His Val Ala Glu Asp Leu
            100                 105                 110

Lys Phe Phe Ala Thr Pro Glu Arg Pro Asp Glu Pro Ser Gln Ile Asn
        115                 120                 125

Glu Asp Trp Ala Ile Leu Gln Leu Lys Thr Thr Gln Asp Tyr Gly His
130                 135                 140

Gly Ser Leu Leu Cys Thr Phe Phe Ser Gly Ser Leu Asn His Gln Val
145                 150                 155                 160

Val His His Leu Phe Pro Ser Ile Ala Gln Asp Phe Tyr Pro Gln Leu
                165                 170                 175

Val Pro Ile Val Lys Glu Val Cys Lys Glu His Asn Ile Thr Tyr His
            180                 185                 190

Ile Lys Pro Asn Phe Thr Glu Ala Ile Met Ser His Ile Asn Tyr Leu
        195                 200                 205

Tyr Lys Met Gly Asn Asp Pro Asp Tyr Val Lys Lys Pro Leu Ala Ser
210                 215                 220

Lys Asp Asp Xaa
225
```

<210> SEQ ID NO 47
<211> LENGTH: 494
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone
<221> NAME/KEY: misc_feature
<222> LOCATION: ()..()
<223> OTHER INFORMATION: n at positions 11, 20, 29, 31, 40, 53, 453, and
      489 may be a, c, g, or t

<400> SEQUENCE: 47

```
ttttggaagg ntccaagttn accacggant nggcaagttn acggggcgga aancggtttt      60 cccccaagc ttttgtcga ctggttctgt ggtggcttcc agtaccaagt cgaccaccac      120
ttattcccca gcctgccccg acacaatctg gccaagacac acgcactggt cgaatcgttc      180
tgcaaggagt ggggtgtcca gtaccacgaa gccgacctcg tggacgggac catggaagtc      240
ttgcaccatt tgggcagcgt ggccggcgaa ttcgtcgtgg attttgtacg cgacggaccc      300
gccatgtaat cgtcgttcgt gacgatgcaa gggttcacgc acatctacac acactcactc      360
acacaactag tgtaactcgt atagaattcg gtgtcgacct ggaccttgtt tgactggttg      420
gggatagggt aggtaggcgg acgcgtgggt cgncccgggg aattctgtga ccggtacctg      480
gcccgcgtna aagt                                                        494
```

<210> SEQ ID NO 48
<211> LENGTH: 102
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone
<221> NAME/KEY: UNSURE
<222> LOCATION: (1)..(102)
<223> OTHER INFORMATION: Amino acids 4, 7, 10, 11, 14, and 18 uncertain
      of sequence

<400> SEQUENCE: 48

Phe Trp Lys Xaa Pro Ser Xaa Pro Arg Xaa Xaa Gln Val Xaa Gly Ala
1               5                   10                  15

Glu Xaa Gly Phe Pro Pro Lys Pro Phe Val Asp Trp Phe Cys Gly Gly
            20                  25                  30

Phe Gln Tyr Gln Val Asp His His Leu Phe Pro Ser Leu Pro Arg His
        35                  40                  45

Asn Leu Ala Lys Thr His Ala Leu Val Glu Ser Phe Cys Lys Glu Trp
    50                  55                  60

Gly Val Gln Tyr His Glu Ala Asp Leu Val Asp Gly Thr Met Glu Val
65                  70                  75                  80

Leu His His Leu Gly Ser Val Ala Gly Glu Phe Val Val Asp Phe Val
                85                  90                  95

Arg Asp Gly Pro Ala Met
            100

<210> SEQ ID NO 49
<211> LENGTH: 520
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 49

```
ggatggagtt cgtctggatc gctgtgcgct acgcgacgtg gtttaagcgt catgggtgcg      60
cttgggtaca cgccggggca gtcgttgggc atgtacttgt gcgcctttgg tctcggctgc     120
atttacattt ttctgcagtt cgccgtaagt cacacccatt tgcccgtgag caacccggag     180
gatcagctgc attggctcga gtacgcgcgg accacactgt gaacatcagc accaagtcgt     240
ggtttgtcac atggtggatg tcgaacctca actttcagat cgagcaccac cttttcccca     300
```

```
cggcgcccca gttccgtttc aaggagatca gcccgcgcgt cgaggccctc ttcaagcgcc    360
acggtctccc ttactacgac atgccctaca cgagcgccgt ctccaccacc tttgccaacc    420
tctactccgt cggccattcc gtcggcgacg ccaagcgcga ctagcctctt ttcctagacc    480
ttaattcccc accccacccc atgttctgtc ttcctcccgc                          520
```

```
<210> SEQ ID NO 50
<211> LENGTH: 153
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 50
```

```
Met Glu Phe Val Trp Ile Ala Val Arg Tyr Ala Thr Trp Phe Lys Arg
1               5                   10                  15

His Gly Cys Ala Trp Val His Ala Gly Ala Val Val Gly His Val Leu
            20                  25                  30

Val Arg Leu Trp Ser Arg Leu His Leu His Phe Ser Ala Val Arg Arg
        35                  40                  45

Lys Ser His Pro Phe Ala Arg Glu Gln Pro Gly Gly Ser Ala Ala Leu
    50                  55                  60

Ala Arg Val Arg Ala Asp His Thr Val Asn Ile Ser Thr Lys Ser Trp
65                  70                  75                  80

Phe Val Thr Trp Trp Met Ser Asn Leu Asn Phe Gln Ile Glu His His
                85                  90                  95

Leu Phe Pro Thr Ala Pro Gln Phe Arg Phe Lys Glu Ile Ser Pro Arg
            100                 105                 110

Val Glu Ala Leu Phe Lys Arg His Gly Leu Pro Tyr Tyr Asp Met Pro
        115                 120                 125

Tyr Thr Ser Ala Val Ser Thr Thr Phe Ala Asn Leu Tyr Ser Val Gly
    130                 135                 140

His Ser Val Gly Asp Ala Lys Arg Asp
145                 150
```

```
<210> SEQ ID NO 51
<211> LENGTH: 420
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 51
acgcgtccgc ccacgcgtcc gccgcgagca actcatcaag gaaggctact tgacccctc     60 gctcccgcac atgacgtacc gcgtggtcga gattgttgtt ctcttcgtgc tttccttttg   120
gctgatgggt cagtcttcac ccctcgcgct cgctctcggc attgtcgtca gcggcatctc   180
tcagggtcgc tgcggctggg taatgcatga tgggccat gggtcgttca ctggtgtcat    240
ttggcttgac gaccggttgt gcgagttctt ttacggcgtt ggttgtggca tgagcggtca   300
ttactggaaa aaccagcaca gcaaacacca cgcagcgcca aaccggctcg agcacgatgt   360
agatctcaac accttgccat tggtggcctt caacgagcgc gtcgtgcgca aggtccgacc   420
```

```
<210> SEQ ID NO 52
<211> LENGTH: 140
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence:
      Schizochytrium cDNA Clone

<400> SEQUENCE: 52

Arg Val Arg Pro Arg Val Arg Arg Glu Gln Leu Ile Lys Glu Gly Tyr
1               5                   10                  15

Phe Asp Pro Ser Leu Pro His Met Thr Tyr Arg Val Val Glu Ile Val
            20                  25                  30

Val Leu Phe Val Leu Ser Phe Trp Leu Met Gly Gln Ser Ser Pro Leu
        35                  40                  45

Ala Leu Ala Leu Gly Ile Val Val Ser Gly Ile Ser Gln Gly Arg Cys
    50                  55                  60

Gly Trp Val Met His Glu Met Gly His Gly Ser Phe Thr Gly Val Ile
65                  70                  75                  80

Trp Leu Asp Asp Arg Leu Cys Glu Phe Phe Tyr Gly Val Gly Cys Gly
                85                  90                  95

Met Ser Gly His Tyr Trp Lys Asn Gln His Ser Lys His His Ala Ala
            100                 105                 110

Pro Asn Arg Leu Glu His Asp Val Asp Leu Asn Thr Leu Pro Leu Val
        115                 120                 125

Ala Phe Asn Glu Arg Val Val Arg Lys Val Arg Pro
    130                 135                 140
```

METHODS AND COMPOSITIONS FOR SYNTHESIS OF LONG CHAIN POLYUNSATURATED FATTY ACIDS IN PLANTS

CROSS-REFERENCE TO RELATED APPLICATION

This application is a continuation-in-part of U.S. Ser. No. 08/834,655, filed Apr. 11, 1997, now U.S. Pat. No. 5,968,809 and a continuation in part of U.S. Ser. No. 08/833/610, filed Apr. 11, 1997 now U.S. Pat. No. 5,972,664, U.S. Ser. No. 08/834,033 filed Apr. 11, 1997 now U.S. Pat. No. 6,075,183, and U.S. Ser. No. 08/956,985 filed Oct. 24, 1997, now U.S. Pat. No. 6,051,754 which disclosures are incorporated herein by reference.

INTRODUCTION

1. Field of the Invention

This invention relates to modulating levels of enzymes and/or enzyme components capable of altering the production of long chain polyunsaturated fatty acids (PUFAS) in a host plant. The invention is exemplified by the production of PUFAS in plants.

2. Background

Two main families of polyunsaturated fatty acids (PUFAs) are the $\omega 3$ fatty acids, exemplified by arachidonic acid, and the $\omega 6$ fatty acids, exemplified by eicosapentaenoic acid. PUFAs are important components of the plasma membrane of the cell, where they may be found in such forms as phospholipids. PUFAs also serve as precursors to other molecules of importance in human beings and animals, including the prostacyclins, leukotrienes and prostaglandins. PUFAs are necessary for proper development, particularly in the developing infant brain, and for tissue formation and repair.

Four major long chain PUFAs of importance include docosahexaenoic acid (DHA) and eicosapentaenoic acid (EPA), which are primarily found in different types of fish oil, gamma-linolenic acid (GLA), which is found in the seeds of a number of plants, including evening primrose (*Oenothera biennis*), borage (*Borago officinalis*) and black currants (*Ribes nigrum*), and stearidonic acid (SDA), which is found in marine oils and plant seeds. Both GLA and another important long chain PUFA, arachidonic acid (ARA), are found in filamentous fungi. ARA can be purified from animal tissues including liver and adrenal gland.

For DHA, a number of sources exist for commercial production including a variety of marine organisms, oils obtained from cold water marine fish, and egg yolk fractions. For ARA, microorganisms including the genera *Mortierella, Entomophthora, Phytium* and *Porphyridium* can be used for commercial production. Commercial sources of SDA include the genera *Trichodesma* and *Echium*. Commercial sources of GLA include evening primrose, black currants and borage. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFA. Natural sources also are subject to uncontrollable fluctuations in availability. Fish stocks may undergo natural variation or may be depleted by overfishing. Fish oils have unpleasant tastes and odors, which may be impossible to economically separate from the desired product, and can render such products unacceptable as food supplements. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in $\omega 3$ fatty acids have an increased tendency to bleed (U.S. Pat. No. 4,874,603). Unpleasant tastes and odors of the supplements can make such regimens undesirable, and may inhibit compliance by the patient.

A number of enzymes are involved in PUFA biosynthesis. Linoleic acid (LA, 18:2 $\Delta 9$, 12) is produced from oleic acid (18:1 $\Delta 9$) by a $\Delta 12$-desaturase. GLA (18:3 $\Delta 6$, 9, 12) is produced from linoleic acid (LA, 18:2 $\Delta 9$, 12) by a $\Delta 6$-desaturase. ARA (20:4 $\Delta 5$, 8, 11, 14) production from DGLA (20:3 $\Delta 8$, 11, 14) is catalyzed by a $\Delta 5$-desaturase. However, animals cannot desaturate beyond the $\Delta 9$ position and therefore cannot convert oleic acid (18:1 $\Delta 9$) into linoleic acid (18:2 $\Delta 9$, 12). Likewise, $\alpha$-linolenic acid (ALA, 18:3 $\Delta 9$, 12, 15) cannot be synthesized by mammals. Other eukaryotes, including fungi and plants, have enzymes which desaturate at positions $\Delta 21$ and $\Delta 15$. The major poly-unsaturated fatty acids of animals therefore are either derived from diet and/or from desaturation and elongation of linoleic acid (18:2 $\Delta 9$, 12) or $\alpha$-linolenic acid (18:3 $\Delta 9$, 12, 15).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Therefore it is of interest to obtain genetic material involved in PUFA biosynthesis from species that naturally produce these fatty acids and to express the isolated material alone or in combination in a heterologous system which can be manipulated to allow production of commercial quantities of PUFAS.

Production of gamma-linolenic acid by a $\Delta 6$-desaturase is described in U.S. Pat. No. 5,552,306 and U.S. Pat. No. 5,614, 393. Production of 8, 11-eicosadienoic acid using *Mortierella alpina* is disclosed in U.S. Pat. No. 5,376,541. Production of docosahexaenoic acid by dinoflagellates is described in U.S. Pat. No. 5,407,957. Cloning of a $\Delta 6$-desaturase from borage is described in PCT publication WO 96/21022. Cloning of $\Delta 9$-desaturases is described in the published patent applications PCT WO 91/13972, EP 0 550 162 A1, EP 0 561 569 A2, EP 0 644 263 A2, and EP 0 736 598 A1, and in U.S. Pat. No. 5,057,419. Cloning of $\Delta 12$-desaturases from various organisms is described in PCT publication WO 94/11516 and U.S. Pat. No. 5,443,974. Cloning of Δ15-desaturases from various organisms is described in PCT publication WO 93/11245. A Δ6 palmitoyl-acyl carrier protein desaturase from *Thumbergia alata* and its expression in *E. coli* is described in U.S. Pat. No. 5,614,400. Expression of a soybean stearyl-ACP desaturase in transgenic soybean embryos using a 35S promoter is disclosed in U.S. Pat. No. 5,443,974.

SUMMARY OF THE INVENTION

Novel compositions and methods are provided for preparation of poly-unsaturated long chain fatty acids and desaturases in plants and plant cells. The methods involve growing a host plant cell of interest transformed with an expression cassette functional in a host plant cell, the expression cassette comprising a transcriptional and translational initiation regulatory region, joined in reading frame 5' to a DNA sequence encoding a desaturase polypeptide capable of modulating the production of PUFAs. Expression of the desaturase polypeptide provides for an alteration in the PUFA profile of host plant cells as a result of altered concentrations of enzymes involved in PUFA biosynthesis. Of particular interest is the selective control of PUFA production in plant tissues and/or plant parts such as leaves, roots, fruits and seeds. The invention finds use for example in the large scale production of DHA, EPA, ARA, and GLA and for modification of the fatty acid profile of edible plant tissues and/or plant parts.

The present invention further includes a purified nucleotide sequence or polypeptide sequence that is substantially related or homologous to the nucleotide and peptide sequences presented in SEQ ID NO:1-SEQ ID NO:52. The present invention is further directed to methods of using the sequences presented in SEQ ID NO:1 to SEQ ID NO:40 as probes to identify related sequences, as components of expression systems and as components of systems useful for producing transgenic oil.

The present invention is further directed to formulas, dietary supplements or dietary supplements in the form of a liquid or a solid containing the long chain fatty acids of the invention. These formulas and supplements may be administered to a human or an animal.

The formulas and supplements of the invention may further comprise at least one macronutrient selected from the group consisting of coconut oil, soy oil, canola oil, mono- and diglycerides, glucose, edible lactose, electrodialysed whey, electrodialysed skim milk, milk whey, soy protein, and other protein hydrolysates.

The formulas of the present invention may further include at least one vitamin selected from the group consisting of Vitamins A, C, D, E, and B complex; and at least one mineral selected from the group consisting of calcium, magnesium, zinc, manganese, sodium, potassium, phosphorus, copper, chloride, iodine, selenium, and iron.

The present invention is further directed to a method of treating a patient having a condition caused by insufficient intake or production of polyunsaturated fatty acids comprising administering to the patient a dietary substitute of the invention in an amount sufficient to effect treatment of the patient.

The present invention is further directed to cosmetic and pharmaceutical compositions of the material of the invention.

The present invention is further directed to transgenic oils in pharmaceutically acceptable carriers. The present invention is further directed to nutritional supplements, cosmetic agents and infant formulae containing transgenic oils.

The present invention is further directed to a method for obtaining altered long chain polyunsaturated fatty acid biosynthesis comprising the steps of: growing a microbe having cells which contain a transgene which encodes a transgene expression product which desaturates a fatty acid molecule at carbon 5.5 or 12 from the carboxyl end of said fatty acid molecule, wherein the trangene is operably associated with an expression control sequence, under conditions whereby the transgene is expressed, whereby long chain polyunsaturated fatty acid biosynthesis in the cells is altered.

The present invention is further directed toward pharmaceutical compositions comprising at least one nutrient selected from the group consisting of a vitamin, a mineral, a carbohydrate, a sugar, an amino acid, a free fatty acid, a phospholipid, an antioxidant, and a phenolic compound.

BRIEF DESCRIPTION OF THE DRAWINGS

FIGS. 3A-E shows the DNA sequence (SEQ ID NO:1) of the *Mortierella alpina* Δ6 desaturase and the deduced amino acid sequence (SEQ ID NO:2).

FIG. 4 shows an alignment of the *Mortierella alpina* Δ6 desaturase amino acid sequence with other Δ6 desaturases and related sequences (SEQ ID NOS:7, 8, 9, 10, 11, 12 and 13).

FIGS. 5A-D shows the DNA sequence of the *Mortierella alpina* Δ12 desaturase (SEQ ID NO:3) and the deduced amino acid sequence (SEQ ID NO:4)

FIG. 6 shows the deduced amino acid sequence (SEQ ID NO:14) of the PCR fragment (see Example 1).

FIGS. 7A-D shows the DNA sequence of the *Mortierella alpina* Δ5 desaturase (SEQ ID NO:5).

FIG. 8 shows alignments of the protein sequence of the Δ5 desaturase (SEQ ID NO:6) with Δ6 desaturases and related sequences (SEQ ID NOS:15, 16, 17, 18).

FIG. 9 shows alignments of the protein sequence of the Ma 29 and contig 253538a.

FIG. 10 shows alignments of the protein sequence of Ma 524 and contig 253538a.

BRIEF DESCRIPTION OF THE SEQUENCE LISTINGS

Figure 1:
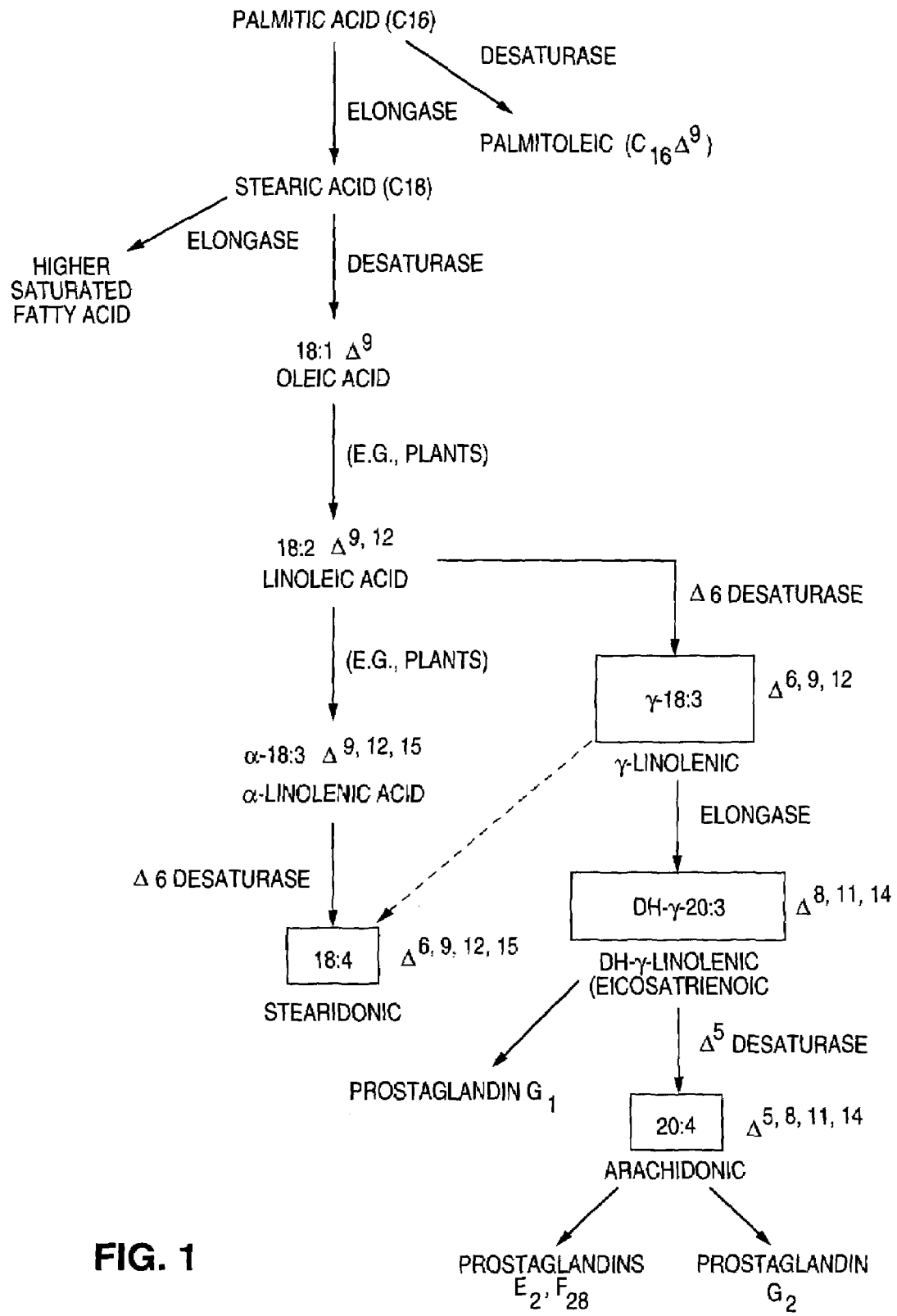
FIG. 1 shows possible pathways for the synthesis of arachidonic acid (20:4 Δ5, 8, 11, 14) and stearidonic acid (18:4 Δ6, 9, 12, 15) from palmitic acid ($C_{16}$) from a variety of organisms, including algae, *Mortierella* and humans. These PUFAs can serve as precursors to other molecules important for humans and other animals, including prostacyclins, leukotrienes, and prostaglandins, some of which are shown.

SEQ ID NO:1 shows the DNA sequence of the *Mortierella alpina* Δ6 desaturase.

SEQ ID NO:2 shows the amino acid sequence of the *Mortierella alpina* Δ6 desaturase.

SEQ ID NO:3 shows the DNA sequence of the *Mortierella alpina* Δ12 desaturase.

SEQ ID NO:4 shows the amino acid sequence of the *Mortierella alpina* Δ12 desaturase.

SEQ ID NO:5 shows the DNA sequence of the *Mortierella alpina* Δ5 desaturase.

SEQ ID NO:6 shows the amino acid sequence *Mortierella alpina* Δ5 desaturase.

SEQ ID NO:7-SEQ ID NO:13 show amino acid sequences that relate to *Mortierella alpina* Δ6 desaturase.

SEQ ID NO:14 shows an amino acid sequence of a PCR fragment of Example 1.

SEQ ID NO:15-SEQ ID NO:18 show amino acid sequences that relate to *Mortierella alpina* Δ5 and Δ6 desaturases.

SEQ ID NO:19-SEQ ID NO:30 show PCR primer sequences.

SEQ ID NO:31-SEQ ID NO:37 show human nucleotide sequences.

SEQ ID NO:38-SEQ ID NO:44 show human peptide sequences.

SEQ ID NO:45-SEQ ID NO:46 show the nucleotide and amino acid sequence of a *Dictyostelium discoideium* desaturase.

SEQ ID NO:47-SEQ ID NO:50 show the nucleotide and deduced amino acid sequence of a *Schizochytrium* cDNA clone.

DESCRIPTION OF THE PREFERRED EMBODIMENTS

In order to ensure a complete understanding of the invention, the following definitions are provided:

Δ5-Desaturase: Δ5 desaturase is an enzyme which introduces a double bond between carbons 5 and 6 from the carboxyl end of a fatty acid molecule.

Δ6-Desaturase: Δ6-desaturase is an enzyme which introduces a double bond between carbons 6 and 7 from the carboxyl end of a fatty acid molecule.

Δ9-Desaturase: Δ9-desaturase is an enzyme which introduces a double bond between carbons 9 and 10 from the carboxyl end of a fatty acid molecule.

Δ12-Desaturase: Δ12-desaturase is an enzyme which introduces a double bond between carbons 12 and 13 from the carboxyl end of a fatty acid molecule.

Fatty Acids: Fatty acids are a class of compounds containing a long hydrocarbon chain and a terminal carboxylate group. Fatty acids include the following:

| Fatty Acid | | |
|---|---|---|
| 12:0 | lauric acid | |
| 16:0 | palmitic acid | |
| 16:1 | palmitoleic acid | |
| 18:0 | stearic acid | |
| 18:1 | oleic acid | Δ9-18:1 |
| 18:2 Δ5, 9 | taxoleic acid | Δ5, 9-18:2 |
| 18:2 Δ6, 9 | 6,9-octadecadienoic acid | Δ6, 9-18:2 |
| 18:2 | linoleic acid | Δ9, 12-18:2 (LA) |
| 18:3 Δ6, 9, 12 | gamma-linolenic acid | Δ6, 9, 12-18:3 (GLA) |
| 18:3 Δ5, 9, 12 | pinolenic acid | Δ5, 9, 12-18:3 |
| 18:3 | alpha-linolenic acid | Δ9, 12, 15-18:3 (ALA) |
| 18:4 | stearidonic acid | Δ6, 9, 12, 15-18:4 (SDA) |
| 20:0 | Arachidic acid | |
| 20:1 | Eicoscenic Acid | |
| 22:0 | behehic acid | |
| 22:1 | erucic acid | |
| 22:2 | Docasadienoic acid | |
| 20:4 ω6 | arachidonic acid | Δ5, 8, 11, 14-20:4 (ARA) |
| 20:3 ω6 | ω6-eicosatrienoic dihomo-gamma linolenic | Δ8, 11, 14-20:3 (DGLA) |
| 20:5 ω3 | Eicosapentanoic (Timnodonic acid) | Δ5, 8, 11, 14, 17-20:5 (EPA) |
| 20:3 ω3 | ω3-eicosatrienoic | Δ11, 16, 17-20:3 |
| 20:4 ω3 | ω3-eicosatetraenoic | Δ8, 11, 14, 17-20:4 |
| 22:5 ω3 | Docosapentaenoic | Δ7, 10, 13, 16, 19-22:5 (ω3DPA) |
| 22:6 ω3 | Docosahexaenoic (cervonic acid) | Δ4, 7, 10, 13, 16, 19-22:6 (DHA) |
| 24:0 | Lignoceric acid | |

Taking into account these definitions, the present invention is directed to novel DNA sequences, DNA constructs, methods and compositions are provided which permit modification of the poly-unsaturated long chain fatty acid content of plant cells. Plant cells are transformed with an expression cassette comprising a DNA encoding a polypeptide capable of increasing the amount of one or more PUFA in a plant cell. Desirably, integration constructs may be prepared which provide for integration of the expression cassette into the genome of a host cell. Host cells are manipulated to express a sense or antisense DNA encoding a polypeptide(s) that has desaturase activity. By "desaturase" is intended a polypeptide which can desaturate one or more fatty acids to produce a mono- or poly-unsaturated fatty acid or precursor thereof of interest. By "polypeptide" is meant any chain of amino acids, regardless of length or post-translational modification, for example, glycosylation or phosphorylation. The substrate(s) for the expressed enzyme may be produced by the host cell or may be exogenously supplied.

To achieve expression in a host cell, the transformed DNA is operably associated with transcriptional and translational initiation and termination regulatory regions that are functional in the host cell. Constructs comprising the gene to be expressed can provide for integration into the genome of the host cell or can autonomously replicate in the host cell. For production of linoleic acid (LA), the expression cassettes generally used include a cassette which provides for Δ12 desaturase activity, particularly in a host cell which produces or can take up oleic acid. For production of ALA, the expression cassettes generally used include a cassette which provides for Δ15 or ω3 desaturase activity, particularly in a host cell which produces or can take up LA. For production of GLA or SDA, the expression cassettes generally used include a cassette which provides for Δ6 desaturase activity, particularly in a host cell which produces or can take up LA or ALA, respectively. Production of ω6-type unsaturated fatty acids, such as LA or GLA, is favored in a plant capable of producing ALA by inhibiting the activity of a Δ15 or ω3 type desaturase; this is accomplished by providing an expression cassette for an antisense Δ15 or ω3 transcript, or by disrupting a Δ15 or ω3 desaturase gene. Similarly, production of LA or ALA is favored in a plant having Δ6 desaturase activity by providing an expression cassette for an antisense Δ6 transcript, or by disrupting a Δ6 desaturase gene. Production of oleic acid likewise is favored in a plant having Δ12 desaturase activity by providing an expression cassette for an antisense Δ12 transcript, or by disrupting a Δ12 desaturase gene. For production of ARA, the expression cassette generally used provides for Δ5 desaturase activity, particularly in a host cell which produces or can take up DGLA. Production of ω6-type unsaturated fatty acids, such as ARA, is favored in a plant capable of producing ALA by inhibiting the activity of a Δ15 or ω3 type desaturase; this is accomplished by providing an expression cassette for an antisense Δ15 or ω3 transcript, or by disrupting a Δ15 or ω3 desaturase gene.

Transgenic Plant Production of Fatty Acids

Transgenic plant production of PUFAs offers several advantages over purification from natural sources such as fish or plants. Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of desaturase genes in particular tissues and/or plant parts means that greatly increased levels of desired PUFAs in those tissues and/or parts can be achieved, making recovery from those tissues more economical. For example, the desired PUFAs can be expressed in seed; methods of isolating seed oils are well established. In addition to providing a source for purification of desired PUFAs, seed oil components can be manipulated through expression of desaturase genes, either alone or in combination with other genes such as elongases, to provide seed oils having a particular PUFA profile in concentrated form. The concentrated seed oils then can be added to animal milks and/or synthetic or semi-synthetic milks to serve as infant formulas where human nursing is impossible or undesired, or in cases of malnourishment or disease in both adults and infants.

Figure 2:
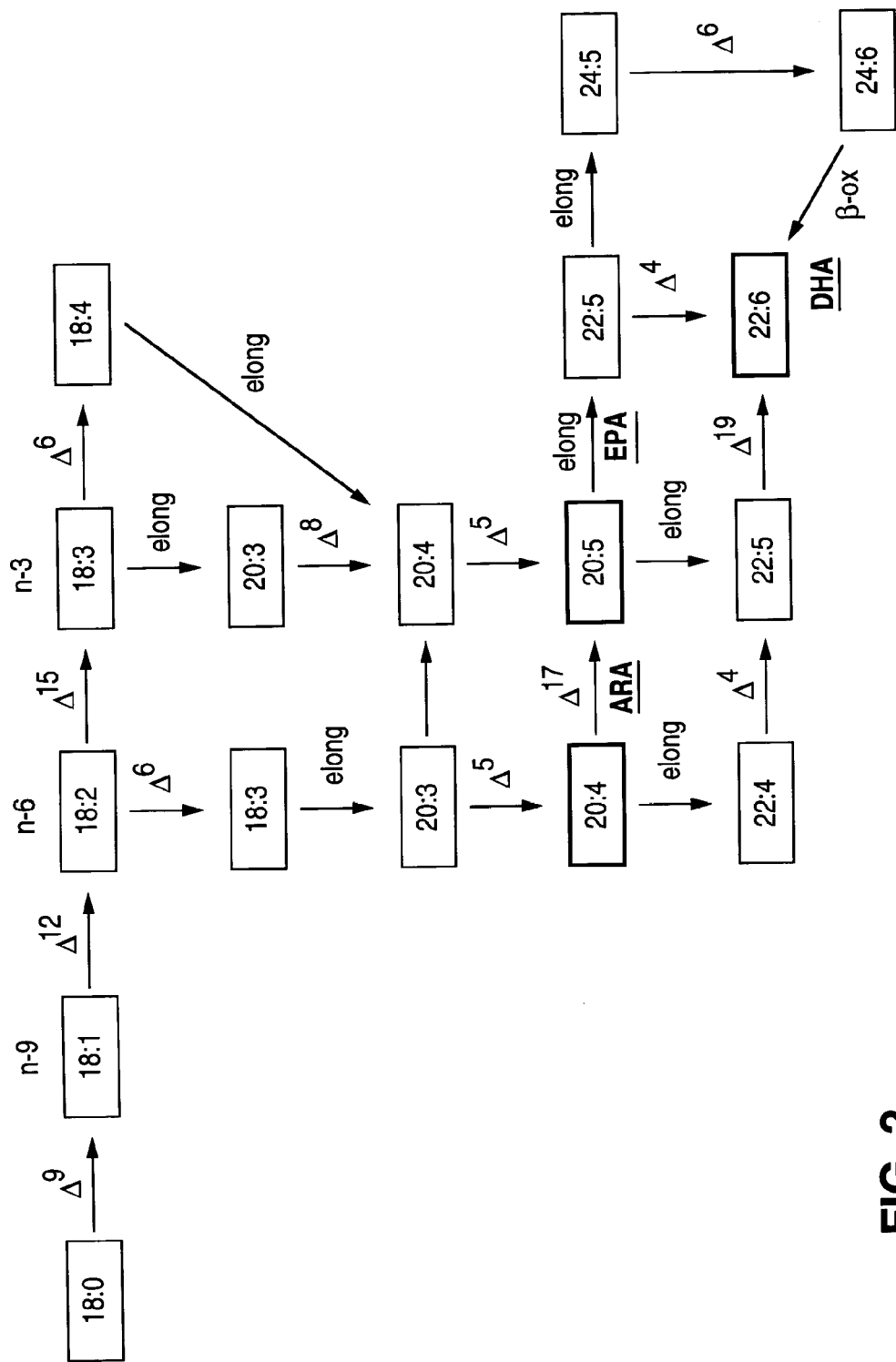
FIG. 2 shows possible pathways for production of PUFAs in addition to ARA, including EPA and DHA, again compiled from a variety of organisms.

For production of PUFAs, depending upon the host cell, the availability of substrate, and the desired end product(s), several polypeptides, particularly desaturases, are of interest including those polypeptides which catalyze the conversion of stearic acid to oleic acid, LA to GLA, of ALA to SDA, of oleic acid to LA, or of LA to ALA, which includes enzymes which desaturate at the $\Delta 6$, $\Delta 9$, $\Delta 12$, $\Delta 15$ or $\omega 3$ positions. Considerations for choosing a specific polypeptide having desaturase activity include the pH optimum of the polypeptide, whether the polypeptide is a rate limiting enzyme or a component thereof, whether the desaturase used is essential for synthesis of a desired poly-unsaturated fatty acid, and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying PUFA production in a given host cell. The polypeptide used in a particular situation therefore is one which can function under the conditions present in the intended host cell but otherwise can be any polypeptide having desaturase activity which has the desired characteristic of being capable of modifying the relative production of a desired PUFA. A scheme for the synthesis of arachidonic acid (20:4 $\Delta 5$, 8, 11, 14) from palmitic acid ($C_{16}$) is shown in FIG. 1. A key enzyme in this pathway is a $\Delta 5$-desaturase which converts DH-$\gamma$-linolenic acid (DGLA, eicosatrienoic acid) to ARA. Conversion of $\alpha$-linolenic acid (ALA) to stearidonic acid by a $\Delta 6$-desaturase is also shown. Production of PUFAs in addition to ARA, including EPA and DHA is shown in FIG. 2. A key enzyme in the synthesis of arachidonic acid (20:4 $\Delta 5$, 8, 11, 14) from stearic acid ($C_{18}$) is a $\Delta 6$-desaturase which converts the linoleic acid into $\gamma$-linolenic acid. Conversion of $\alpha$-linolenic acid (ALA) to stearidonic acid by a $\Delta 6$-desaturase also is shown. For production of ARA, the DNA sequence used encodes a polypeptide having $\Delta 5$ desaturase activity. In particular instances, this can be coupled with an expression cassette which provides for production of a polypeptide having $\Delta 6$ desaturase activity and, optionally, a transcription cassette providing for production of antisense sequences to a $\Delta 15$ transcription product. The choice of combination of cassettes used depends in part on the PUFA profile of the host cell. Where the host cell $\Delta 5$-desaturase activity is limiting, overexpression of $\Delta 5$ desaturase alone generally will be sufficient to provide for enhanced ARA production.

Sources of Polypeptides Having Desaturase Activity

As sources of polypeptides having desaturase activity and oligonucleotides encoding such polypeptides are organisms which produce a desired poly-unsaturated fatty acid. As an example, microorganisms having an ability to produce ARA can be used as a source of $\Delta 5$-desaturase genes; microorganisms which GLA or SDA can be used as a source of $\Delta 6$-desaturase and/or $\Delta 12$-desaturase genes. Such microorganisms include, for example, those belonging to the genera *Mortierella, Conidiobolus, Pythium, Phytophathora, Penicillium, Porphyridium, Coidosporium, Mucor, Fusarium, Aspergillus, Rhodotorula*, and *Entomophthora*. Within the genus *Porphyridium*, of particular interest is *Porphyridium cruentum*. Within the genus *Mortierella*, of particular interest are *Mortierella elongata, Mortierella exigua, Mortierella hygrophila, Mortierella ramanniana*, var. *angulispora*, and *Mortierella alpina*. Within the genus *Mucor*, of particular interest are *Mucor circinelloides* and *Mucor javanicus*.

DNAs encoding desired desaturases can be identified in a variety of ways. As an example, a source of the desired desaturase, for example genomic or cDNA libraries from *Mortierella*, is screened with detectable enzymatically- or chemically-synthesized probes, which can be made from DNA, RNA, or non-naturally occurring nucleotides, or mixtures thereof. Probes may be enzymatically synthesized from DNAs of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequence for the polypeptide having desaturase activity is from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring desaturase genes to produce a polypeptide having desaturase activity in vivo with more desirable physical and kinetic parameters for function in the host cell, such as a longer half-life or a higher rate of production of a desired polyunsaturated fatty acid.

Desirable cDNAs have less than 60% A+T composition, preferably less than 50% A+T composition. On a localized scale of a sliding window of 20 base pairs, it is preferable that there are no localized regions of the cDNA with greater than 75% A+T composition; with a window of 60 base pairs, it is preferable that there are no localized regions of the cDNA with greater than 60%, more preferably no localized regions with greater than 55% A+T composition.

Mortierella alpina Desaturases

Figure 3B:
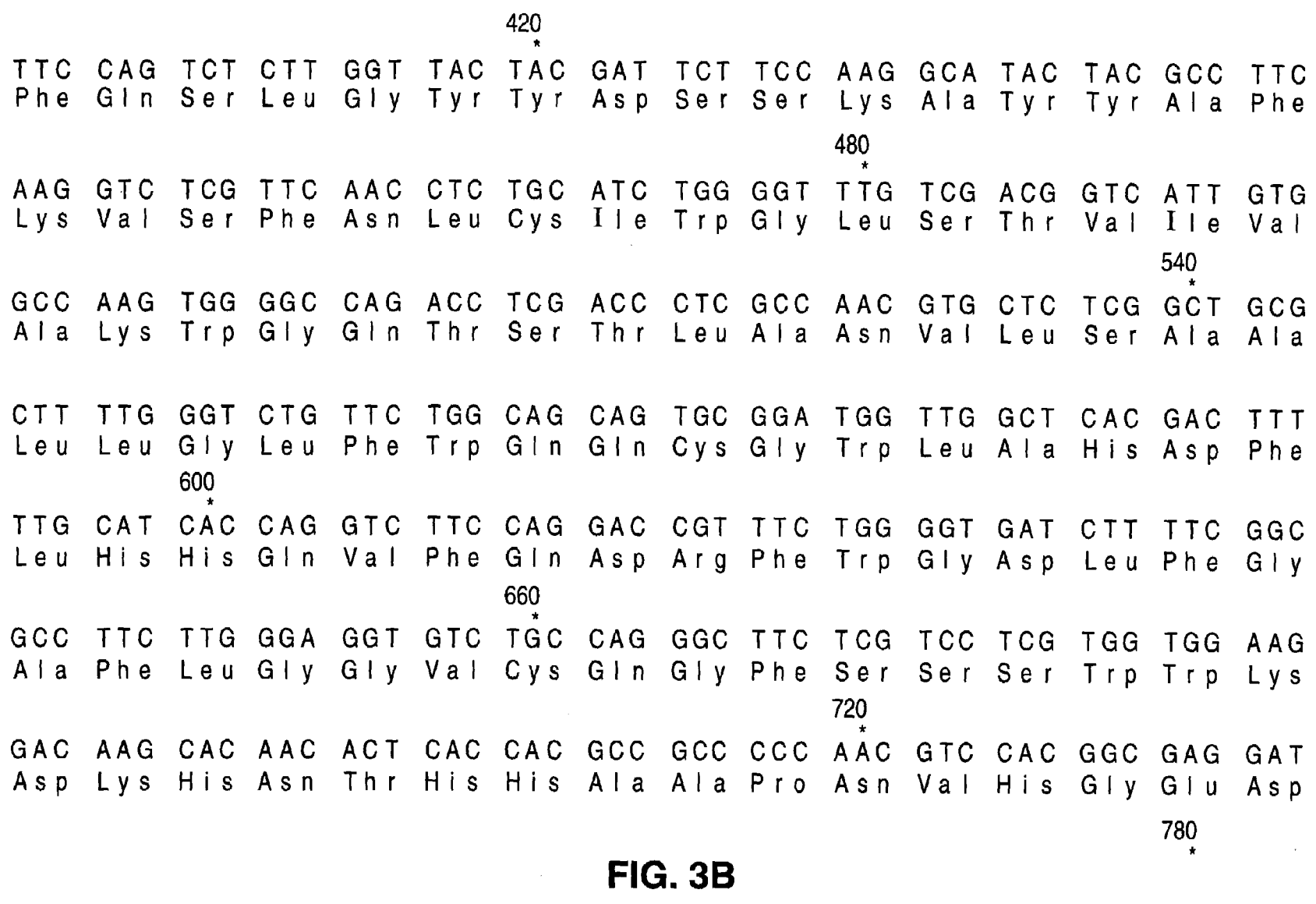

Of particular interest are the *Mortierella alpina* Δ5-desaturase, Δ6-desaturase and Δ12-desaturase. The Δ5-desaturase has 446 amino acids; the amino acid sequence is shown in FIG. 7. The gene encoding the *Mortierella alpina* Δ5-desaturase can be expressed in transgenic microorganisms to effect greater synthesis of ARA from DGLA. Other DNAs which are substantially identical in sequence to the *Mortierella alpina* Δ5-desaturase DNA, or which encode polypeptides which are substantially identical in sequence to the *Mortierella alpina* Δ5-desaturase polypeptide, also can be used. The *Mortierella alpina* Δ6-desaturase, has 457 amino acids and a predicted molecular weight of 51.8 kD; the amino acid sequence is shown in FIG. 3.

The gene encoding the *Mortierella alpina* Δ6-desaturase can be expressed in transgenic plants or animals to effect greater synthesis of GLA from linoleic acid or of stearidonic acid (SDA) from ALA. Other DNAs which are substantially identical in sequence to the *Mortierella alpina* Δ6-desaturase DNA, or which encode polypeptides which are substantially identical in sequence to the *Mortierella alpina* Δ6-desaturase polypeptide, also can be used.

The *Mortierella alpina* Δ12-desaturase has the amino acid sequence shown in FIG. 5. The gene encoding the *Mortierella alpina* Δ12-desaturase can be expressed in transgenic plants to effect greater synthesis of LA from oleic acid. Other DNAs which are substantially identical to the *Mortierella alpina* Δ12-desaturase DNA, or which encode polypeptides which are substantially identical to the *Mortierella alpina* Δ12-desaturase polypeptide, also can be used.

By substantially identical is intended an amino acid sequence or nucleic acid sequence exhibiting in order of increasing preference at least 60%, 80%, 90% or 95% homology to the *Mortierella alpina* Δ5-, Δ6- or Δ12-desaturase amino acid sequence or nucleic acid sequence encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. 157: 105-132, 1982), or on the basis of the ability to assume similar polypeptide secondary structure (Chou and Fasman, Adv. Enzymol. 47: 45-148, 1978).

Other Desaturases

Encompassed by the present invention are related desaturases from the same or other organisms. Such related desaturases include variants of the disclosed 5-, 6- and 12-desaturases that occur naturally within the same or different species of *Mortierella*, as well as homologues of the disclosed 5-, 6- and 12-desaturases from other species and evolutionarily related proteins having desaturase activity. Also included are desaturases which, although not substantially identical to the *Mortierella alpina* [5-] desaturases, desaturate a fatty acid molecule at carbon 5, 6 or 12, respectively, from the carboxyl end of a fatty acid molecule. Related desaturases also can be identified by their ability to function substantially the same as the disclosed desaturases; that is, are still able to effectively convert DGLA to ARA, LA to GLA, ALA to SDA or oleic acid to LA. Related desaturases also can be identified by screening sequence databases for sequences homologous to the disclosed desaturases, by hybridization of a probe based on the disclosed desaturases to a library constructed from the source organism, or by RT-PCR using mRNA from the source organism and primers based on the disclosed desaturase. Such desaturases includes those from humans, *Dictyostelium discoideum* and *Phaeodactylum tricornum*.

The regions of a desaturase polypeptide important for desaturase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis can also be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

Expression of Desaturase Genes

Once the DNA encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is easily harvested, such as seed, leaves, fruits, flowers, roots, etc. Expression can be targeted to that location within the plant by using specific regulatory sequences, such as those of U.S. Pat. No. 5,463,174, U.S. Pat. No. 4,943,674, U.S. Pat. No. 5,106,739, U.S. Pat. No. 5,175,095, U.S. Pat. No. 5,420,034, U.S. Pat. No. 5,188,958, and U.S. Pat. No. 5,589,379. Alternatively, the expressed protein can be an enzyme which produces a product which may be incorporated, either directly or upon further modifications, into a fluid fraction from the host plant. In the present case, expression of desaturase genes, or antisense desaturase transcripts, can alter the levels of specific PUFAs, or derivatives thereof, found in plant parts and/or plant tissues. The Δ5-desaturase polypeptide coding region is expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property.

The choice of a host cell is influenced in part by the desired PUFA profile of the transgenic cell, and the native profile of the host cell. As an example, for production of linoleic acid from oleic acid, the DNA sequence used encodes a polypeptide having Δ12 desaturase activity, and for production of GLA from linoleic acid, the DNA sequence used encodes a polypeptide having Δ6 desaturase activity. Use of a host cell which expresses Δ12 desaturase activity and lacks or is depleted in Δ15 desaturase activity, can be used with an expression cassette which provides for overexpression of Δ6 desaturase alone generally is sufficient to provide for enhanced GLA production in the transgenic cell. Where the host cell expresses Δ9 desaturase activity, expression of both a Δ12- and a Δ6-desaturase can provide for enhanced GLA production. In particular instances where expression of Δ6 desaturase activity is coupled with expression of Δ12 desaturase activity, it is desirable that the host cell naturally have, or be mutated to have, low Δ15 desaturase activity. Alternatively, a host cell for Δ6 desaturase expression may have, or be mutated to have, high Δ12 desaturase activity.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source plant is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. No. 4,910,141 and U.S. Pat. No. 5,500,365.)

When it is desirable to express more than one different gene, appropriate regulatory regions and expression methods, introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by standard techniques. These techniques include transfection, infection, bolistic impact, electroporation, microinjection, scraping, or any other method which introduces the gene of interest into the host cell (see U.S. Pat. No. 4,743,548, U.S. Pat. No. 4,795,855, U.S. Pat. No. 5,068,193, U.S. Pat. No. 5,188,958, U.S. Pat. No. 5,463,174, U.S. Pat. No. 5,565,346 and U.S. Pat. No. 5,565,347). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of interest (see U.S. Pat. No. 5,034,322). Selection of a transformed host can also occur when the expressed marker protein can be detected, either directly or indirectly. The marker protein may be expressed alone or as a fusion to another protein. The marker protein can be detected by its enzymatic activity; for example β galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions may be found in the host plant tissue and/or plant part as free fatty acids or in conjugated forms such as acylglycerols, phospholipids, sulfolipids or glycolipids, and may be extracted from the host cell through a variety of means well-known in the art. Such means may include extraction with organic solvents, sonication, supercritical fluid extraction using for example carbon dioxide, and physical means such as presses, or combinations thereof. Of particular interest is extraction with hexane or methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

Purification of Fatty Acids

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing ARA, DHA and EPA is accomplished by treatment with urea and/or fractional distillation.

Uses of Fatty Acids

The uses of the fatty acids of subject invention are several. Probes based on the DNAs of the present invention may find use in methods for isolating related molecules or in methods to detect organisms expressing desaturases. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

PUFAs of the subject invention produced by recombinant means find applications in a wide variety of areas. Supplementation of humans or animals with PUFAs in various forms can result in increased levels not only of the added PUFAs, but of their metabolic progeny as well. For example, where the inherent Δ6-desaturase pathway is dysfunctional in an individual, treatment with GLA can result not only in increased levels of GLA, but also of downstream products such as ARA and prostaglandins (see FIG. 1). Complex regulatory mechanisms can make it desirable to combine various PUFAs, or to add different conjugates of PUFAs, in order to prevent, control or overcome such mechanisms to achieve the desired levels of specific PUFAs in an individual.

PUFAs, or derivatives thereof, made by the disclosed method can be used as dietary supplements, particularly in infant formulas, for patients undergoing intravenous feeding or for preventing or treating malnutrition. Particular fatty acids such as EPA are used to alter the composition of infant formulas to better replicate the PUFA composition of human breast milk. The predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. A preferred ratio of GLA:DGLA:ARA in infant formulas is from about 1:1:4 to about 1:1:1, respectively. Amounts of oils providing these ratios of PUFA can be determined without undue experimentation by one of skill in the art. PUFAs, or host cells containing them, also can be used as animal food supplements to alter an animal's tissue or milk fatty acid composition to one more desirable for human or animal consumption.

Nutritional Compositions

The present invention also includes nutritional compositions. Such compositions, for purposes of the present invention, include any food or preparation for human consumption including for enteral or parenteral consumption, which when taken into the body (a) serve to nourish or build up tissues or supply energy anti/or (b) maintain, restore or support adequate nutritional status or metabolic function.

The nutritional composition of the present invention comprises at least one oil or acid produced in accordance with the present invention and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will of semi-purified or purified origin. By semi-purified or purified is meant a material which has been prepared by purification of a natural material or by synthesis.

Examples of nutritional compositions of the present invention include but are not limited to infant formulas, dietary supplements, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

Nutritional Compositions

A typical nutritional composition of the present invention will contain edible macronutrients, vitamins and minerals in amounts desired for a particular use. The amounts of such ingredients will vary depending on whether the formulation is intended for use with normal, healthy individuals temporarily exposed to stress, or to subjects having specialized needs due to certain chronic or acute disease states (e.g., metabolic disorders). It will be understood by persons skilled in the art that the components utilized in a nutritional formulation of the present invention are of semi-purified or purified origin. By semi-purified or purified is meant a material that has been prepared by purification of a natural material or by synthesis. These techniques are well known in the art (See, e.g., Code of Federal Regulations for Food Ingredients and Food Processing; Recommended Dietary Allowances, $10^{th}$ Ed., National Academy Press, Washington, D.C., 1989).

In a preferred embodiment, a nutritional formulation of the present invention is an enteral nutritional product, more preferably an adult or child enteral nutritional product. Accordingly in a further aspect of the invention, a nutritional formulation is provided that is suitable for feeding adults or children who are experiencing stress. The formula comprises, in addition to the PUFAs of the invention; macronutrients, vitamins and minerals in amounts designed to provide the daily nutritional requirements of adults.

The macronutritional components include edible fats, carbohydrates and proteins. Exemplary edible fats are coconut oil, soy oil, and mono- and diglycerides and the PUFA oils of this invention. Exemplary carbohydrates are glucose, edible lactose and hydrolyzed cornstarch. A typical protein source would be soy protein, electrodialysed whey or electrodialysed skim milk or milk whey, or the hydrolysates of these proteins, although other protein sources are also available and may be used. These macronutrients would be added in the form of commonly accepted nutritional compounds in amount equivalent to those present in human milk or an energy basis, i.e., on a per calorie basis.

Methods for formulating liquid and enteral nutritional formulas are well known in the art and are described in detail in the examples.

The enteral formula can be sterilized and subsequently utilized on a ready-to-feed (RTF) basis or stored in a concentrated liquid or a powder. The powder can be prepared by spray drying the enteral formula prepared as indicated above, and the formula can be reconstituted by rehydrating the concentrate. Adult and infant nutritional formulas are well known in the art and commercially available (e.g., SIMILAC® nutritional product, ENSURE® liquid nutritive preparation, JEVITY® liquid nutritive preparation and ALIMENTUM® infant formula from Ross Products Division, Abbott Laboratories). An oil or acid of the present invention can be added to any of these formulas in the amounts described below.

The energy density of the nutritional composition when in liquid form, can typically range from about 0.6 Kcal to 3 Kcal per ml. When in solid or powdered form, the nutritional supplement can contain from about 1.2 to more than 9 Kcals per gm, preferably 3 to 7 Kcals per gm. In general, the osmolality of a liquid product should be less than 700 mOsm and more preferably less than 660 mOsm.

The nutritional formula would typically include vitamins and minerals, in addition to the PUFAs of the invention, in order to help the individual ingest the minimum daily requirements for these substances. In addition to the PUFAs listed above, it may also be desirable to supplement the nutritional composition with zinc, copper, and folic acid in addition to antioxidants. It is believed that these substances will also provide a boost to the stressed immune system and thus will provide further benefits to the individual. The presence of zinc, copper or folic acid is optional and is not required in order to gain the beneficial effects on immune suppression. Likewise a pharmaceutical composition can be supplemented with these same substances as well.

In a more preferred embodiment, the nutritional contains, in addition to the antioxidant system and the PUFA component, a source of carbohydrate wherein at least 5 weight % of said carbohydrate is an indigestible oligosaccharide. In yet a more preferred embodiment, the nutritional composition additionally contains protein, taurine and carnitine.

The PUFAs, or derivatives thereof, made by the disclosed method can be used as dietary substitutes, or supplements, particularly infant formulas, for patients undergoing intravenous feeding or for preventing or treating malnutrition. Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. Additionally, the predominant triglyceride in human milk has been reported to be 1,3-di-oleoyl-2-palmitoyl, with 2-palmitoyl glycerides reported as better absorbed than 2-oleoyl or 2-lineoyl glycerides (U.S. Pat. No. 4,876,107). Thus, fatty acids such as ARA, DGLA, GLA and/or EPA produced by the invention can be used to alter the composition of infant formulas to better replicate the PUFA composition of human breast milk. In particular, an oil composition for use in a pharmacologic or food supplement, particularly a breast milk substitute or supplement, will preferably comprise one or more of ARA, DGLA and GLA. More preferably the oil will comprise from about 0.3 to 30% ARA, from about 0.2 to 30% DGLA, and from about 0.2 to about 30% GLA.

In addition to the concentration, the ratios of ARA, DGLA and GLA can be adapted for a particular given end use. When formulated as a breast milk supplement or substitute, an oil composition which contains two or more of ARA, DGLA and GLA will be provided in a ratio of about 1:19:30 to about 6:1:0.2, respectively. For example, the breast milk of animals can vary in ratios of ARA:DGLA:DGL ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of desaturase expression as described can be used to modulate the PUFA levels and ratios. Depending on the expression system used, e.g., cell culture or an animal expressing oil(s) in its milk, the oils also can be isolated and recombined in the desired concentrations and ratios. Amounts of oils providing these ratios of PUFA can be determined following standard protocols. PUFAs, or host cells containing them, also can be used as animal food supplements to alter an animal's tissue or milk fatty acid composition to one more desirable for human or animal consumption.

For dietary supplementation, the purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

Pharmaceutical Compositions

The present invention also encompasses a pharmaceutical composition comprising one or more of the acids and/or resulting oils produced in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream.

Possible routes of administration include, for example, oral, rectal and parenteral. The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

Additionally, the composition of the present invention may be utilized for cosmetic purposes. It may be added to preexisting cosmetic compositions such that a mixture is formed or may be used as a sole composition.

Pharmaceutical compositions may be utilized to administer the PUFA component to an individual. Suitable pharmaceutical compositions may comprise physiologically acceptable sterile aqueous or non-aqueous solutions, dispersions, suspensions or emulsions and sterile powders for reconstitution into sterile solutions or dispersions for ingestion. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances, and the like.

Solid dosage forms such as tablets and capsules can be prepared using techniques well known in the art. For example, PUFAs of the invention can be tabletted with conventional tablet bases such as lactose, sucrose, and cornstarch in combination with binders such as acacia, cornstarch or gelatin, disintegrating agents such as potato starch or alginic acid and a lubricant such as stearic acid or magnesium stearate. Capsules can be prepared by incorporating these excipients into a gelatin capsule along with the antioxidants and the PUFA component. The amount of the antioxidants and PUFA component that should be incorporated into the pharmaceutical formulation should fit within the guidelines discussed above.

As used in this application, the term "treat" refers to either preventing, or reducing the incidence of, the undesired occurrence. For example, to treat immune suppression refers to either preventing the occurrence of this suppression or reducing the amount of such suppression. The terms "patient" and "individual" are being used interchangeably and both refer to an animal. The term "animal" as used in this application refers to any warm-blooded mammal including, but not limited to, dogs, humans, monkeys, and apes. As used in the application the term "about" refers to an amount varying from the stated range or number by a reasonable amount depending upon the context of use. Any numerical number or range specified in the specification should be considered to be modified by the term about.

"Dose" and "serving" are used interchangeably and refer to the amount of the nutritional or pharmaceutical composition ingested by the patient in a single setting and designed to deliver effective amounts of the antioxidants and the structured triglyceride. As will be readily apparent to those skilled in the art, a single dose or serving of the liquid nutritional powder should supply the amount of antioxidants and PUFAs discussed above. The amount of the dose or serving should be a volume that a typical adult can consume in one sitting. This amount can vary widely depending upon the age, weight, sex or medical condition of the patient. However as a general guideline, a single serving or dose of a liquid nutritional produce should be considered as encompassing a volume from 100 to 600 ml, more preferably from 125 to 500 ml and most preferably from 125 to 300 ml.

The PUFAs of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

Pharmaceutical Applications

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. The PUFAs of the present invention may be administered alone or in combination with a pharmaceutically acceptable carrier or excipient. Where available, gelatin capsules are the preferred form of oral administration. Dietary supplementation as set forth above also can provide an oral route of administration. The unsaturated acids of the present invention may be administered in conjugated forms, or as salts, esters, amides or pro-drugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids. The typical normal adult plasma fatty acid profile comprises 6.64 to 9.46% of ARA, 1.45 to 3.11% of DGLA, and 0.02 to 0.08% of GLA. These PUFAs or their metabolic precursors can be administered, either alone or in mixtures with other PUFAs, to achieve a normal fatty acid profile in a patient. Where desired, the individual components of formulations may be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention; preferred is a composition having from about 1 to about 25 weight percent of the total PUFA composition as GLA (U.S. Pat. No. 5,196,198). Other vitamins, and particularly fat-soluble vitamins such as vitamin A, D, E and L-carnitine can optionally be included. Where desired, a preservative such as α tocopherol may be added, typically at about 0.1% by weight.

Suitable pharmaceutical compositions may comprise physiologically acceptable sterile aqueous or non-aqueous solutions, dispersions, suspensions or emulsions and sterile powders for reconstitution into sterile injectable solutions or dispersions. Examples of suitable aqueous and non-aqeuous carriers, diluents, solvents or vehicles include water, ethanol, polyols (propylleneglyol, polyethylenegycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances and the like.

An especially preferred pharmaceutical composition contains diacetyltartaric acid esters of mono- and diglycerides dissolved in an aqueous medium or solvent. Diacetyltartaric acid esters of mono- and diglycerides have an HLB value of about 9-12 and are significantly more hydrophilic than existing antimicrobial lipids that have HLB values of 2-4. Those existing hydrophobic lipids cannot be formulated into aqueous compositions. As disclosed herein, those lipids can now be solubilized into aqueous media in combination with diacetyltartaric acid esters of mono- and diglycerides. In accordance with this embodiment, diacetyltartaric acid esters of mono- and diglycerides (e.g., DATEM-C12:0) is melted with other active antimicrobial lipids (e.g., 18:2 and 12:0 monoglycerides) and mixed to obtain a homogeneous mixture. Homogeneity allows for increased antimicrobial activity. The mixture can be completely dispersed in water. This is not possible without the addition of diacetyltartaric acid esters of mono- and diglycerides and premixing with other monoglycerides prior to introduction into water. The aqueous composition can then be admixed under sterile conditions with physiologically acceptable diluents, preservatives, buffers or propellants as may be required to form a spray or inhalant.

The present invention also encompasses the treatment of numerous disorders with fatty acids. Supplementation with PUFAs of the present invention can be used to treat restenosis after angioplasty. Symptoms of inflammation, rheumatoid arthritis, and asthma and psoriasis can be treated with the PUFAs of the present invention. Evidence indicates that PUFAs may be involved in calcium metabolism, suggesting that PUFAs of the present invention may be used in the treatment or prevention of osteoporosis and of kidney or urinary tract stones.

The PUFAs of the present invention can be used in the treatment of cancer. Malignant cells have been shown to have altered fatty acid compositions; addition of fatty acids has been shown to slow their growth and cause cell death, and to increase their susceptibility to chemotherapeutic agents. GLA has been shown to cause reexpression on cancer cells of the E-cadherin cellular adhesion molecules, loss of which is associated with aggressive metastasis. Clinical testing of intravenous administration of the water soluble lithium salt of GLA to pancreatic cancer patients produced statistically significant increases in their survival. PUFA supplementation may also be useful for treating cachexia associated with cancer.

The PUFAs of the present invention can also be used to treat diabetes (U.S. Pat. No. 4,826,877; Horrobin et al., Am. J. Clin. Nutr. Vol. 57 (Suppl.), 732S-737S). Altered fatty acid metabolism and composition has been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage.

The PUFAs of the present invention can be used to treat eczema, reduce blood pressure and improve math scores. Essential fatty acid deficiency has been suggested as being involved in eczema, and studies have shown beneficial effects on eczema from treatment with GLA. GLA has also been shown to reduce increases in blood pressure associated with stress, and to improve performance on arithmetic tests. GLA and DGLA have been shown to inhibit platelet aggregation, cause vasodilation, lower cholesterol levels and inhibit proliferation of vessel wall smooth muscle and fibrous tissue (Brenner et al., Adv. Exp. Med. Biol. Vol. 83, p. 85-101, 1976). Administration of GLA or DGLA, alone or in combination with EPA, has been shown to reduce or prevent gastrointestinal bleeding and other side effects caused by non-steroidal anti-inflammatory drugs (U.S. Pat. No. 4,666,701). GLA and DGLA have also been shown to prevent or treat endometriosis and premenstrual syndrome (U.S. Pat. No. 4,758,592) and to treat myalgic encephalomyelitis and chronic fatigue after viral infections (U.S. Pat. No. 5,116,871).

Further uses of the PUFAs of this invention include use in treatment of AIDS, multiple schlerosis, acute respiratory syndrome, hypertension and inflammatory skin disorders. The PUFAs of the inventions also can be used for formulas for general health as well as for geriatric treatments.

Veterinary Applications

It should be noted that the above-described pharmaceutical and nutritional compositions may be utilized in connection with animals, as well as humans, as animals experience many of the same needs and conditions as human. For example, the oil or acids of the present invention may be utilized in animal feed supplements or as animal feed substitutes.

The following examples are presented by way of illustration, not of limitation.

EXAMPLES

Example 1 Isolation of Δ5 Desaturase Nucleotide Sequence from *Mortierella alpina*

Example 2 Isolation of Δ6 Desaturase Nucleotide Sequence from *Mortierella alpina*

Example 3 Identification of Δ6 Desaturases Homologues to the *Mortierella alpina* Δ Desaturase Example 4 Isolation of D-12 Desaturase Nucleotide Sequence from *Mortierella alpina*

Example 5 Isolation of Cytochrome b5 Reductase Nucleotide Sequence from *Mortierella alpina*

Example 6 Expression of *M. alpina* Desaturase Clones in Baker's Yeast

Example 7 Fatty Acid Analysis of Leaves from Ma29 Transgenic *Brassica* Plants

Example 8 Expression of *M. alpina* Δ6 Desaturase in *Brassica napus*

Example 9 Expression of *M. alpina* Δ12 desaturase in *Brassica napus*

Example 10 Simultaneous expression of *M. alpina* Δ6 and Δ12 desaturases in *Brassica napus*

Example 11 Simultaneous expression of *M. alpina* Δ5 and Δ6 desaturases in *Brassica napus*

Example 12 Simultaneous expression of *M. alpina* Δ5, Δ6 and Δ12 desaturases in *Brassica napus*

Example 13 Stereospecific Distribution of Δ6-Desaturated Oils

Example 14 Fatty Acid Compositions of Transgenic Plants

Example 15 Combined Expression of Δ6 and Δ12 Desaturases in *B. napus* Achieved by Crossing Example 16 Expression of *M. alpina* desaturases in soybean Example 17 Human Desaturase Gene Sequences Example 1

Isolation of a Δ5-Desaturase Nucleotide Sequence from *Mortierella alpina*

*Mortierella alpina* produces arachidonic acid (ARA, 20:4) from the precursor 20:3 by a Δ5-desaturase. A nucleotide sequence encoding the Δ5-desaturase from *Mortierella alpina* (see FIG. 7) was obtained through PCR amplification using *M. alpina* $1^{st}$ strand cDNA and degenerate oligonucleotide primers corresponding to amino acid sequences conserved between Δ6-desaturases from *Synechocystis* and *Spirulina*. The procedure used was as follows:

Total RNA was isolated from a 3 day old PUFA-producing culture of *Mortierella alpina* using the protocol of Hoge et al. (1982) *Experimental Mycology* 6:225-232. The RNA was used to prepare double-stranded cDNA using BRL's lambda-ZipLox system, following the manufacturer's instructions. Several size fractions of the *M. alpina* cDNA were packaged separately to yield libraries with different average-sized inserts. The "full-length" library contains approximately $3 \times 10^6$ clones with an average insert size of 1.77 kb. The "sequencing-grade" library contains approximately $6 \times 10^5$ clones with an average insert size of 1.1 kb.

5 μg of total RNA was reverse transcribed using BRL Superscript RTase and the primer TSyn 5'-CAAGCTTCTG- CAGGAGCTCTTTTTTTTTTTTTTT-3' (SEQ ID NO:19.) Degenerate oligonucleotides were designed to regions conserved between the two cyanobacterial Δ6-desaturase sequences. The specific primers used were:

D6DESAT-F3 (SEQ ID NO:20) 5'-CUACUACUACUACAY-CAYACOTAYACOAAYAT-3'

Figure 4B:
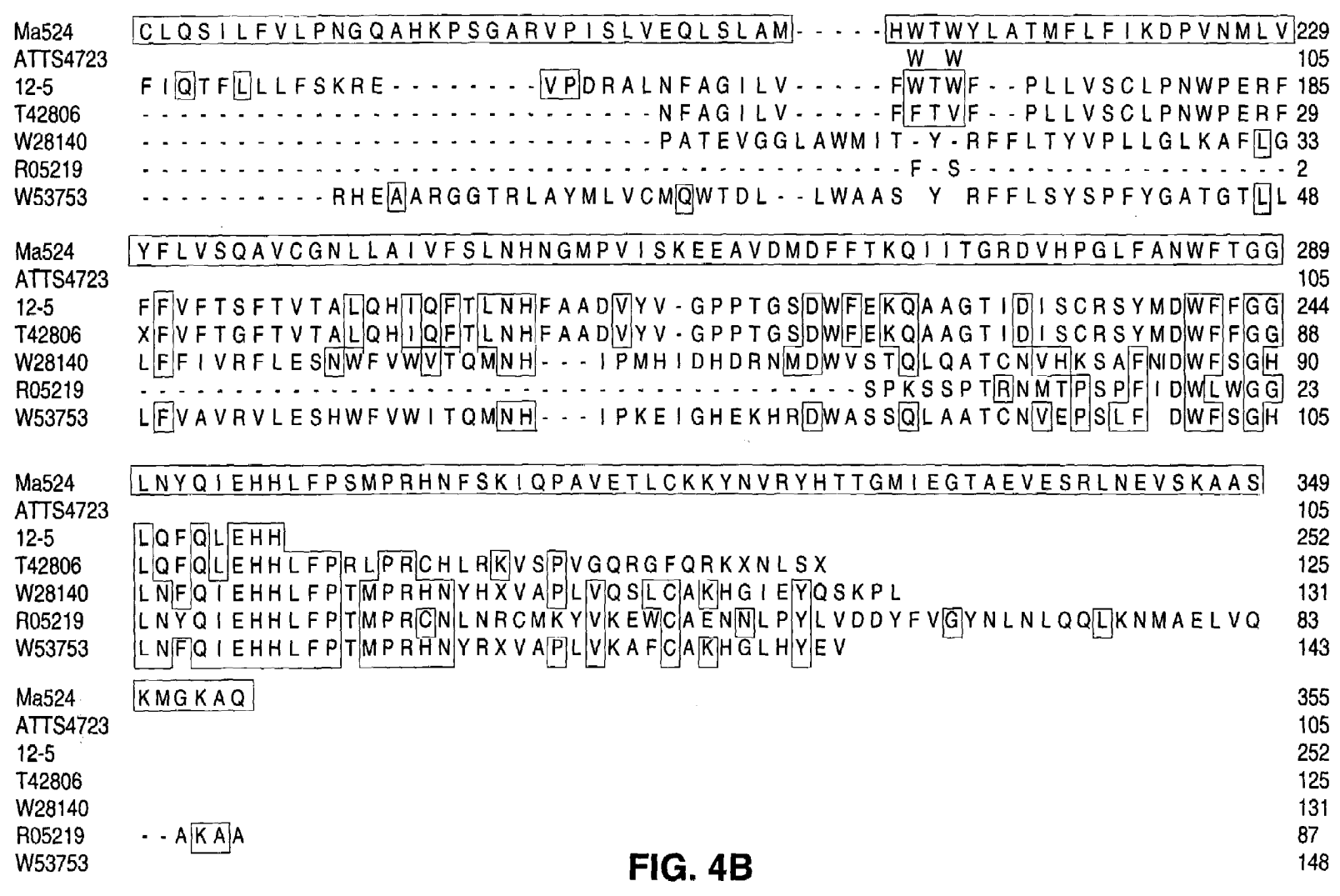

D6DESAT-R3 (SEQ ID NO:21) 5'-CAUCAUCAUCAUOG-GRAAOARRTGRTG-3' where Y=C+T, R=A+G, and O=I+C. PCR amplification was carried out in a 25 μl volume containing: template derived from 40 ng total RNA, 2 pM each primer, 200 μM each deoxyribonucleotide triphosphate, 60 mM Tris-Cl, pH 8.5, 15 mM (NH$_4$)$_2$SO$_4$, 2 mM MgCl$_2$. Samples were subjected to an initial desaturation step of 95 degrees (all temperatures Celsius) for 5 minutes, then held at 72 degrees while 0.2 U of Taq polymerase were added. PCR thermocycling conditions were as follows: 94 degrees for 1 min., 45 degrees for 1.5 min., 72 degrees for 2 min. PCR was continued for 35 cycles. PCR using these primers on the M. alpina first-strand cDNA produced a 550 by reaction product. Comparison of the deduced amino acid sequence of the M. alpina PCR fragment revealed regions of homology with Δ6-desaturases (see FIG. 4). However, there was only about 28% identity over the region compared. The deduced amino acid sequence is presented in SEQ ID NO:14.

The PCR product was used as a probe to isolate corresponding cDNA clones from a M. alpina library. The longest cDNA clone, Ma29, was designated pCGN5521 and has been completely sequenced on both strands. The cDNA is contained as a 1481 by insert in the vector pZL1 (Bethesda Research Laboratories) and, beginning with the first ATG, contains an open reading frame encoding 446 amino acids. The reading frame contains the sequence deduced from the PCR fragment. The sequence of the cDNA insert was found to contain regions of homology to Δ6-desaturases (see FIG. 8). For example, three conserved "histidine boxes" (that have been observed in other membrane-bound desaturases (Okuley et al., (1994) *The Plant Cell* 6:147-158)) were found to be present in the *Mortierella* sequence at amino acid positions 171-175, 207-212, and 387-391 (see FIGS. 5A-5D). However, the typical "HXXHH" amino acid motif for the third histidine box for the *Mortierella* desaturase was found to be QXXHH. The amino-terminus of the encoded protein, showed significant homology to cytochrome b5 proteins. Thus, the *Mortierella* cDNA clone appears to represent a fusion between a cytochrome b5 and a fatty acid desaturase. Since cytochrome b5 is believed to function as the electron donor for membrane-bound desaturase enzymes, it is possible that the N-terminal cytochrome b5 domain of this desaturase protein is involved in its function. This may be advantageous when expressing the desaturase in heterologous systems for PUFA production.

Example 2

Isolation of Δ6 Desaturase Nucleotide Sequence from *Mortierella alpina*

A nucleic acid sequence from a partial cDNA clone, Ma524, encoding a Δ6 fatty acid desaturase from *Mortierella alpina* was obtained by random sequencing of clones from the *M. alpina* cDNA library described in Example 1. cDNA-containing plasmids were excised as follows:

Five μl of phage were combined with 100 μl of *E. coli* DH10B(ZIP) grown in ECLB plus 10 μg/ml kanamycin, 0.2% maltose, and 10 mM MgSO$_4$ and incubated at 37 degrees for 15 minutes. 0.9 ml SOC was added and 100 μl of the bacteria immediately plated on each of 10 ECLB+50 μg Pen plates. No 45 minute recovery time was needed. The plates were incubated overnight at 37 degrees. Colonies were picked into ECLB+50 μg Pen media for overnight cultures to be used for making glycerol stocks and miniprep DNA. An aliquot of the culture used for the miniprep is stored as a glycerol stock. Plating on ECLB+50 μg Pen/ml resulted in more colonies and a greater proportion of colonies containing inserts than plating on 100 μg/ml Pen.

Random colonies were picked and plasmid DNA purified using Qiagen miniprep kits. DNA sequence was obtained from the 5' end of the cDNA insert and compared to the databases using the BLAST algorithm. Ma524 was identified as a putative Δ6 desaturase based on DNA sequence homology to previously identified Δ6 desaturases. A full-length cDNA clone was isolated from the *M. alpina* library. The abundance of this clone appears to be slightly (2x) less than Ma29. Ma524 displays significant homology to a portion of a *Caenorhabditis elegans* cosmid, WO6D2.4, a cytochrome b5/desaturase fusion protein from sunflower, and the two Δ6 desaturases in the public databanks those from *Synechocystis* and *Spirulina*.

In addition, Ma524 shows significant homology to the borage Δ6-desaturase sequence (PCT publication WO 96/21022). Ma524 thus appears to encode a Δ6-desaturase that is related to the borage and algal Δ6-desaturases. It should be noted that, although the amino acid sequences of Ma524 and the borage Δ6 are similar, the base composition of the cDNAs is quite different: the borage cDNA has an overall base composition of 60% A+T, with some regions exceeding 70%, while Ma524 has an average of 44% A+T base composition, with no regions exceeding 60%. This may have implications for expressing the cDNAs in microorganisms or animals which favor different base compositions. It is known that poor expression of recombinant genes can occur when the host has a very different base composition from that of the introduced gene. Speculated mechanisms for such poor expression include decreased stability or translatability of the mRNA.

Example 3

Identification of Δ6-Desaturases Homologous to the *Mortierella alpina* Δ6-Desaturase Nucleic acid sequences that encode putative Δ6-desaturases were identified through a BLASTX search of the est databases through NCBI using the Ma524 amino acid sequence. Several sequences showed significant homology. In particular, the deduced amino acid sequence of two *Arabidopsis thaliana* sequences, (accession numbers F13728 and T42806) showed homology to two different regions of the deduced amino acid sequence of Ma524. The following PCR primers were designed: ATTS4723-FOR (complementary to F13728) 5'-CUACUACUACUAGGAGTCCTCTA CGGT-GTTTTG, SEQ ID NO:22, and T42806-REV (complementary to T42806) 5' CAUCAUCAUCAUATGATGCT-CAAGCTGAAACTG, SEQ ID NO:23. Five μg of total RNA isolated from developing siliques of *Arabidopsis thaliana* was reverse transcribed using BRL Superscript RTase and the primer TSyn 5'CCAAGCTTCTGCAG-GAGCTCTTTTTTTTTTTTTTT-3', (SEQ ID NO:24). PCR was carried out in a 50 ul volume containing: template derived from 25 ng total RNA, 2 pM each primer, 200 μM each deoxyribonucleotide triphosphate, 60 mM Tris-Cl, pH 8.5, 15 mM $(NH_4)_2SO_4$, 2 mM $MgCl_2$, 0.2 U Taq Polymerase. Cycle conditions were as follows: 94 degrees for 30 sec., 50 degrees for 30 sec., 72 degrees for 30 sec. PCR was continued for 35 cycles followed by an additional extension at 72 degrees for 7 minutes. PCR resulted in a fragment of ~750 base pairs which was subsequently subcloned, named 12-5, and sequenced. Each end of this fragment corresponds to the *Arabidopsis* est from which the PCR primers were derived. This is the sequence named 12-5. The deduced amino acid sequence of 12-5 is compared to that of Ma524 and ests from human (W28140), mouse (W53753), and *C. elegans* (R05219) in FIG. 4. Based on homology, these sequences represent desaturase polypeptides. The full-length genes can be cloned using probes based on the est sequences. The genes can then be placed in expression vectors and expressed in host cells and their specific Δ6- or other desaturase activity can be determined as described below.

Example 4

Isolation of Δ-12 Desaturase Nucleotide Sequence from *Mortierella alpina*

Based on the fatty acids it accumulates, *Mortierella alpina* has an ω6 type desaturase. The ω6 desaturase is responsible for the production of linoleic acid (18:2) from oleic acid (18:1). Linoleic acid (18:2) is a substrate for a Δ6 desaturase. This experiment was designed to determine if *Mortierella alpina* has a Δ12-desaturase polypeptide, and if so, to identify the corresponding nucleotide sequence. A random colony from the *M. alpina* sequencing grade library, Ma648, was sequenced and identified as a putative desaturase based on DNA sequence homology to previously identified desaturases, as described for Ma524 (see Example 2). The deduced amino acid sequence from the 5' end of the Ma648 cDNA displays significant homology to soybean microsomal (ω6 (Δ12) desaturase (accession #L43921) as well as castor bean oleate 12-hydroxylase (accession #U22378). In addition, homology is observed to a variety of other ω6 (Δ12) and ω3 (Δ15) fatty acid desaturase sequences.

Example 5

Isolation of Cytochrome b5 Reductase Nucleotide Sequence from *Mortierella alpina*

A nucleic acid sequence encoding a cytochrome b5 reductase from *Mortierella alpina* was obtained as follows. A cDNA library was constructed based on total RNA isolated from *Mortierella alpina* as described in Example 1. DNA sequence was obtained from the 5' and 3' ends of one of the clones, M12-27. A search of public databanks with the deduced amino acid sequence of the 3' end of M12-27 (see FIG. 5) revealed significant homology to known cytochrome b5 reductase sequences. Specifically, over a 49 amino acid region, the *Mortierella* clone shares 55% identity (73% homology) with a cytochrome b5 reductase from pig (see FIG. 4).

Example 6

Expression of *M. alpina* Desaturase Clones in Baker's Yeast Yeast Transformation Lithium acetate transformation of yeast was performed according to standard protocols (*Methods in Enzymology*, Vol. 194, p. 186-187, 1991). Briefly, yeast were grown in YPD at 30° C. Cells were spun down, resuspended in TE, spun down again, resuspended in TE containing 100 mM lithium acetate, spun down again, and resuspended in TE/lithium acetate. The resuspended yeast were incubated at 30° C. for 60 minutes with shaking. Carrier DNA was added, and the yeast were aliquoted into tubes. Transforming DNA was added, and the tubes were incubated for 30 min. at 30° C. PEG solution (35% (w/v) PEG 4000, 100 mM lithium acetate, TE pH7.5) was added followed by a 50 min. incubation at 30° C. A 5 min. heat shock at 42° C. was performed, the cells were pelleted, washed with TE, pelleted again and resuspended in TE. The resuspended cells were then plated on selective media.

Desaturase Expression in Transformed Yeast cDNA clones from *Mortierella alpina* were screened for desaturase activity in baker's yeast. A canola Δ15-desaturase (obtained by PCR using $1^{st}$ strand cDNA from *Brassica napus* cultivar 212/86 seeds using primers based on the published sequence (Arondel et al. *Science* 258:1353-1355)) was used as a positive control. The Δ15-desaturase gene and the gene from cDNA clone Ma29 was put in the expression vector pYES2 (Invitrogen), resulting in plasmids pCGR-2 and pCGR-4, respectively. These plasmids were transfected into *S. cerevisiae* yeast strain 334 and expressed after induction with galactose and in the presence of substrates that allowed detection of specific desaturase activity. The control strain was *S. cerevisiae* strain 334 containing the unaltered pYES2 vector. The substrates used, the products produced and the indicated desaturase activity were: DGLA (conversion to ARA would indicate Δ5-desaturase activity), linoleic acid (conversion to GLA would indicate Δ6-desaturase activity; conversion to ALA would indicate Δ15-desaturase activity), oleic acid (an endogenous substrate made by *S. cerevisiae*, conversion to linoleic acid would indicate Δ12-desaturase activity, which *S. cerevisiae* lacks), or ARA (conversion to EPA would indicate Δ17-desaturase activity). The results are provided in Table 1 below. The lipid fractions were extracted as follows: Cultures were grown for 48-52 hours at 15° C. Cells were pelleted by centrifugation, washed once with sterile $ddH_2O$, and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5 N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture cooled, 2 ml of water and 1 ml of hexane were added to extract the FAME for analysis by GC. The percent conversion was calculated by dividing the product produced by the sum of (the product produced and the substrate added) and then multiplying by 100. To calculate the oleic acid percent conversion, as no substrate was added, the total linoleic acid produced was divided by the sum of (oleic acid and linoleic acid produced), then multiplying by 100.

TABLE 1

M. alpina Desaturase Expression in Baker's Yeast

| CLONE | TYPE OF ENZYME ACTIVITY | % CONVERSION OF SUBSTRATE | |
|---|---|---|---|
| pCGR-2 | Δ6 | 0 | (18:2 to 18:3ω6) |
| (canola Δ15 | Δ15 | 16.3 | (18:2 to 18:3ω3) |
| desaturase) | Δ5 | 2.0 | (20:3 to 20:4ω6) |
|  | Δ17 | 2.8 | (20:4 to 20:5ω3) |
|  | Δ12 | 1.8 | (18:1 to 18:2ω6) |
| pCGR-4 | Δ6 | 0 | |
| (M. alpina | Δ15 | 0 | |
| Δ6-like, Ma29) | Δ5 | 15.3 | |
|  | Δ17 | 0.3 | |
|  | Δ12 | 3.3 | |
| pCGR-7 | Δ6 | 0 | |
| (M. alpina | Δ15 | 3.8 | |
| Δ12-like, Ma648 | Δ5 | 2.2 | |
|  | Δ17 | 0 | |
|  | Δ12 | 63.4 | |

The Δ15-desaturase control clone exhibited 16.3% conversion of the substrate. The pCGR-4 clone expressing the Ma29 cDNA converted 15.3% of the 20:3 substrate to 20:4w6, indicating that the gene encodes a Δ5-desaturase. The background (non-specific conversion of substrate) was between 0-3% in these cases. The pCGR-5 clone expressing the Ma524 cDNA showed 6% conversion of the substrate to GLA, indicating that the gene encodes a Δ6-desaturase. The pCGR-7 clone expressing the Ma648 cDNA converted 63.4% conversion of the substrate to LA, indicating that the gene encodes a Δ12-desaturase. Substrate inhibition of activity was observed by using different concentrations of the substrate. When substrate was added to 100 μM, the percent conversion to product dropped as compared to when substrate was added to 25 μM (see below). These data show that desaturases with different substrate specificities can be expressed in a heterologous system and used to produce PUFAs.

Table 2 represents fatty acids of interest as a percent of the total lipid extracted from the yeast host S. cerevisiae 334 with the indicated plasmid. No glucose was present in the growth media. Affinity gas chromatography was used to separate the respective lipids. GC/MS was employed to verify the identity of the product(s). The expected product for the B. napus Δ15-desaturase, α-linolenic acid, was detected when its substrate, linoleic acid, was added exogenously to the induced yeast culture. This finding demonstrates that yeast expression of a desaturase gene can produce functional enzyme and detectable amounts of product under the current growth conditions. Both exogenously added substrates were taken up by yeast, although slightly less of the longer chain PUFA, dihomo-γ-linolenic acid (20:3), was incorporated into yeast than linoleic acid (18:2) when either was added in free form to the induced yeast cultures. γ-linolenic acid was detected when linoleic acid was present during induction and expression of S. cerevisiae 334 (pCGR-5). The presence of this PUFA demonstrates Δ6-desaturase activity from pCGR-5 (MA524). Linoleic acid, identified in the extracted lipids from expression of S. cerevisiae 334 (pCGR-7), classifies the cDNA MA648 from M. alpina as the Δ12-desaturase.

TABLE 2

Fatty Acid as a Percentage of Total Lipid Extracted from Yeast

| Plasmid in Yeast (enzyme) | 18:2 Incorporated | α-18:3 Produced | γ-18:3 Produced | 20:3 Incorporated | 20:4 Produced | 18:1* Present | 18:2 Produced |
|---|---|---|---|---|---|---|---|
| pYES2 (control) | 66.9 | 0 | 0 | 58.4 | 0 | 4 | 0 |
| pCGR-2 (Δ15) | 60.1 | 5.7 | 0 | 50.4 | 0 | 0.7 | 0 |
| pCGR-4 (Δ5) | 67 | 0 | 0 | 32.3 | 5.8 | 0.8 | 0 |
| pCGR-5 (Δ6) | 62.4 | 0 | 4.0 | 49.9 | 0 | 2.4 | 0 |
| pCGR-7 (Δ12) | 65.6 | 0 | 0 | 45.7 | 0 | 7.1 | 12.2 |

100 μM substrate added

*18:1 is an endogenous fatty acid in yeast

Key To Tables

18:1 = oleic acid

18:2 = linoleic acid

α-18:3 = α-linolenic acid

γ-18:3 = γ-linolenic acid

18:4 = stearidonic acid

20:3 = dihomo-γ-linolenic acid

20:4 = arachidonic acid

Example 7

Expression of Δ5 Desaturase in Plants

Expression in Leaves

This experiment was designed to determine whether leaves expressing Ma29 (as determined by Northern) were able to convert exogenously applied DGLA (20:3) to ARA (20:4).

The Ma29 desaturase cDNA was modified by PCR to introduce convenient restriction sites for cloning. The desaturase coding region has been inserted into a d35 cassette under the control of the double 35S promoter for expression in *Brassica* leaves (pCGN5525) following standard protocols (see U.S. Pat. No. 5,424,200 and U.S. Pat. No. 5,106,739). Transgenic *Brassica* plants containing pCGN5525 were generated following standard protocols (see U.S. Pat. No. 5,188,958 and U.S. Pat. No. 5,463,174).

In the first experiment, three plants were used: a control, LPOO4-1, and two transgenics, 5525-23 and 5525-29. LP004 is a low-linolenic *Brassica* variety. Leaves of each were selected for one of three treatments: water, GLA or DGLA. GLA and DGLA were purchased as sodium salts from NuChek Prep and dissolved in water at 1 mg/ml. Aliquots were capped under $N_2$ and stored at −70 degrees C. Leaves were treated by applying a 50 μl A drop to the upper surface and gently spreading with a gloved finger to cover the entire surface. Applications were made approximately 30 minutes before the end of the light cycle to minimize any photo-oxidation of the applied fatty acids. After 6 days of treatment one leaf from each treatment was harvested and cut in half through the mid rib. One half was washed with water to attempt to remove unincorporated fatty acid. Leaf samples were lyophilized overnight, and fatty acid composition determined by gas chromatography (GC). The results are shown in Table 3.

TABLE 3

Fatty Acid Analysis of Leaves from Ma29 Transgenic *Brassica* Plants

| Treatment | SPL # | 16:00 % | 16:01 % | 18:00 % | 18:01 % | 18:1o % | 18:1v % | 18:02 % | 18:3g % | 18:03 % | 18:04 % | 20:00 % | 20:01 % |
|---|---|---|---|---|---|---|---|---|---|---|---|---|---|
| Water | 33 | 12.95 | 0.08 | 2.63 | 2.51 | 1.54 | 0.98 | 16.76 | 0 | 45.52 | 0 | 0.09 | 0 |
|  | 34 | 13.00 | 0.09 | 2.67 | 2.56 | 1.55 | 1.00 | 16.86 | 0 | 44.59 | 0 | 0.15 | 0 |
|  | 35 | 14.13 | 0.09 | 2.37 | 2.15 | 1.27 | 0.87 | 16.71 | 0 | 49.91 | 0 | 0.05 | 0.01 |
|  | 36 | 13.92 | 0.08 | 2.32 | 2.07 | 1.21 | 0.86 | 16.16 | 0 | 50.25 | 0 | 0.05 | 0 |
|  | 37 | 13.79 | 0.11 | 2.10 | 2.12 | 1.26 | 0.86 | 15.90 | 0.08 | 46.29 | 0 | 0.54 | 0.01 |
|  | 38 | 12.80 | 0.09 | 1.94 | 2.08 | 1.35 | 0.73 | 14.54 | 0.11 | 45.61 | 0 | 0.49 | 0.01 |
| GLA | 39 | 12.10 | 0.09 | 2.37 | 2.10 | 1.29 | 0.82 | 14.85 | 1.63 | 43.66 | 0 | 0.53 | 0 |
|  | 40 | 12.78 | 0.10 | 2.34 | 2.22 | 1.36 | 0.86 | 15.29 | 1.72 | 47.22 | 0 | 0.50 | 0.02 |
|  | 41 | 13.71 | 0.07 | 2.68 | 2.16 | 1.34 | 0.82 | 15.92 | 2.12 | 46.55 | 0 | 0.09 | 0 |
|  | 42 | 14.10 | 0.07 | 2.75 | 2.35 | 1.51 | 0.84 | 16.66 | 1.56 | 46.41 | 0 | 0.09 | 0.01 |
|  | 43 | 13.62 | 0.09 | 2.22 | 1.94 | 1.21 | 0.73 | 14.68 | 2.42 | 46.69 | 0 | 0.51 | 0.01 |
|  | 44 | 13.92 | 0.09 | 2.20 | 2.17 | 1.32 | 0.85 | 15.22 | 2.30 | 46.05 | 0 | 0.53 | 0.02 |
| DGLA | 45 | 12.45 | 0.14 | 2.30 | 2.28 | 1.37 | 0.91 | 15.65 | 0.07 | 44.62 | 0 | 0.12 | 0.01 |
|  | 46 | 12.67 | 0.15 | 2.69 | 2.50 | 1.58 | 0.92 | 15.96 | 0.09 | 42.77 | 0 | 0.56 | 0.01 |
|  | 47 | 12.56 | 0.23 | 3.40 | 1.98 | 1.13 | 0.86 | 13.57 | 0.03 | 45.52 | 0 | 0.51 | 0.01 |
|  | 48 | 13.07 | 0.24 | 3.60 | 2.51 | 1.63 | 0.88 | 13.54 | 0.04 | 45.13 | 0 | 0.50 | 0.01 |
|  | 49 | 13.26 | 0.07 | 2.81 | 2.34 | 1.67 | 0.67 | 16.04 | 0.04 | 43.89 | 0 | 0.59 | 0 |
|  | 50 | 13.53 | 0.07 | 2.84 | 2.41 | 1.70 | 0.70 | 16.07 | 0.02 | 44.90 | 0 | 0.60 | 0.01 |

| Treatment | SPL # | 20:02 % | 20:03 % | 20:04 % | 20:05 % | 22:00 % | 22:01 % | 22:02 % | 22:03 % | 22:06 % | 24:0 % | 24:1 % |
|---|---|---|---|---|---|---|---|---|---|---|---|---|
| Water | 33 | 0 | 0 | 0.29 | 0 | 0.01 | 0.09 | 16.26 | 0 | 0 | 0.38 | 0.18 |
|  | 34 | 0.01 | 0 | 0.26 | 0 | 0.14 | 0.10 | 16.82 | 0.02 | 0.05 | 0.36 | 0.27 |
|  | 35 | 0.01 | 0 | 0.25 | 0 | 0.12 | 0.06 | 11.29 | 0.04 | 0.05 | 0.29 | 0.25 |
|  | 36 | 0 | 0.01 | 0.26 | 0 | 0.07 | 0.04 | 11.82 | 0.03 | 0.36 | 0.28 | 0.21 |
|  | 37 | 0.02 | 0 | 0.21 | 0 | 0.18 | 0.08 | 15.87 | 0.06 | 0.20 | 0.30 | 0.17 |
|  | 38 | 0.01 | 0 | 0.24 | 0 | 0.15 | 0.07 | 13.64 | 0.09 | 0.08 | 5.89 | 0.23 |
| GLA | 39 | 0.02 | 0.01 | 0.27 | 0 | 0.10 | 0.08 | 16.25 | 3.42 | 0.19 | 0.37 | 0.17 |
|  | 40 | 0.01 | 0 | 0.27 | 0 | 0.10 | 0.10 | 14.74 | 0.05 | 0.10 | 0.36 | 0.14 |
|  | 41 | 0 | 0 | 0.27 | 0 | 0.20 | 0.10 | 13.15 | 0.13 | 0.29 | 0.33 | 0.20 |
|  | 42 | 0 | 0 | 0.28 | 0 | 0.11 | 0.11 | 12.60 | 0.02 | 0.24 | 0.38 | 0.13 |
|  | 43 | 0.01 | 0 | 0.28 | 0 | 0.10 | 0.03 | 14.73 | 0.01 | 0.24 | 0.34 | 0.14 |
|  | 44 | 0.02 | 0 | 0.26 | 0 | 0.13 | 0.07 | 14.43 | 0.05 | 0.16 | 0.33 | 0.17 |
| DGLA | 45 | 0.06 | 1.21 | 0.26 | 0 | 0.07 | 0.07 | 18.67 | 0.02 | 0.21 | 0.36 | 0.13 |
|  | 46 | 0 | 1.94 | 0.27 | 0 | 0.11 | 0.09 | 17.97 | 0.09 | 0.39 | 0.41 | 0.11 |
|  | 47 | 0.01 | 0.69 | 0.96 | 0 | 0.11 | 0.07 | 17.96 | 0 | 0.22 | 0.49 | 0.20 |
|  | 48 | 0.01 | 0.70 | 0.74 | 0 | 0.14 | 0.09 | 17.14 | 0.05 | 0.32 | 0.52 | 0.10 |
|  | 49 | 0 | 0.35 | 1.11 | 0 | 0.10 | 0.07 | 17.26 | 0.07 | 0.23 | 0.39 | 0.18 |
|  | 50 | 0 | 0.20 | 0.87 | 0 | 0.21 | 0.07 | 15.73 | 0.04 | 0.15 | 0.37 | 0.18 |

Leaves treated with GLA contained from 1.56 to 2.4 wt % GLA. The fatty acid analysis showed that the lipid composition of control and transgenic leaves was essentially the same. Leaves of control plants treated with DGLA contained 1.2-1.9 w % DGLA and background amounts of ARA (0.26-0.27 wt %). Transgenic leaves contained only 0.2-0.7 wt % DGLA, but levels of ARA were increased (0.74-1.1 wt %) indicating that the DGLA was converted to ARA in these leaves.

Expression in Seed

The purpose of this experiment was to determine whether a construct with the seed specific napin promoter would enable expression in seed.

The Ma29 cDNA was modified by PCR to introduce XhoI cloning sites upstream and downstream of the start and stop codons, respectively, using the following primers:

Madxho-forward:
5'-CUACUACUACUACUCGAGCAAGATGG-GAACGGACCAAGG (SEQ ID NO:25)

Madxho-reverse:
5'-CAUCAUCAUCAUCUCGAGCTACTCTTC-CTTGGGACGGAG (SEQ ID NO:26).

The PCR product was subcloned into pAMP1 (GIBCO-BRL) using the CloneAmp system (GIBCOBRL) to create pCGN5522 and the Δ5 desaturase sequence was verified by sequencing of both strands.

For seed-specific expression, the Ma29 coding region was cut out of pCGN5522 as an XhoI fragment and inserted into the SalI site of the napin expression cassette, pCGN3223, to create pCGN5528. The HindIII fragment of pCGN5528 containing the napin 5' regulatory region, the Ma29 coding region, and the napin 3' regulatory region was inserted into the HindIII site of pCGN1557 to create pCGN5531. Two copies of the napin transcriptional unit were inserted in tandem. This tandem construct can permit higher expression of the desaturases per genetic loci. pCGN5531 was introduced into Brassica napus cv.LP004 via Agrobacterium mediated transformation.

The fatty acid composition of twenty-seed pools of mature T2 seeds was analyzed by GC. Table 4 shows the results obtained with independent transformed lines as compared to non-transformed LP004 seed. The transgenic seeds containing pCGN5531 contain two fatty acids that are not present in the control seeds, tentatively identified as taxoleic acid (5,9-18:2) and pinolenic acid (5,9,12-18:3), based on their elution relative to oleic and linoleic acid. These would be the expected products of Δ5 desaturation of oleic and linoleic acids. No other differences in fatty acid composition were observed in the transgenic seeds.

Northern analysis is performed on plants to identify those expressing Ma29. Developing embryos are isolated approximately 25 days post anthesis or when the napin promoter is induced, and floated in a solution containing GLA or DGLA as described in Example 7. Fatty acid analysis of the embryos is then performed by GC to determine the amount of conversion of DGLA to ARA, following the protocol adapted for leaves in Example 7. The amount of ARA incorporated into triglycerides by endogenous Brassica acyltransferases is then evaluated by GC analysis as in Example 7.

Example 8

Expression of *M. alpina* Δ06 Desaturase in *Brassica napus*

The Ma524 cDNA was modified by PCR to introduce cloning sites using the following primers:

Ma524PCR-1 (SEQ ID NO:27)

5'-CUACUACUACUAUCTAGACTCGAGAC-CATGGCTGCTGCT CCAGTGTG

Ma524PCR-2 (SEQ ID NO:28)

5'-CAUCAUCAUCAUAGGCCTCGAGTTACT-GCGCCTTACCCAT

These primers allowed the amplification of the entire coding region and added XbaI and XhoI sites to the 5'-end and XhoI and StuI sites to the 3' end. The PCR product was subcloned into pAMP1 (GIBCOBRL) using the CloneAmp system (GIBCOBRL) to create pCGN5535 and the Δ6 desaturase sequence was verified by sequencing of both strands.

For seed-specific expression, the Ma524 coding region was cut out of pCGN5535 as an XhoI fragment and inserted into the SalI site of the napin expression cassette, pCGN3223, to create pCGN5536. The NotI fragment of pCGN5536 containing the napin 5' regulatory region, the Ma524 coding region, and the napin 3' regulatory region was inserted into the NotI site of pCGN1557 to create pCGN5538. pCGN5538 was introduced into *Brassica napus* cv.LP004 via *Agrobacterium* mediated transformation.

Maturing T2 seeds were collected from 6 independent transformation events in the greenhouse. The fatty acid composition of single seeds was analyzed by GC. Table 5 shows the results of control LP004 seeds and six 5538 lines. All of the 5538 lines except #8 produced seeds containing GLA. Presence of GLA segregated in these seeds as is expected for the T2 selfed seed population. In addition to GLA, the *M. alpina* Δ6 desaturase is capable of producing 18:4 (stearidonic) and another fatty acid believed to be the 6,9-18:2.

TABLE 4

Composition of T2 Pooled Seed

| | 16:0 % | 16:1 % | 18:0 % | 18:1 % | (5,9)18:2 % | 18:2 % | (5,9,12)18:3 % | 18:3 % | 20:0 % | 20:1 % | 20:2 % | 22:0 % | 22:1 % | 24:0 % |
|---|---|---|---|---|---|---|---|---|---|---|---|---|---|---|
| LP004 control | 3.86 | 0.15 | 3.05 | 69.1 | 0 | 18.51 | 0.01 | 1.65 | 1.09 | 1.40 | 0.03 | 0.63 | 0.05 | 0.42 |
| 5531-1 | 4.26 | 0.15 | 3.23 | 62.33 | 4.07 | 21.44 | 0.33 | 1.38 | 0.91 | 1.04 | 0.05 | 0.41 | 0.03 | 0.27 |
| 5531-2 | 3.78 | 0.14 | 3.37 | 66.18 | 4.57 | 17.31 | 0.27 | 1.30 | 1.03 | 1.18 | 0 | 0.47 | 0.01 | 0.30 |
| 5531-6 | 3.78 | 0.13 | 3.47 | 63.61 | 6.21 | 17.97 | 0.38 | 1.34 | 1.04 | 1.14 | 0.05 | 0.49 | 0.02 | 0.26 |
| 5531-10 | 3.96 | 0.17 | 3.28 | 63.82 | 5.41 | 18.58 | 0.32 | 1.43 | 0.98 | 1.11 | 0.02 | 0.50 | 0 | 0.31 |
| 5531-16 | 3.91 | 0.17 | 3.33 | 64.31 | 5.03 | 18.98 | 0.33 | 1.39 | 0.96 | 1.11 | 0 | 0.44 | 0 | 0 |
| 5531-28 | 3.81 | 0.13 | 2.58 | 62.64 | 5.36 | 20.95 | 0.45 | 1.39 | 0.83 | 1.15 | 0.01 | 0.36 | 0.05 | 0.21 |

The above results show that desaturases with three different substrate specificities can be expressed in a heterologous system and used to produce poly-unsaturated long chain fatty acids. Exemplified were the production of ARA (20:4) from the precursor 20:3 (DGLA), the production of GLA (18:3) from 18:2 substrate, and the conversion of 18:1 substrate to 18:2, which is the precursor for GLA.

TABLE 5

Fatty Acid Analysis of Seeds from Ma524 Transgenic *Brassica* Plants

| SPL # | 16:0 % | 16:1 % | 18:1 % | 18:0 | 6,9 18:2 % | 18:2 % | 18:3ga % | 18:3 % | 18:4 % | 20:1 % | 22:0 % | 22:1 % | 24:0 % | 24:1 % |
|---|---|---|---|---|---|---|---|---|---|---|---|---|---|---|
| LPOO4-1 | 4.33 | 0.21 | 3.78 | 72.49 | 0 | 13.97 | 0 | 1.7 | 0 | 1.34 | 0.71 | 0.02 | 0.58 | 0.27 |
| -2 | 4.01 | 0.16 | 3.09 | 73.59 | 0 | 14.36 | 0.01 | 1.4 | 0 | 1.43 | 0.66 | 0.02 | 0.5 | 0.2 |
| -3 | 4.12 | 0.19 | 3.56 | 70.25 | 0 | 17.28 | 0 | 1.57 | 0 | 1.28 | 0.5 | 0.02 | 0.39 | 0.2 |
| -4 | 4.22 | 0.2 | 2.7 | 70.25 | 0 | 17.86 | 0 | 1.61 | 0 | 1.31 | 0.53 | 0.02 | 0.4 | 0.24 |
| -5 | 4.02 | 0.16 | 3.41 | 72.91 | 0 | 14.45 | 0.01 | 1.45 | 0 | 1.37 | 0.7 | 0.02 | 0.51 | 0.26 |
| -6 | 4.22 | 0.18 | 3.23 | 71.47 | 0 | 15.92 | 0.01 | 1.52 | 0 | 1.32 | 0.69 | 0.02 | 0.51 | 0.27 |
| -7 | 4.1 | 0.16 | 3.47 | 72.06 | 0 | 15.23 | 0 | 1.52 | 0 | 1.32 | 0.63 | 0.03 | 0.49 | 0.23 |
| -9 | 4.01 | 0.17 | 3.71 | 72.98 | 0 | 13.97 | 0.01 | 1.41 | 0 | 1.45 | 0.74 | 0.03 | 0.58 | 0.23 |
| -10 | 4.04 | 0.16 | 3.57 | 70.03 | 0 | 17.46 | 0 | 1.5 | 0 | 1.33 | 0.61 | 0.03 | 0.36 | 0.24 |
| 5538-1-1 | 4.61 | 0.2 | 3.48 | 68.12 | 1.37 | 10.68 | 7.48 | 1.04 | 0.33 | 1.19 | 0.49 | 0.02 | 0.33 | 0.13 |
| -2 | 4.61 | 0.22 | 3.46 | 68.84 | 1.36 | 10.28 | 7.04 | 1.01 | 0.31 | 1.15 | 0.48 | 0.02 | 0.39 | 0 |
| -3 | 4.78 | 0.24 | 3.24 | 65.86 | 0 | 21.36 | 0 | 1.49 | 0 | 1.08 | 0.46 | 0.02 | 0.38 | 0.22 |
| -4 | 4.84 | 0.3 | 3.89 | 67.64 | 1.67 | 9.9 | 6.97 | 1.02 | 0.36 | 1.14 | 0.53 | 0.02 | 0.5 | 0.18 |
| -5 | 4.64 | 0.2 | 3.58 | 64.5 | 3.61 | 8.85 | 10.14 | 0.95 | 0.48 | 1.19 | 0.47 | 0.01 | 0.33 | 0.12 |
| -6 | 4.91 | 0.27 | 3.44 | 66.51 | 1.48 | 11.14 | 7.74 | 1.15 | 0.33 | 1.08 | 0.49 | 0.02 | 0.34 | 0.13 |
| -7 | 4.87 | 0.22 | 3.24 | 65.78 | 1.27 | 11.92 | 8.38 | 1.2 | 0 | 1.12 | 0.47 | 0.02 | 0.37 | 0.16 |
| -8 | 4.59 | 0.22 | 3.4 | 70.77 | 0 | 16.71 | 0 | 1.35 | 0 | 1.14 | 0.48 | 0.02 | 0.39 | 0.15 |
| -9 | 4.63 | 0.23 | 3.51 | 69.66 | 2.01 | 8.77 | 7.24 | 0.97 | 0 | 1.18 | 0.52 | 0.02 | 0.3 | 0.11 |
| -10 | 4.56 | 0.19 | 3.55 | 70.68 | 0 | 16.89 | 0 | 1.37 | 0 | 1.22 | 0.54 | 0.02 | 0.22 | 0.03 |
| 5538-3-1 | 4.74 | 0.21 | 3.43 | 67.52 | 1.29 | 10.91 | 7.77 | 1.03 | 0.28 | 1.11 | 0.5 | 0.02 | 0.35 | 0.14 |
| -2 | 4.72 | 0.21 | 3.24 | 67.42 | 1.63 | 10.37 | 8.4 | 0.99 | 0 | 1.12 | 0.49 | 0.02 | 0.36 | 0.15 |
| -3 | 4.24 | 0.21 | 3.52 | 71.31 | 0 | 16.53 | 0 | 1.33 | 0 | 1.12 | 0.45 | 0.02 | 0.4 | 0.14 |
| -4 | 4.64 | 0.21 | 3.45 | 67.92 | 1.65 | 9.91 | 7.97 | 0.91 | 0.33 | 1.14 | 0.47 | 0.02 | 0.37 | 0.14 |
| -5 | 4.91 | 0.25 | 3.31 | 67.19 | 0 | 19.92 | 0.01 | 1.39 | 0 | 1.05 | 0.48 | 0.02 | 0.37 | 0.14 |
| -6 | 4.67 | 0.21 | 3.25 | 67.07 | 1.23 | 11.32 | 8.35 | 0.99 | 0 | 1.16 | 0.47 | 0.02 | 0.33 | 0.16 |
| -7 | 4.53 | 0.19 | 2.94 | 64.8 | 4.94 | 8.45 | 9.95 | 0.93 | 0.44 | 1.13 | 0.37 | 0.01 | 0.27 | 0.12 |
| -8 | 4.66 | 0.22 | 3.68 | 67.33 | 0.71 | 12 | 6.99 | 1.1 | 0.24 | 1.18 | 0.48 | 0.03 | 0.36 | 0.17 |
| -9 | 4.65 | 0.24 | 3.11 | 67.42 | 0.64 | 12.71 | 6.93 | 1.16 | 0.25 | 1.08 | 0.45 | 0.02 | 0.32 | 0.17 |
| -10 | 4.88 | 0.27 | 3.33 | 65.75 | 0.86 | 12.89 | 7.7 | 1.1 | 0.24 | 1.08 | 0.46 | 0.01 | 0.34 | 0.16 |
| 5538-4-1 | 4.65 | 0.24 | 3.8 | 62.41 | 0 | 24.68 | 0 | 1.6 | 0.01 | 0.99 | 0.45 | 0.02 | 0.33 | 0.13 |
| -2 | 5.37 | 0.31 | 3 | 57.98 | 0.38 | 18.04 | 10.5 | 1.41 | 0 | 0.99 | 0.48 | 0.02 | 0.3 | 0.19 |
| -3 | 4.61 | 0.22 | 3.07 | 63.62 | 0.3 | 16.46 | 7.67 | 1.2 | 0 | 1.18 | 0.45 | 0.02 | 0.29 | 0.14 |
| -4 | 4.39 | 0.19 | 2.93 | 65.97 | 0 | 22.36 | 0 | 1.45 | 0 | 1.17 | 0.41 | 0.03 | 0.32 | 0.15 |
| -5 | 5.22 | 0.29 | 3.85 | 62.1 | 2.35 | 10.25 | 11.39 | 0.93 | 0.41 | 1.04 | 0.6 | 0.02 | 0.47 | 0.17 |
| -6 | 4.66 | 0.18 | 2.85 | 66.79 | 0.5 | 13.03 | 7.66 | 0.97 | 0.22 | 1.28 | 0.42 | 0.02 | 0.31 | 0.14 |
| -7 | 4.85 | 0.26 | 3.03 | 57.43 | 0.26 | 28.04 | 0.01 | 2.59 | 0.01 | 1.13 | 0.56 | 0.02 | 0.4 | 0.23 |
| -8 | 5.43 | 0.28 | 2.94 | 54.8 | 1.84 | 13.79 | 15.67 | 1.36 | 0.53 | 1.1 | 0.55 | 0.02 | 0.35 | 0.19 |
| -9 | 4.88 | 0.24 | 3.32 | 62.3 | 0.58 | 14.86 | 9.04 | 1.34 | 0.29 | 1.13 | 0.52 | 0.02 | 0.37 | 0.19 |
| -10 | 4.53 | 0.2 | 2.73 | 64.2 | 0.07 | 24.15 | 0 | 1.52 | 0 | 1.09 | 0.39 | 0.02 | 0.27 | 0.17 |
| 5538-5-1 | 4.5 | 0.15 | 3.35 | 66.71 | 0.88 | 11.7 | 8.38 | 1.04 | 0.3 | 1.24 | 0.49 | 0.02 | 0.29 | 0.17 |
| -2 | 4.77 | 0.23 | 3.06 | 62.67 | 0.68 | 15.2 | 8.8 | 1.31 | 0.28 | 1.15 | 0.46 | 0.02 | 0.3 | 0.19 |
| -3 | 4.59 | 0.22 | 3.61 | 64.35 | 2.29 | 9.95 | 10.57 | 1.01 | 0.45 | 1.21 | 0.48 | 0.02 | 0.26 | 0.16 |
| -4 | 4.86 | 0.26 | 3.4 | 67.69 | 0.65 | 12.24 | 6.61 | 1.09 | 0.23 | 1.07 | 0.45 | 0.02 | 0.32 | 0.14 |
| -5 | 4.49 | 0.21 | 3.3 | 69.25 | 0.04 | 16.51 | 2.18 | 1.2 | 0 | 1.11 | 0.44 | 0.02 | 0.33 | 0.16 |
| -6 | 4.5 | 0.21 | 3.47 | 70.48 | 0.08 | 14.9 | 2.19 | 1.22 | 0 | 1.13 | 0.49 | 0.02 | 0.33 | 0.16 |
| -7 | 4.39 | 0.21 | 3.44 | 67.59 | 2.38 | 9.24 | 8.98 | 0.89 | 0 | 1.18 | 0.44 | 0.02 | 0.28 | 0.14 |
| -8 | 4.52 | 0.22 | 3.17 | 68.33 | 0.01 | 18.91 | 0.73 | 1.32 | 0.01 | 1.08 | 0.45 | 0.02 | 0.29 | 0.17 |
| -9 | 4.68 | 0.2 | 3.05 | 64.03 | 1.93 | 11.03 | 11.41 | 1.02 | 0.01 | 1.15 | 0.39 | 0.02 | 0.21 | 0.15 |
| -10 | 4.57 | 0.2 | 3.1 | 67.21 | 0.61 | 12.62 | 7.68 | 1.07 | 0.25 | 1.14 | 0.43 | 0.02 | 0.25 | 0.15 |
| 5538-8-1 | 4.95 | 0.26 | 3.14 | 64.04 | 0 | 23.38 | 0 | 1.54 | 0 | 0.99 | 0.42 | 0.02 | 0.38 | 0.17 |
| -2 | 4.91 | 0.26 | 3.71 | 62.33 | 0 | 23.97 | 0 | 1.77 | 0 | 0.95 | 0.53 | 0.02 | 0.42 | 0.19 |
| -3 | 4.73 | 0.25 | 4.04 | 63.83 | 0 | 22.36 | 0.01 | 1.73 | 0 | 1.05 | 0.55 | 0.02 | 0.45 | 0.16 |
| -4 | 5.1 | 0.35 | 3.8 | 60.45 | 0 | 24.45 | 0.01 | 2.13 | 0 | 1.07 | 0.65 | 0.03 | 0.53 | 0.24 |
| -5 | 4.98 | 0.3 | 3.91 | 62.48 | 0 | 23.44 | 0 | 1.77 | 0 | 1.01 | 0.51 | 0.01 | 0.43 | 0.21 |
| -6 | 4.62 | 0.21 | 3.99 | 66.14 | 0 | 20.38 | 0 | 1.48 | 0 | 1.15 | 0.53 | 0.02 | 0.48 | 0.19 |
| -7 | 4.64 | 0.22 | 3.55 | 64.6 | 0 | 22.65 | 0 | 1.38 | 0 | 1.09 | 0.45 | 0.02 | 0.41 | 0.19 |
| -8 | 5.65 | 0.38 | 3.18 | 56.6 | 0 | 30.83 | 0.02 | 0.02 | 0 | 0.98 | 0.55 | 0.03 | 0.39 | 0.26 |
| -9 | 8.53 | 0.63 | 6.9 | 51.76 | 0 | 26.01 | 0 | 0.01 | 0 | 1.41 | 1.21 | 0.07 | 0.96 | 0.33 |
| -10 | 5.52 | 0.4 | 3.97 | 57.92 | 0 | 28.95 | 0 | 0.02 | 0 | 0.95 | 0.52 | 0.02 | 0.41 | 0.16 |
| 5538-10-1 | 4.44 | 0.19 | 3.5 | 68.42 | 0 | 19.51 | 0 | 1.32 | 0 | 1.14 | 0.45 | 0.02 | 0.31 | 0.16 |
| -2 | 4.57 | 0.21 | 3.07 | 66.08 | 0 | 21.99 | 0.01 | 1.36 | 0 | 1.12 | 0.41 | 0.02 | 0.31 | 0.16 |
| -3 | 4.63 | 0.21 | 3.48 | 67.43 | 0 | 20.27 | 0 | 1.32 | 0 | 1.12 | 0.46 | 0.02 | 0.21 | 0.08 |
| -4 | 4.69 | 0.19 | 3.22 | 64.62 | 0 | 23.16 | 0 | 1.35 | 0 | 1.08 | 0.46 | 0.02 | 0.33 | 0.2 |
| -5 | 4.58 | 0.2 | 3.4 | 68.75 | 0 | 20.17 | 0.01 | 0.02 | 0 | 1.1 | 0.45 | 0.02 | 0.34 | 0.17 |
| -8 | 4.55 | 0.21 | 0 | 73.55 | 0.05 | 14.91 | 2.76 | 1.21 | 0.07 | 1.24 | 0.51 | 0.02 | 0.19 | 0 |
| -9 | 4.58 | 0.21 | 3.28 | 66.19 | 0 | 21.55 | 0 | 1.35 | 0 | 1.12 | 0.43 | 0.02 | 0.33 | 0.16 |
| -10 | 4.52 | 0.2 | 3.4 | 68.37 | 0 | 19.33 | 0.01 | 1.3 | 0 | 1.13 | 0.46 | 0.02 | 0.35 | 0.18 |

Example 9

Expression of *M. alpina* Δ12 Desaturase in *Brassica napus*

The Ma648 cDNA was modified by PCR to introduce cloning sites using the following primers:

Ma648PCR-for (SEQ ID NO:29) 5'-CUACUACUAC-UAGGATCCATGGCACCTCCCAACACT

Ma648PCR-rev (SEQ ID NO:30) 5'-CAUCAUCAU-CAUGGTACCTCGAGTTACTTCTTGAAAAAGAC

These primers allowed the amplification of the entire coding region and added a BamHI site to the 5' end and KpnI and XhoI sites to the 3' end. The PCR product was subcloned into pAMP1 (GIBCOBRL) using the CloneAmp system (GIBCOBRL) to create pCGN5540 and the Δ12 desaturase sequence was verified by sequencing of both strands.

For seed-specific expression, the Ma648 coding region was cut out of pCGN5540 as a BamHI/XhoI fragment and inserted between the BglII and XhoI sites of the napin expression cassette, pCGN3223, to create pCGN5542. The Asp718 fragment of pCGN5541 containing the napin 5' regulatory region, the Ma648 coding region, and the napin 3' regulatory region was inserted into the Asp718 site of pCGN5138 to create pCGN5542. PCGN5542 was introduced into two varieties of *Brassica napus* via *Agrobacterium* mediated transformation. The commercial canola variety, SP30021, and a low-linolenic line, LP30108 were used.

Mature selfed T2 seeds were collected from 19 independent LP30108 transformation events and a non-transformed control grown in the greenhouse. These seeds are expected to be segregating for the Δ12 desaturase transgene. The fatty acid composition of 20-seed pools was analyzed by GC. The results are shown in Table 6. All transformed lines contained increased levels of 18:2, the product of the Δ12 desaturase. Levels of 18:3 were not significantly increased in these plants.

Events #11 and 16 showed the greatest accumulation of 18:2 in the pooled seeds. To investigate the segregation of 18:2 levels in the T2 seeds and to identify individual plants to be taken on to subsequent generations, half-seed analysis was done. Seeds were germinated overnight in the dark at 30 degrees on water-soaked filter paper. The outer cotyledon was excised for GC analysis and the rest of the seedling was planted in soil. Results of some of these analyses are shown in Table 7. Individual T2 seeds containing the *M. alpina* Δ12 desaturase accumulated up to 60% 18:2 in the seeds. Sample 97xx1116 #59 is an example of a null segregant. Even in the highest 18:2 accumulators, levels of 18:3 were increased only slightly. These and other individually selected T2 plants were grown in the greenhouse and in the field to produce T3 seed.

Mature selfed T2 seeds were collected from 20 independent SP30021 transformation events and a non-transformed control grown in the greenhouse. These seeds are expected to be segregating for the Δ12 desaturase transgene. The fatty acid composition of 20-seed pools was analyzed by GC. The data are presented in Table 8. All transformed lines contained increased levels of 18:2, the product of the Δ12 desaturase. As in the low-linolenic LP30108 line, levels of 18:3 were not significantly increased. Events #4 and 12 showed the greatest accumulation of 18:2 in the pooled seeds. To investigate the segregation of 18:2 levels in the T2 seeds and to identify individual plants to be taken on to subsequent generations, alf-seed analysis was done. Seeds were germinated overnight in the dark at 30 degrees on water-soaked filter paper. The outer cotyledon was excised for GC analysis and the rest of the seedling was planted in soil. Results of some of these analyses are shown in Table 9. Samples 97xx1157 #88 and #18 are examples of null segregants for 5542-SP30021-4 and 5542-SP30021-12 respectively. These and other individually selected T2 plants were grown in the greenhouse and in the field to produce T3 seed

TABLE 6

| CYCLE ID | SPL NO | STRAIN ID | 16:0 | 16:1 | 18:0 | 18:1 | 18:2 | 18:3 | 20:0 | 20:1 | 20:2 | 22:0 |
|---|---|---|---|---|---|---|---|---|---|---|---|---|
| 97XX1098 | 45 | 5542-LP30108-16 | 7.04 | 0.43 | 1.12 | 18.01 | 66.38 | 4.76 | 0.5 | 0.84 | 0.3 | 0.44 |
| 97XX1098 | 22 | 5542-LP30108-16 | 5.17 | 0.29 | 2.11 | 22.01 | 65.18 | 3.15 | 0.63 | 0.75 | 0.21 | 0.36 |
| 97XX1098 | 40 | 5542-LP30108-16 | 4.99 | 0.2 | 2.05 | 23.91 | 63.13 | 3.3 | 0.73 | 0.85 | 0.23 | 0.49 |
| 97XX1098 | 28 | 5542-LP30108-16 | 4.47 | 0.19 | 1.75 | 26.7 | 62.39 | 2.46 | 0.58 | 0.85 | 0.2 | 0.32 |
| 97XX1098 | 2 | 5542-LP30108-16 | 4.54 | 0.21 | 1.66 | 26.83 | 61.89 | 2.9 | 0.55 | 0.82 | 0.18 | 0.33 |
| 97XX1098 | 58 | 5542-LP30108-16 | 6.05 | 0.31 | 1.36 | 24.11 | 61.36 | 3.8 | 0.72 | 1.13 | 0.26 | 0.58 |
| 97XX1098 | 83 | 5542-LP30108-16 | 5.13 | 0.17 | 2.03 | 27.05 | 60.93 | 2.62 | 0.7 | 0.71 | 0.14 | 0.4 |
| 97XX1098 | 34 | 5542-LP30108-16 | 4.12 | 0.19 | 1.44 | 29.35 | 60.54 | 2.53 | 0.43 | 0.89 | 0.17 | 0.25 |
| 97XX1116 | 37 | 5542-LP30108-11 | 4 | 0.14 | 2.43 | 23.29 | 63.99 | 2.6 | 0.58 | 0.69 | 0.71 | 1.11 |
| 97XX1116 | 88 | 5542-LP30108-11 | 3.8 | 0.18 | 2.04 | 23.59 | 63.93 | 2.95 | 0.54 | 0.81 | 0.99 | 0.82 |
| 97XX1116 | 36 | 5542-LP30108-11 | 4.15 | 0.2 | 1.51 | 25.94 | 62.14 | 2.74 | 0.47 | 0.87 | 0.79 | 0.81 |
| 97XX1116 | 31 | 5542-LP30108-11 | 6.29 | 0.35 | 1.04 | 24.14 | 60.91 | 4.02 | 0.55 | 0.91 | 0.75 | 0.72 |
| 97XX1116 | 10 | 5542-LP30108-11 | 6.97 | 0.4 | 3.36 | 18.9 | 60.66 | 4.68 | 1.2 | 0.7 | 0.53 | 1.71 |
| 97XX1116 | 32 | 5542-LP30108-11 | 3.96 | 0.16 | 2.61 | 26.73 | 60.54 | 3.38 | 0.66 | 0.87 | 0.2 | 0.62 |
| 97XX1116 | 55 | 5542-LP30108-11 | 4.26 | 0.22 | 0.98 | 28.57 | 59.94 | 3.24 | 0.4 | 0.68 | 0.71 | 0.75 |
| 97XX1116 | 12 | 5542-LP30108-11 | 4.17 | 0.23 | 1.42 | 28.61 | 59.52 | 3.26 | 0.51 | 0.95 | 0.29 | 0.67 |
| 97XX1116 | 86 | 5542-LP30108-11 | 4.23 | 0.3 | 1.09 | 28.34 | 59.2 | 3.95 | 0.48 | 0.91 | 0.55 | 0.71 |
| 97XX1116 | 61 | 5542-LP30108-11 | 4.13 | 0.16 | 1.92 | 30.18 | 58.67 | 2.65 | 0.56 | 0.88 | 0.25 | 0.41 |
| 97XX1116 | 60 | 5542-LP30108-11 | 4.42 | 0.26 | 1.61 | 28.77 | 58.6 | 3.26 | 0.53 | 0.85 | 0.68 | 0.75 |
| 97XX1116 | 91 | 5542-LP30108-11 | 7.82 | 0.67 | 2.37 | 17.97 | 58.43 | 4.85 | 0.94 | 0.86 | 3.87 | 1.71 |
| 97XX1116 | 59 | 5542-LP30108-11 | 3.56 | 0.2 | 1.6 | 65.5 | 23.03 | 2.23 | 0.52 | 1.54 | 0.49 | 0.69 |

TABLE 7

| | 16:0 % | 16:1 % | 18:0 % | 18:1 % | 18:2 % | 18:3 % | 20:0 % | 20:1 % | 20:2 % | 22:0 % |
|---|---|---|---|---|---|---|---|---|---|---|
| 5542-LP30108-1 | 4.6 | 0.15 | 1.93 | 50.44 | 38.54 | 2.06 | 0.65 | 1.11 | 0.09 | 0.37 |
| 5542-LP30108-2 | 4.63 | 0.17 | 1.78 | 41.11 | 47.53 | 2.46 | 0.62 | 1.02 | 0.14 | 0.38 |
| 5542-LP30108-3 | 4.96 | 0.18 | 2.07 | 48.16 | 40.01 | 2.17 | 0.73 | 1.13 | 0.1 | 0.39 |
| 5542-LP30108-4 | 4.36 | 0.15 | 1.94 | 46.51 | 42.57 | 1.95 | 0.64 | 1.06 | 0.11 | 0.35 |
| 5542-LP30108-5 | 4.45 | 0.14 | 2.19 | 49.54 | 39.13 | 2.14 | 0.72 | 1.14 | 0.11 | 0.38 |
| 5542-LP30108-6 | 4.97 | 0.16 | 1.86 | 49.23 | 39.2 | 2.17 | 0.7 | 1.12 | 0.11 | 0.41 |
| 5542-LP30108-7 | 4.46 | 0.13 | 2.72 | 39.6 | 48.65 | 2.02 | 0.81 | 0.96 | 0.13 | 0.4 |
| 5542-LP30108-8 | 4.63 | 0.18 | 1.78 | 47.86 | 41 | 2.31 | 0.62 | 1.09 | 0.11 | 0.36 |
| 5542-LP30108-9 | 4.64 | 0.16 | 1.75 | 42.5 | 46.57 | 2.2 | 0.61 | 1 | 0.13 | 0.35 |
| 5542-LP30108-10 | 4.46 | 0.15 | 2.37 | 43.61 | 45.29 | 1.77 | 0.71 | 1.02 | 0.12 | 0.36 |
| 5542-LP30108-11 | 4.58 | 0.25 | 1.88 | 37.08 | 50.95 | 2.94 | 0.64 | 0.96 | 0.16 | 0.42 |
| 5542-LP30108-12 | 4.46 | 0.18 | 1.69 | 43.62 | 45.36 | 2.44 | 0.59 | 1.09 | 0.14 | 0.34 |
| 5542-LP30108-13 | 4.45 | 0.15 | 2.33 | 51 | 37.71 | 1.91 | 0.75 | 1.12 | 0.09 | 0.4 |
| 5542-LP30108-14 | 4.3 | 0.16 | 2.04 | 45.93 | 42.78 | 2.46 | 0.66 | 1.07 | 0.14 | 0.37 |
| 5542-LP30108-15 | 4.18 | 0.16 | 2.17 | 43.79 | 45.2 | 2.14 | 0.68 | 1.04 | 0.15 | 0.36 |
| 5542-LP30108-16 | 5.04 | 0.18 | 1.89 | 32.32 | 55.78 | 2.68 | 0.63 | 0.84 | 0.2 | 0.36 |
| 5542-LP30108-18 | 4.2 | 0.14 | 2.23 | 50.63 | 38.51 | 1.79 | 0.72 | 1.15 | 0.1 | 0.37 |
| 5542-LP30108-19 | 4.63 | 0.18 | 1.81 | 52.51 | 36.26 | 2.12 | 0.68 | 1.19 | 0.1 | 0.4 |
| 5542-LP30108-20 | 4.77 | 0.15 | 2.78 | 39.76 | 48.06 | 2.25 | 0.75 | 0.91 | 0.13 | 0.36 |
| LP30108 control | 4.31 | 0.22 | 2.05 | 66.15 | 22.59 | 1.87 | 0.77 | 1.3 | 0.07 | 0.44 |

TABLE 8

| STRAIN ID | 16:0 | 16:1 | 18:0 | 18:1 | 18:2 | 18:3 | 20:0 | 20:1 | 20:2 | 22:0 |
|---|---|---|---|---|---|---|---|---|---|---|
| 5542-SP30021-1 | 4.37 | 0.17 | 2.17 | 40.26 | 39.43 | 11.06 | 0.74 | 1.14 | 0.14 | 0.42 |
| 5542-SP30021-2 | 4.33 | 0.18 | 1.51 | 43.07 | 36.03 | 12.57 | 0.57 | 1.21 | 0.14 | 0.33 |
| 5542-SP30021-3 | 5.2 | 0.22 | 3.1 | 43.7 | 37.04 | 8.03 | 0.92 | 1.06 | 0.13 | 0.48 |
| 5542-SP30021-4 | 4.37 | 0.15 | 1.94 | 34.26 | 45.12 | 12.04 | 0.6 | 0.96 | 0.17 | 0.3 |
| 5542-SP30021-5 | 4.15 | 0.17 | 1.73 | 48.98 | 31.13 | 11.41 | 0.63 | 1.26 | 0.13 | 0.35 |
| 5542-SP30021-6 | 4.52 | 0.17 | 1.92 | 38.1 | 42.39 | 10.53 | 0.67 | 1.04 | 0.18 | 0.39 |
| 5542-SP30021-7 | 4.58 | 0.18 | 1.66 | 41.87 | 37.52 | 11.8 | 0.62 | 1.14 | 0.15 | 0.36 |
| 5542-SP30021-8 | 4.46 | 0.17 | 1.59 | 42.89 | 36.93 | 11.88 | 0.59 | 1.14 | 0.14 | 0.35 |
| 5542-SP30021-9 | 4.63 | 0.19 | 1.69 | 39.69 | 39.75 | 11.48 | 0.62 | 1.09 | 0.15 | 0.38 |
| 5542-SP30021-10 | 4.74 | 0.16 | 1.79 | 39.19 | 40.51 | 11.42 | 0.63 | 0.99 | 0.13 | 0.34 |
| 5542-SP30021-11 | 4.57 | 0.16 | 1.71 | 38.13 | 42 | 11.15 | 0.62 | 1.04 | 0.18 | 0.36 |
| 5542-SP30021-12 | 4.05 | 0.16 | 2.04 | 35.44 | 43.47 | 12.45 | 0.62 | 1.07 | 0.21 | 0.33 |
| 5542-SP30021-13 | 4.37 | 0.15 | 1.79 | 38.74 | 41.28 | 11.36 | 0.62 | 1.04 | 0.16 | 0.35 |
| 5542-SP30021-14 | 4.32 | 0.16 | 1.47 | 42.32 | 37.17 | 12.3 | 0.54 | 1.16 | 0.16 | 0.32 |
| 5542-SP30021-15 | 4.25 | 0.18 | 1.65 | 44.96 | 34.28 | 12.39 | 0.59 | 1.13 | 0.14 | 0.32 |
| 5542-SP30021-16 | 4.53 | 0.17 | 1.91 | 42.13 | 38.32 | 10.51 | 0.67 | 1.12 | 0.14 | 0.38 |
| 5542-SP30021-17 | 4.16 | 0.19 | 1.7 | 50.65 | 29.3 | 11.4 | 0.61 | 1.29 | 0.11 | 0.36 |
| 5542-SP30021-18 | 4.24 | 0.17 | 1.68 | 44.47 | 35.46 | 11.52 | 0.6 | 1.19 | 0.14 | 0.34 |
| 5542-SP30021-19 | 4.1 | 0.18 | 1.8 | 46.67 | 33.87 | 10.86 | 0.63 | 1.24 | 0.13 | 0.37 |
| 5542-SP30021-20 | 4.3 | 0.17 | 1.64 | 39.6 | 40.39 | 11.53 | 0.57 | 1.12 | 0.16 | 0.32 |
| SP30021 | 4.38 | 0.21 | 1.47 | 56.51 | 22.59 | 12.04 | 0.62 | 1.45 | 0.11 | 0.39 |

TABLE 9

| CYCLE ID | SPL NO | STRAIN ID | 16:0 | 16:1 | 18:0 | 18:1 | 18:2 | 18:3 | 20:0 | 20:1 | 20:2 | 22:0 |
|---|---|---|---|---|---|---|---|---|---|---|---|---|
| 97XX1156 | 96 | 5542-SP30021-4 | 3.71 | 0.13 | 1.36 | 29.29 | 51.74 | 11.57 | 0.41 | 0.85 | 0.18 | 0.46 |
| 97XX1156 | 50 | 5542-SP30021-4 | 2.95 | 0.11 | 1.33 | 28.78 | 50.97 | 13.83 | 0.3 | 0.99 | 0.28 | 0.32 |
| 97XX1158 | 10 | 5542-SP30021-4 | 4.05 | 0.16 | 2.47 | 31.18 | 50.88 | 8.77 | 0.67 | 0.89 | 0.22 | 0.33 |
| 97XX1158 | 32 | 5542-SP30021-4 | 3.56 | 0.15 | 1.44 | 30.73 | 50.1 | 11.86 | 0.47 | 0.91 | 0.21 | 0.22 |
| 97XX1158 | 56 | 5542-SP30021-4 | 4.44 | 0.19 | 3.09 | 30.64 | 49.71 | 9.39 | 0.83 | 0.79 | 0.2 | 0.4 |
| 97XX1157 | 80 | 5542-SP30021-4 | 4.05 | 0.18 | 1.32 | 27.41 | 49.59 | 14.81 | 0.53 | 1.19 | 0.29 | 0.4 |
| 97XX1158 | 39 | 5542-SP30021-4 | 4.04 | 0.15 | 2.98 | 28.62 | 49.52 | 12.28 | 0.69 | 0.86 | 0.31 | 0.27 |
| 97XX1156 | 17 | 5542-SP30021-4 | 3.65 | 0.15 | 2.43 | 29.38 | 49.42 | 12.3 | 0.52 | 0.92 | 0.67 | 0.35 |
| 97XX1156 | 60 | 5542-SP30021-4 | 3.75 | 0.17 | 1.7 | 30.03 | 49.13 | 12.87 | 0.51 | 1.01 | 0.27 | 0.35 |
| 97XX1157 | 83 | 5542-SP30021-4 | 4.15 | 0.2 | 1.77 | 29.72 | 49.08 | 12.22 | 0.66 | 1.21 | 0.16 | 0.52 |
| 97XX1157 | 86 | 5542-SP30021-4 | 3.6 | 0.14 | 1.12 | 27.65 | 49.01 | 16.05 | 0.48 | 1.21 | 0.33 | 0.08 |
| 97XX1158 | 77 | 5542-SP30021-4 | 4.14 | 0.17 | 1.58 | 31.98 | 48.82 | 10.72 | 0.65 | 1 | 0.28 | 0.44 |
| 97XX1157 | 88 | 5542-SP30021-4 | 3.36 | 0.15 | 1.22 | 56.42 | 21.63 | 13.78 | 0.58 | 1.85 | 0.06 | 0.65 |
| 97XX1157 | 39 | 5542-SP30021-12 | 2.84 | 0.04 | 1.84 | 29.6 | 53.16 | 9.52 | 0.57 | 1.32 | 0.35 | 0.48 |
| 97XX1157 | 55 | 5542-SP30021-12 | 3.28 | 0.1 | 2.18 | 30.36 | 52.27 | 9.26 | 0.63 | 1.15 | 0.22 | 0.41 |
| 97XX1157 | 10 | 5542-SP30021-12 | 3.5 | 0.06 | 1.51 | 29.78 | 50.98 | 11.13 | 0.64 | 1.45 | 0.4 | 0.26 |
| 97XX1157 | 41 | 5542-SP30021-12 | 3.31 | 0.08 | 1.64 | 30.18 | 50.51 | 11.59 | 0.57 | 1.27 | 0.24 | 0.41 |
| 97XX1157 | 35 | 5542-SP30021-12 | 3.31 | 0.09 | 1.57 | 30.36 | 50.1 | 12.17 | 0.5 | 1.15 | 0.23 | 0.35 |
| 97XX1157 | 1 | 5542-SP30021-12 | 3.45 | 0.11 | 2.88 | 32.11 | 49.45 | 8.69 | 0.82 | 1.22 | 0.27 | 0.63 |
| 97XX1157 | 16 | 5542-SP30021-12 | 2.91 | 0.09 | 1.52 | 29.35 | 48.88 | 14.26 | 0.58 | 1.39 | 0.15 | 0.3 |

TABLE 9-continued

| CYCLE ID | SPL NO | STRAIN ID | 16:0 | 16:1 | 18:0 | 18:1 | 18:2 | 18:3 | 20:0 | 20:1 | 20:2 | 22:0 |
|---|---|---|---|---|---|---|---|---|---|---|---|---|
| 97XX1157 | 50 | 5542-SP30021-12 | 3.29 | 0.09 | 2.13 | 33.23 | 48.78 | 9.87 | 0.67 | 1.06 | 0.18 | 0.47 |
| 97XX1157 | 25 | 5542-SP30021-12 | 2.83 | 0.05 | 1.4 | 33.22 | 48.52 | 11.22 | 0.5 | 1.33 | 0.26 | 0.42 |
| 97XX1157 | 57 | 5542-SP30021-12 | 2.94 | 0.13 | 1.46 | 32.85 | 47.58 | 12.21 | 0.57 | 1.31 | 0.27 | 0.47 |
| 97XX1157 | 56 | 5542-SP30021-12 | 3.01 | 0.07 | 1.63 | 31.53 | 47 | 14.02 | 0.59 | 1.31 | 0.28 | 0.23 |
| 97XX1157 | 6 | 5542-SP30021-12 | 3.9 | 0.13 | 1.5 | 32.43 | 46.98 | 12.45 | 0.52 | 1.11 | 0.21 | 0.49 |
| 97XX1157 | 18 | 5542-SP30021-12 | 3.88 | 0.16 | 1.73 | 57.94 | 22.33 | 10.51 | 0.74 | 1.68 | 0.11 | 0.64 |

Example 10

Simultaneous Expression of *M. alpina* Δ6 and Δ12 Desaturases in *Brassica napus*

In order to express the *M. alpina* Δ6 and Δ12 desaturases from the same T-DNA, the following construct for seed-specific expression was made.

The NotI fragment of pCGN5536 containing the containing the napin 5' regulatory region, the Ma524 coding region, and the napin 3' regulatory region was inserted into the NotI site of pCGN5542 to create pCGN5544. The expression modules were oriented in such a way that the direction of transcription from Ma524 and Ma648 and the nptII marker is the same.

PCGN5544 was introduced into *Brassica napus* cv.LP30108 via *Agrobacterium* mediated transformation. Mature selfed T2 seeds were collected from 16 independent LP30108 transformation events and a non-transformed control that were grown in the greenhouse. These seeds are expected to be segregating for the Δ6+Δ12 desaturase transgene. The fatty acid composition of 20-seed pools was analyzed by GC. The results are presented in Table 10. All but one of the lines (5544-LP30108-3) shows an altered oil composition as compared to the controls. GLA was produced in all but three of the lines (−3, −4, −11); two of the three without GLA (−4, −11) showed increased 18:2 indicative of expression of the Δ12 desaturase. As a group, the levels of GLA observed in plants containing the double Δ6+Δ12 construct (pCGN5544) were higher than those of plants containing pCGN5538 (Δ6 alone). In addition, levels of the $\Delta^{6,9}$ 18:2 are much reduced in the plants containing the Δ12+Δ6 as compared to Δ6 alone. Thus, the combination of Δ6 and Δ12 desaturases on one T-DNA leads to the accumulation of more GLA and fewer side products than expression of Δ6 desaturase alone. To investigate the segregation of GLA levels in the T2 seeds and to identify individual plants to be taken on to subsequent generations, half-seed analysis was done. Seeds were germinated overnight in the dark at 30 degrees on water-soaked filter paper. The outer cotyledon was excised for GC analysis and the rest of the seedling was planted in soil. Results of some of these analyses are shown in Table 11. As expected for the T2 population, levels of GLA and 18:2 are segregating in the individual seeds. GLA content of up to 60% of total fatty acids was observed in individual seeds. Individual events were selected to be grown in the greenhouse and field for production of T3 seed.

Transgenic plants including *Brassica*, soybean, safflower, corn flax and sunflower expressing the constructs of this invention can be a good source of GLA.

Typical sources of GLA such as borage produce at most 25% GLA. In contrast the plants in Table 10 contain up to 30% GLA. Furthermore, the individual seeds shown in Table 11 contain up to 60% GLA.

TABLE 10

| | 16:0 % | 16:1 % | 18:0 % | 18:1 % | 18:2 Δ6,9 % | 18:2 Δ9,12 % | 18:3 Δ6,9,12 % | 18:3 Δ9,12,15 % | 18:4 % | 20:0 % | 20:1 % | 22:0 % |
|---|---|---|---|---|---|---|---|---|---|---|---|---|
| 5544-LP30108-1 | 4.54 | 0.17 | 1.91 | 49.96 | 0 | 30.98 | 7.97 | 1.85 | 0.11 | 0.68 | 1.17 | 0.41 |
| 5544-LP30108-2 | 4.69 | 0.19 | 2.15 | 38.49 | 0 | 33.94 | 16.21 | 1.73 | 0.25 | 0.72 | 0.96 | 0.41 |
| 5544-LP30108-3 | 4.26 | 0.2 | 1.97 | 66.68 | 0 | 22.13 | 0.08 | 1.96 | 0.01 | 0.73 | 1.33 | 0.42 |
| 5544-LP30108-4 | 4.59 | 0.24 | 1.76 | 44.21 | 0 | 44.54 | 0.02 | 2.19 | 0.01 | 0.62 | 1.08 | 0.4 |
| 5544-LP30108-5 | 4.5 | 0.18 | 2.28 | 47.57 | 0 | 26.41 | 14.42 | 1.71 | 0.22 | 0.78 | 1.1 | 0.43 |
| 5544-LP30108-6 | 4.51 | 0.16 | 2.12 | 31.95 | 0.01 | 26.94 | 29.8 | 1.41 | 0.5 | 0.81 | 1.02 | 0.51 |
| 5544-LP30108-7 | 4.84 | 0.21 | 1.68 | 38.24 | 0 | 32.27 | 18.21 | 1.87 | 0.33 | 0.66 | 1.04 | 0.43 |
| 5544-LP30108-10 | 5 | 0.28 | 1.86 | 41.17 | 0 | 46.54 | 0.36 | 2.58 | 0.02 | 0.6 | 0.91 | 0.37 |
| 5544-LP30108-11 | 4.57 | 0.2 | 1.74 | 47.29 | 0 | 41.49 | 0.03 | 2.22 | 0.01 | 0.64 | 1.17 | 0.4 |
| 5544-LP30108-12 | 4.87 | 0.18 | 2.65 | 34.53 | 0 | 30.37 | 23.12 | 1.46 | 0.36 | 0.83 | 0.95 | 0.45 |
| 5544-LP30108-13 | 4.41 | 0.16 | 2.32 | 40.82 | 0.11 | 26.8 | 21.05 | 1.53 | 0.37 | 0.77 | 1.06 | 0.42 |
| 5544-LP30108-14 | 4.38 | 0.2 | 2.21 | 29.91 | 0.16 | 28.01 | 30.62 | 1.46 | 0.59 | 0.76 | 0.97 | 0.47 |
| 5544-LP30108-15 | 4.79 | 0.22 | 2.23 | 23.42 | 0.02 | 28.73 | 35.68 | 1.51 | 0.77 | 0.87 | 0.89 | 0.56 |
| 5544-LP30108-16 | 4.54 | 0.18 | 1.78 | 40.81 | 0 | 35.24 | 12.83 | 1.95 | 0.27 | 0.68 | 1.02 | 0.43 |
| 5544-LP30108-17 | 4.63 | 0.18 | 2.28 | 46.96 | 0 | 31.06 | 10.6 | 1.7 | 0.14 | 0.76 | 1.06 | 0.42 |
| 5544-LP30108-20 | 4.87 | 0.29 | 1.44 | 31.81 | 0.15 | 23.51 | 32.85 | 1.64 | 0.69 | 0.89 | 0.96 | 0.67 |
| LP30108 control | 3.89 | 0.25 | 1.19 | 67.73 | 0 | 22.46 | 0.1 | 1.97 | 0 | 0.54 | 1.32 | 0.44 |

TABLE 11

| CYCLE ID | SPL NO | STRAIN ID | 16:0 | 16:1 | 18:0 | 18:1 | 18:2 Δ6,9 | 18:2 Δ6,9,12 | 18:3 Δ6,9,12 | 18:3 Δ9,12,15 | 18:4 | 20:0 | 20:1 |
|---|---|---|---|---|---|---|---|---|---|---|---|---|---|
| 97XX1333 | 64 | 5544-LP30108-20 | 6.53 | 0.15 | 0.98 | 23.33 | 0.01 | 21.1 | 43.3 | 1.34 | 0.84 | 0.52 | 0.97 |
| 97XX1333 | 65 | 5544-LP30108-20 | 6.9 | 0.29 | 1.17 | 8.89 | 0.03 | 15.07 | 60.5 | 1.12 | 2.23 | 0.98 | 0.86 |

TABLE 11-continued

| CYCLE ID | SPL NO | STRAIN ID | 16:0 | 16:1 | 18:0 | 18:1 | 18:2 Δ6,9 | 18:2_Δ6,9,12 | 18:3_Δ6,9,12 | 18:3_Δ9,12,15 | 18:4 | 20:0 | 20:1 |
|---|---|---|---|---|---|---|---|---|---|---|---|---|---|
| 97XX1333 | 66 | 5544-LP30108-20 | 8.15 | 0.2 | 3.6 | 16.87 | 0.11 | 16.05 | 48.23 | 1.1 | 1.18 | 1.71 | 0.66 |
| 97XX1333 | 67 | 5544-LP30108-20 | 8.85 | 0.35 | 1.2 | 14.49 | 0.01 | 25.66 | 43.98 | 1.8 | 1.03 | 0.65 | 0.76 |
| 97XX1333 | 68 | 5544-LP30108-20 | 6.05 | 0.16 | 1.27 | 17.85 | 0.16 | 16.13 | 53.16 | 1.14 | 1.25 | 0.71 | 0.85 |
| 97XX1333 | 69 | 5544-LP30108-20 | 7.16 | 0.21 | 1.33 | 11.51 | 0.09 | 17.42 | 56.13 | 1.41 | 1.58 | 0.93 | 0.68 |
| 97XX1333 | 70 | 5544-LP30108-20 | 3.46 | 0.04 | 1.76 | 18.38 | 0.03 | 22.55 | 48.55 | 1.22 | 1.04 | 0.83 | 0.95 |
| 97XX1333 | 71 | 5544-LP30108-20 | 3.71 | 0.05 | 1.74 | 16.11 | 0.01 | 26.93 | 45.79 | 1.47 | 1.02 | 0.89 | 1 |
| 97XX1333 | 72 | 5544-LP30108-20 | 3.5 | 0.04 | 1.76 | 23.74 | 0.02 | 35.38 | 30.82 | 1.87 | 0.58 | 0.65 | 0.89 |
| 97XX1333 | 73 | 5544-LP30108-20 | 4.67 | 0.11 | 1.87 | 17.98 | 0.04 | 22.47 | 47.89 | 1.17 | 0.89 | 0.93 | 0.88 |
| 97XX1333 | 74 | 5544-LP30108-20 | 4.52 | 0.09 | 1.86 | 13.77 | 0.03 | 20.9 | 52.96 | 1.31 | 1.19 | 1.03 | 0.88 |
| 97XX1333 | 75 | 5544-LP30108-20 | 5.26 | 0.13 | 1.64 | 16.46 | 0.05 | 21.75 | 49.42 | 1.25 | 1.08 | 0.83 | 0.86 |
| 97XX1333 | 76 | 5544-LP30108-20 | 7.61 | 0.21 | 1.44 | 12.49 | 0.33 | 17 | 55.31 | 1.18 | 1.59 | 0.88 | 0.74 |
| 97XX1333 | 77 | 5544-LP30108-20 | 6.42 | 0.15 | 1.51 | 10.79 | 0.09 | 15.96 | 58.77 | 1.12 | 1.53 | 0.98 | 0.85 |
| 97XX1333 | 78 | 5544-LP30108-20 | 4.59 | 0.16 | 0.93 | 12.1 | 0.08 | 15.94 | 60.15 | 1.12 | 1.69 | 0.74 | 0.88 |
| 97XX1333 | 79 | 5544-LP30108-20 | 5.24 | 0.09 | 1.94 | 14.08 | 0.21 | 19.79 | 53.58 | 1.05 | 1.03 | 0.96 | 0.84 |
| 97XX1333 | 80 | 5544-LP30108-20 | 4.38 | 0.08 | 1.66 | 22.25 | 0 | 30.79 | 35.49 | 2.16 | 0.72 | 0.66 | 0.84 |
| 97XX1333 | 81 | 5544-LP30108-20 | 4.05 | 0.05 | 1.44 | 24.16 | 0.04 | 24.86 | 40.89 | 1.42 | 0.79 | 0.63 | 0.84 |
| 97XX1333 | 82 | 5544-LP30108-20 | 3.29 | 0.05 | 1.9 | 19.66 | 0 | 23.83 | 46.48 | 1.27 | 0.87 | 0.78 | 0.81 |
| 97XX1333 | 83 | 5544-LP30108-20 | 4.82 | 0.08 | 1.99 | 17.27 | 0.1 | 20.69 | 49.73 | 1.22 | 1.06 | 0.98 | 0.82 |
| 97XX1333 | 84 | 5544-LP30108-20 | 5.33 | 0.1 | 1.77 | 13.6 | 0.03 | 21.44 | 51.74 | 1.52 | 1.21 | 0.98 | 0.93 |
| 97XX1333 | 85 | 5544-LP30108-20 | 3.3 | 0.05 | 1.2 | 68.23 | 0 | 22.09 | 0.01 | 2.27 | 0 | 0.57 | 1.57 |
| 97XX1333 | 86 | 5544-LP30108-20 | 3.23 | 0.05 | 1.54 | 28.15 | 0.01 | 36.4 | 25.91 | 1.99 | 0.43 | 0.59 | 0.97 |
| 97XX1333 | 87 | 5544-LP30108-20 | 4.38 | 0.1 | 1.16 | 60.94 | 2.85 | 8.35 | 17.61 | 1.26 | 0.69 | 0.54 | 1.39 |
| 97XX1333 | 88 | 5544-LP30108-20 | 4.4 | 0.09 | 1.34 | 38.42 | 0.02 | 34.74 | 16.61 | 2.12 | 0.32 | 0.53 | 0.82 |
| 97XX1278 | 16 | 5544-LP30108-15 | 3.62 | 0.11 | 1.22 | 27.23 | 0 | 30.9 | 32.87 | 1.41 | 0.48 | 0.46 | 0.97 |
| 97XX1278 | 17 | 5544-LP30108-15 | 3.68 | 0.13 | 1.26 | 45.29 | 0 | 44.79 | 0.72 | 1.77 | 0.01 | 0.43 | 1.24 |
| 97XX1278 | 18 | 5544-LP30108-15 | 4.08 | 0.15 | 1.49 | 22.34 | 0 | 28.37 | 39.37 | 1.22 | 0.64 | 0.55 | 0.88 |
| 97XX1278 | 19 | 5544-LP30108-15 | 3.51 | 0.1 | 1.01 | 35.44 | 0 | 44.12 | 11.7 | 1.72 | 0.15 | 0.36 | 1.14 |
| 97XX1278 | 20 | 5544-LP30108-15 | 3.66 | 0.12 | 1.21 | 27.44 | 0 | 30.2 | 32.37 | 1.49 | 0.53 | 0.49 | 1.15 |
| 97XX1278 | 21 | 5544-LP30108-15 | 3.58 | 0.11 | 1.51 | 29.81 | 0 | 30.72 | 30.65 | 1.16 | 0.4 | 0.5 | 0.96 |
| 97XX1278 | 23 | 5544-LP30108-15 | 3.69 | 0.11 | 1.42 | 30.05 | 0 | 32.28 | 27.41 | 1.65 | 0.38 | 0.54 | 1.19 |
| 97XX1278 | 24 | 5544-LP30108-15 | 3.56 | 0.11 | 1.31 | 30.25 | 0 | 28.64 | 31.46 | 1.43 | 0.48 | 0.48 | 1.11 |
| 97XX1278 | 25 | 5544-LP30108-15 | 4.41 | 0.22 | 2.08 | 15.05 | 0 | 23.77 | 49.51 | 1.18 | 0.96 | 0.87 | 0.85 |
| 97XX1278 | 26 | 5544-LP30108-15 | 3.75 | 0.14 | 1.59 | 23.55 | 0 | 27.91 | 38.8 | 1.39 | 0.61 | 0.59 | 0.97 |
| 97XX1278 | 27 | 5544-LP30108-15 | 3.67 | 0.11 | 1.9 | 26.07 | 0 | 31.1 | 33.16 | 1.08 | 0.49 | 0.65 | 0.97 |
| 97XX1278 | 28 | 5544-LP30108-15 | 3.82 | 0.11 | 1.54 | 21.27 | 0 | 29.07 | 39.69 | 1.47 | 0.7 | 0.58 | 0.86 |
| 97XX1278 | 29 | 5544-LP30108-15 | 3.85 | 0.14 | 1.27 | 45.84 | 0 | 43.38 | 1 | 2.33 | 0.02 | 0.42 | 1.27 |
| 97XX1278 | 30 | 5544-LP30108-15 | 3.59 | 0.12 | 1.19 | 30.41 | 0 | 30.68 | 30.37 | 1.24 | 0.4 | 0.37 | 0.99 |
| 97XX1278 | 31 | 5544-LP30108-15 | 3.74 | 0.12 | 1.26 | 38.98 | 0 | 50.53 | 0.98 | 2.12 | 0.02 | 0.39 | 1.14 |
| 97XX1278 | 32 | 5544-LP30108-15 | 3.86 | 0.11 | 1.46 | 26.38 | 0 | 28.9 | 35.41 | 1.01 | 0.5 | 0.54 | 0.97 |

Example 11

Simultaneous Expression of *M. alpina* Δ5 and Δ6 Desaturases in *Brassica napus*

In order to produce arachadonic acid (ARA) in transgenic canola oil both Δ5 and Δ6 desaturase activities need to be introduced. In order to facilitate downstream characterization and breeding, it may be advantageous to have both activities encoded by a single T-DNA. The following example illustrates the simultaneous expression of Δ5 and Δ6 desaturases.

The Asp718 fragment of pCGN5528 containing the napin 5' regulatory region, the Ma29 coding region, and the napin 3' regulatory region was inserted into the Asp718 site of pCGN5138 to create pCGN5545. The NotI fragment of pCGN5536 containing the napin 5' regulatory region, the Ma524 coding region, and the napin 3' regulatory region was inserted into the NotI site of pCGN5545 to create pCGN5546. The expression modules were oriented in such a way that the direction of transcription from Ma524 and Ma29 and the nptII marker is the same.

PCGN5546 was introduced into *Brassica napus* cv.LP30108 via *Agrobacterium* mediated transformation. Mature selfed T2 seeds were collected from 30 independent LP30108 transformation events that were grown in the greenhouse. The fatty acid composition of 20-seed pools was analyzed by GC. The results are shown in Table 12. All the lines show expression of both desaturases as evidenced by the presence of Δ5,9 18:2 (as seen in pCGN5531 plants) and $Δ^{6,9}$ 18:2 and GLA (as seen in pCGN5538 plants)

TABLE 12 fatty acid analysis of 20-seed pools of mature T2 seeds from 5546-LP30108 events

| STRAIN ID | 16:0 | 16:1 | 18:0 | 18:1 | 18:2_Δ5,9 | 18:2_Δ6,9 | 18:2_Δ9,12 | 18:3_Δ6,9,12 | 18:3_Δ9,12,15 | 18:4 | 20:0 | 20:1 |
|---|---|---|---|---|---|---|---|---|---|---|---|---|
| 5546-LP30108-1 | 4.88 | 0.33 | 2.28 | 57.2 | 4.68 | 6.08 | 7.36 | 12.29 | 1.38 | 0.85 | 0.84 | 1.22 |
| 5546-LP30108-2 | 4.01 | 0.14 | 2.22 | 66.04 | 2.73 | 1.33 | 12.6 | 6.45 | 1.41 | 0.32 | 0.75 | 1.2 |
| 5546-LP30108-3 | 4.29 | 0.15 | 2.55 | 68.89 | 0.44 | 0.58 | 16.97 | 1.66 | 1.6 | 0.11 | 0.88 | 1.22 |
| 5546-LP30108-4 | 4.24 | 0.14 | 2.6 | 70.48 | 0.73 | 0.52 | 14.28 | 2.61 | 1.42 | 0.14 | 0.96 | 1.26 |
| 5546-LP30108-5 | 3.52 | 0.15 | 2.01 | 60.3 | 1.72 | 0.95 | 16.92 | 9.88 | 1.66 | 0.39 | 0.68 | 1.26 |
| 5546-LP30108-6 | 4.05 | 0.17 | 2.24 | 61.29 | 1.98 | 0.4 | 18.87 | 6.28 | 2 | 0.34 | 0.7 | 1.24 |
| 5546-LP30108-7 | 4.74 | 0.21 | 2.49 | 64.5 | 2.25 | 1.18 | 10.03 | 9.73 | 1.35 | 0.52 | 0.97 | 1.28 |

TABLE 12-continued fatty acid analysis of 20-seed pools of mature T2 seeds from 5546-LP30108 events

| STRAIN ID | 16:0 | 16:1 | 18:0 | 18:1 | 18:2_Δ5,9 | 18:2_Δ6,9 | 18:2_Δ9,12 | 18:3_Δ6,9,12 | 18:3_Δ9,12,15 | 18:4 | 20:0 | 20:1 |
|---|---|---|---|---|---|---|---|---|---|---|---|---|
| 5546-LP30108-8 | 4.24 | 0.14 | 2.82 | 63.92 | 1.9 | 1.5 | 11.67 | 9.29 | 1.44 | 0.43 | 0.89 | 1.19 |
| 5546-LP30108-9 | 3.8 | 0.13 | 2.15 | 65.75 | 2.3 | 0.16 | 14.92 | 6.32 | 1.57 | 0.24 | 0.75 | 1.35 |
| 5546-LP30108-10 | 4.28 | 0.17 | 1.55 | 58.8 | 1.1 | 0.12 | 22.95 | 5.97 | 2.24 | 0.22 | 0.6 | 1.35 |
| 5546-LP30108-11 | 4.25 | 0.15 | 1.82 | 63.68 | 1.01 | 0.22 | 19.42 | 4.96 | 1.81 | 0.2 | 0.67 | 1.23 |
| 5546-LP30108-12 | 3.95 | 0.14 | 2.36 | 66.9 | 1.12 | 0.01 | 19.42 | 1.59 | 1.77 | 0.04 | 0.8 | 1.21 |
| 5546-LP30108-13 | 4.18 | 0.16 | 2.17 | 66.91 | 1.38 | 0.02 | 18.84 | 1.99 | 1.74 | 0.05 | 0.77 | 1.15 |
| 5546-LP30108-14 | 4.74 | 0.26 | 1.82 | 65.29 | 1.25 | 0.27 | 16.77 | 5.3 | 1.59 | 0.25 | 0.71 | 1.32 |
| 5546-LP30108-15 | 4.3 | 0.23 | 2.54 | 65.65 | 1.67 | 0.59 | 13.15 | 7.22 | 1.54 | 0.36 | 0.88 | 1.3 |
| 5546-LP30108-16 | 4.05 | 0.17 | 2.75 | 64.13 | 2.56 | 2.8 | 9.56 | 9.31 | 1.34 | 0.53 | 0.92 | 1.28 |
| 5546-LP30108-17 | 4.06 | 0.13 | 2.85 | 65.76 | 2.09 | 1.92 | 9.65 | 9.1 | 1.23 | 0.45 | 0.92 | 1.22 |
| 5546-LP30108-18 | 4.16 | 0.25 | 2.14 | 60.68 | 1.43 | 0.02 | 24.02 | 2.62 | 2.11 | 0.09 | 0.69 | 1.26 |
| 5546-LP30108-19 | 5.77 | 0.37 | 2.15 | 56.11 | 1.6 | 0.33 | 19.34 | 9.16 | 2.37 | 0.46 | 0.73 | 1.05 |
| 5546-LP30108-20 | 5.03 | 0.36 | 2.34 | 61.05 | 1.55 | 0.35 | 17.21 | 6.96 | 2.24 | 0.39 | 0.77 | 1.22 |
| 5546-LP30108-21 | 4.52 | 0.3 | 2.71 | 62.14 | 1.33 | 0.23 | 17.62 | 6.44 | 1.88 | 0.28 | 0.88 | 1.15 |
| 5546-LP30108-22 | 5.91 | 0.44 | 2.15 | 60.12 | 1.41 | 0.36 | 17.04 | 7.75 | 1.97 | 0.36 | 0.78 | 1.07 |
| 5546-LP30108-23 | 4.28 | 0.22 | 2.44 | 66.19 | 0.93 | 0.11 | 17.03 | 4.37 | 1.67 | 0.17 | 0.82 | 1.25 |
| 5546-LP30108-24 | 4.92 | 0.33 | 2.68 | 62.6 | 1.32 | 0.36 | 16.89 | 5.82 | 2.05 | 0.3 | 0.95 | 1.19 |
| 5546-LP30108-25 | 5.42 | 0.72 | 3.15 | 47.47 | 2.66 | 4.21 | 13.51 | 16.31 | 2.14 | 0.99 | 1.18 | 1.37 |
| 5546-LP30108-26 | 3.85 | 0.22 | 2.78 | 65.02 | 1.05 | 0.05 | 18.35 | 4.36 | 1.67 | 0.12 | 0.82 | 1.18 |
| 5546-LP30108-27 | 3.86 | 0.15 | 2.76 | 65.17 | 1.11 | 0.78 | 16.24 | 5.21 | 1.53 | 0.25 | 0.93 | 1.3 |
| 5546-LP30108-28 | 5.29 | 0.42 | 1.81 | 49.12 | 1.07 | 0.09 | 30.52 | 5.21 | 3.57 | 0.44 | 0.67 | 1.23 |
| 5546-LP30108-29 | 4.4 | 0.2 | 2.38 | 65.95 | 1.05 | 0.28 | 16.31 | 4.85 | 1.64 | 0.19 | 0.85 | 1.26 |
| 5546-LP30108-30 | 3.99 | 0.19 | 2.55 | 67.47 | 0.83 | 0.11 | 17.02 | 3.18 | 1.68 | 0.13 | 0.83 | 1.23 |

Example 12

Simultaneous Expression of *M. alpina* Δ5, Δ6 and Δ12 Desaturases in *Brassica napus*

In order to achieve optimal production of ARA in transgenic canola oil both the Δ6 and Δ12 desaturase activities may need to be present in addition to the Δ5 activity. In order to facilitate downstream characterization and breeding, it may be advantageous to have all of these activities encoded by a single T-DNA. The following example illustrates the simultaneous expression of Δ5, Δ6 and Δ12 desaturases.

The HindIII fragment of pCGN5528 containing the napin 5' regulatory region, the Ma29 coding region, and the napin 3' regulatory region was inserted into the HindIII site of pCGN5544 to create pCGN5547. The expression modules were oriented in such a way that the direction of transcription from Ma29, Ma524, Ma648 and the nptII marker is the same.

PCGN5547 was introduced into *Brassica napus* cv.LP30108 via *Agrobacterium* mediated transformation. Mature selfed T2 seeds were collected from 30 independent LP30108 transformation events that were grown in the greenhouse. The fatty acid composition of 20-seed pools was analyzed by GC. The results are shown in Table 13. Twenty-seven of the lines show significant accumulation of GLA and in general the levels of GLA observed are higher than those seen in the 5546 plants that did not contain the Δ12 desaturase. The Δ12 desaturase appears to be active in most lines as evidenced by the lack of detectable Δ6,9 18:2 and elevated 18:2 levels in most plants. Small amounts of Δ5,9 18:2 are seen in the 5547 plants, although the levels are generally less than those observed in the 5546 plants. This may be due to the presence of the Δ12 desaturase which efficiently converts the 18:1 to 18:2 before it can be desaturated at the Δ5 position.

TABLE 13 fatty acid analysis of 20-seed pools of mature T2 seeds from 5547-LP30108 events

| STRAIN ID | 12:0 | 16:0 | 16:1 | 18:0 | 18:1 | 18:2_Δ5,9 | 18:2_Δ6,9 | 18:2_Δ9,12 | 18:3_Δ6,9,12 | 18:3_Δ9,12,15 | 18:4 | 20:0 | 20:1 | 22:1 | 22:2 |
|---|---|---|---|---|---|---|---|---|---|---|---|---|---|---|---|
| 5547-LP30108-1 | 0.0 | 5.38 | 0.3 | 2.23 | 64.12 | 0.01 | 0 | 22.67 | 0.44 | 2.17 | 0.07 | 0.82 | 1.11 | 0.03 | 0 |
| 5547-LP30108-2 | 0.1 | 4.45 | 0.13 | 2.29 | 51.57 | 0.16 | 0 | 33.85 | 3.18 | 1.74 | 0.03 | 0.78 | 1.02 | 0.03 | 0.02 |
| 5547-LP30108-3 | 0.0 | 4.18 | 0.12 | 2.03 | 59.61 | 0.03 | 0 | 29.44 | 0.44 | 1.64 | 0 | 0.75 | 1.15 | 0.03 | 0.01 |
| 5547-LP30108-4 | 0.0 | 4.35 | 0.15 | 2.29 | 50.59 | 0.12 | 0.01 | 37.31 | 0.85 | 1.86 | 0.02 | 0.78 | 1.02 | 0.02 | 0.01 |
| 5547-LP30108-5 | 0.0 | 4.59 | 0.14 | 1.83 | 49 | 0.25 | 0.01 | 31.65 | 8.16 | 1.86 | 0.13 | 0.68 | 1.04 | 0.02 | 0 |
| 5547-LP30108-6 | 0.0 | 4.11 | 0.15 | 2.53 | 44.3 | 0.13 | 0 | 28.12 | 15.89 | 1.94 | 0.28 | 0.82 | 1.13 | 0 | 0 |
| 5547-LP30108-7 | 0.0 | 4.27 | 0.15 | 2.55 | 39.18 | 0.12 | 0.02 | 27 | 21.72 | 1.87 | 0.45 | 0.89 | 1.08 | 0 | 0 |
| 5547-LP30108-8 | 0.0 | 4.3 | 0.14 | 2.92 | 42.83 | 0.26 | 0 | 30.81 | 14.51 | 1.49 | 0.22 | 0.89 | 1.06 | 0 | 0 |
| 5547-LP30108-9 | 0.0 | 4.46 | 0.17 | 3.13 | 44.51 | 0 | 0 | 30.12 | 12.87 | 1.76 | 0.22 | 0.98 | 1.12 | 0.01 | 0 |
| 5547-LP30108-10 | 0.0 | 4.28 | 0.11 | 2.62 | 41.44 | 0.28 | 0 | 30.89 | 16.28 | 1.45 | 0.21 | 0.82 | 1.06 | 0 | 0 |
| 5547-LP30108-11 | 0.0 | 4.47 | 0.17 | 2.43 | 26.96 | 0.48 | 0 | 34.44 | 25.01 | 2.14 | 0.63 | 0.84 | 0.99 | 0 | 0 |
| 5547-LP30108-12 | 0.0 | 4.36 | 0.16 | 2.68 | 42.2 | 0.17 | 0 | 29.78 | 15.93 | 1.83 | 0.27 | 0.88 | 1.06 | 0 | 0 |
| 5547-LP30108-13 | 0.0 | 4.87 | 0.19 | 2.81 | 21.7 | 0.53 | 0 | 32.83 | 30.54 | 2.04 | 0.8 | 1 | 0.89 | 0.02 | 0.01 |
| 5547-LP30108-14 | 0.0 | 4.61 | 0.25 | 2.6 | 54 | 0 | 0 | 32.98 | 0.5 | 2.46 | 0.03 | 0.86 | 1.14 | 0 | 0 |
| 5547-LP30108-15 | 0.0 | 4.07 | 0.14 | 2.98 | 37.09 | 0.14 | 0.01 | 29.01 | 21.55 | 1.66 | 0.38 | 1.06 | 1.11 | 0 | 0 |
| 5547-LP30108-16 | 0.0 | 3.63 | 0.13 | 2.12 | 64.69 | 0 | 0 | 24.21 | 0.15 | 2.04 | 0 | 0.82 | 1.56 | 0.02 | 0 |
| 5547-LP30108-17 | 0.0 | 3.85 | 0.18 | 2.22 | 67.22 | 0.01 | 0 | 21.25 | 0 | 2.27 | 0 | 0.83 | 1.53 | 0 | 0 |
| 5547-LP30108-18 | 0.0 | 5.46 | 0.19 | 2.87 | 41.83 | 0.1 | 0.04 | 22.76 | 21.45 | 1.72 | 0.48 | 1.06 | 1.23 | 0 | 0 |
| 5547-LP30108-19 | 0.0 | 4.33 | 0.12 | 2.73 | 50.31 | 0.07 | 0 | 24.77 | 12.72 | 1.62 | 0.21 | 1.04 | 1.29 | 0 | 0.01 |
| 5547-LP30108-20 | 0.0 | 4.22 | 0.12 | 2.91 | 46.33 | 0.25 | 0 | 26.87 | 14.65 | 1.61 | 0.22 | 0.98 | 1.18 | 0 | 0 |

TABLE 13-continued fatty acid analysis of 20-seed pools of mature T2 seeds from 5547-LP30108 events

| STRAIN ID | 12:0 | 16:0 | 16:1 | 18:0 | 18:1 | 18:2 Δ5,9 | 18:2 Δ6,9 | 18:2 Δ9,12 | 18:3 Δ6,9,12 | 18:3 Δ9,12,15 | 18:4 | 20:0 | 20:1 | 22:1 | 22:2 |
|---|---|---|---|---|---|---|---|---|---|---|---|---|---|---|---|
| 5547-LP30108-21 | 0.0 | 4.38 | 0.17 | 2.37 | 55.37 | 0 | 0 | 32.59 | 0.53 | 1.85 | 0.03 | 0.83 | 1.23 | 0 | 0 |
| 5547-LP30108-22 | 0.0 | 5.5 | 0.18 | 2.71 | 41.93 | 0.1 | 0.19 | 24.19 | 20.14 | 1.76 | 0.45 | 0.94 | 1.21 | 0 | 0 |
| 5547-LP30108-23 | 0.0 | 4.03 | 0.16 | 2.17 | 68.44 | 0 | 0 | 20.09 | 0 | 2.19 | 0.02 | 0.83 | 1.46 | 0 | 0 |
| 5547-LP30108-24 | 0.0 | 4.19 | 0.17 | 2.72 | 49.31 | 0 | 0 | 30.38 | 8.64 | 1.85 | 0.13 | 0.86 | 1.16 | 0 | 0 |
| 5547-LP30108-25 | 0.0 | 4.04 | 0.17 | 2.1 | 70.48 | 0 | 0 | 18.04 | 0.05 | 2.09 | 0 | 0.86 | 1.54 | 0 | 0 |
| 5547-LP30108-26 | 0.0 | 4.74 | 0.22 | 3.2 | 26.74 | 0.33 | 0 | 30.05 | 28.95 | 2.02 | 0.78 | 1.08 | 0.99 | 0 | 0 |
| 5547-LP30108-27 | 0.0 | 4.29 | 0.18 | 2.23 | 52.49 | 0 | 0 | 28.48 | 7.36 | 1.91 | 0.13 | 0.87 | 1.37 | 0 | 0 |
| 5547-LP30108-28 | 0.0 | 4.36 | 0.17 | 3 | 44.35 | 0.2 | 0 | 29.59 | 13.39 | 1.91 | 0.23 | 0.96 | 1.17 | 0 | 0 |
| 5547-LP30108-29 | 0.0 | 4.32 | 0.17 | 2.94 | 52.53 | 0.05 | 0 | 33.88 | 0.91 | 2.34 | 0.01 | 0.97 | 1.23 | 0 | 0 |
| 5547-LP30108-30 | 0.0 | 4.07 | 0.14 | 2.89 | 45.13 | 0.01 | 0 | 29.06 | 13.96 | 1.71 | 0.2 | 0.94 | 1.2 | 0.01 | 0 |

Example 13

Stereospecific Distribution of Δ6-Desaturated Oils

This experiment was designed to investigate the stereospecific distribution of the Δ6-desaturated oils in seeds expressing pCGN5538 (Ma 524 cDNA). Three seed samples were used:

1) Non-transformed *B. napus* cv. LP004 seeds (control)

2) Segregating T2 seeds of pCGN5538-LP004-19

3) Segregating T2 seeds of pCGN5538-LP004-29

The following protocol was used for the analysis:

1. Seed Oil Extraction

Fifty seeds were placed in a 12×32 mm vial and crushed with a glass rod. 1.25 mL hexane was added and the mixture was vortexed. The seeds were extracted overnight on a shaker. The extract was then filtered through a 0.2 micron filter attached to a 1 cc syringe. The extract was then dried down under nitrogen. The resulting oil was used for digestion and derivatization of the whole oil sample.

2. Digestion

A. Liquid Oil Digestion

The stock lipase (from *Rhizopus arrhizus*, Sigma, L4384) was diluted to approximately 600,000 units/mL with a goal of obtaining 50% digestion of the TAG. The stock lipase is maintained at 4 degrees C. and placed on ice. The amount of reagents may be adjusted according to the amount of oil to be digested.

The following amounts are based on a 2.0 mg extracted oil sample. In a 12×32 mm screw cap vial the following were added: 2.0 mg oil, 200 µL, 0.1 M tris HCl pH 7, 40 µL 2.2 w/v % CaCl$_2$ 2H$_2$O, and 100 µL 0.05 w/v % bile salts. The material was vortexed and sonicated to disperse the oil. Twenty µL of diluted lipase was added and the mixture was vortexed continuously for 1.0 minute at room temperature. A white precipitate formed. The reaction was stopped with 100 uL 6M HCl and vortexing. Five hundred uL CHCl$_3$:CH$_3$OH (2:1) was added and the mixture was vortexed and held on ice while reaining digestions were carried out. Samples were vortexed again and centrifuged briefly to sharpen layers. The lower layer containing digest products was removed with a pasteur pipette and placed in a 12×32 mm crimp cap vial. The material was then re-extracted with 300 µL CHCl$_3$, vortexed, centrifuged, and combined with the lower layers. The digest products were kept on ice as much as possible. HPLC separation is performed as soon as possible after digestion to minimize acyl migration.

B. Solid Fat Digestion

The procedure for liquid oil digestion described above was followed except that 20 µl 11:0 methyl ester is added to 2.0 mg solid fat.

3. HPLC Separation

The digestion products were dried down in chloroform to approximately 200 µL. Each sample was then transferred into an insert in an 8×40 mm shell vial and 30 µL was injected for HPLC analysis.

The high performance liquid chromatographic system was equipped with a Varex ELSD IIA evaporative light scattering detector with tube temperature at 105° C. and nitrogen gas flow at 40 mL/min; a Waters 712 Wisp autosampler, three Beckman 114M Solvent Delivery Modules; a Beckman 421A controller, a Rheodyne pneumatically actuated stream splitter; and a Gilson micro fractionator. The chromatography column is a 220×4.6 mm, 5 micron normal phase silica cartridge by Brownlee.

The three solvents used were:
A=hexane:toluene 1:1
B=toluene:ethyl acetate 3:1
C=5% formic acid in ethyl acetate The gradient profile was as follows:

| Time (mm) | Function | Value | Duration |
|---|---|---|---|
| 0 flow | 2.0 mL/min | | |
| 0% B | 10 | | |
| 0% C | 2 | | |
| 2% C | 25 | | 6 min |
| 14.0% C | 2 | | 1 min |
| 15.0 | End program | | |

A chromatographic standard mixture is prepared in hexane:toluene 1:1 containing the following:

0.2 mg/mL triglyceride 16:0

2.0 mg/mL 16:0 Free Fatty Acid 0.2 mg/mL di16:0 mixed isomers (1,2-diacylglycerol and 1,3-diacylglycerol)

0.2 mg/mL 3-mono acylglycerol 16:0

0.2 mg/mL 2-mono acylglycerol 16:0

For each sample, the fraction containing the 2-mag peak is collected automatically by method controlled timed events relays. A time delay is used to synchronize the detector with the collector's emitter. The 2-mag peaks are collected and the fractions are evaporated at room temperature overnight.

The sn-2 composition results rely on minimization of acyl migration. Appearance of 1-monoacylglycerol and/or 3-monoacylglycerol peaks in the chromatograph means that acyl migration has occurred.

4. Derivatization

To derivatize the whole oil, 1.0 mg of the extracted whole oil was weighed into a 12×32 mm crimp cap vial. One mL toluene was then added. The sample is then vortexed and a 50 µL aliquot was removed for derivatization. To the dried down 2-mag samples, 50 µL toluene was added. To both the whole oil and 2-mag fractions 105 uL $H_2SO_4/CH_3OH$@8.76 wt % is added. The cap was tightly capped and the sample is refluxed for 1 hour at 95 degrees C. The sample was allowed to cool and 500 uL 10 w/v % NaCl in water and 60 uL heptane was added. The organic layer was removed and inserted in a 12×32 mm crimp cap vial.

5. GLC Analysis

A Hewlett Packard model 6890 GC equipped with a split/splitless capillary inlet, FID detector, 6890 series autosampler and 3392A Alpha Omega integrator is set up for the capillary column as follows:

A. Supelco Omegawax 250, 30 m length, 0.25 mm id, 0.25 um film thickness

| | |
|---|---|
| injection port: | 260 C. |
| detector: | 270 C. |
| initial temp: | 170 C. |
| initial time: | 1.5 min |
| rate: | 30 deg/min |
| final temp: | 245 C. |
| final time: | 6.5 min |
| injection vol: | 1.5 uL |
| head pressure: | 25 psi |
| split ratio: | 30 |
| carrier gas: | He |
| make-up gas: | $N_2$ |
| FID gas: | H + air |

Percent compositions of fatty acid methyl esters are calculated as mole percents. For carbon chain lengths less than 12, the use of theoretical or empirical response factors in the area percent calculation is desirable.

6. Calculations

The mean distribution of each acyl group at each sn-1 and sn-3 position was calculated.

mean sn-1 and sn-3 composition=(3 WO comp−MAG comp)/2

WO=whole oil

MAG=monoacylglycerol

The results of this analysis are presented in Table 14. The GLA and $Δ^{6,9}$ 18:2 are evenly distributed between the sn-2 and sn-1, 3 positions. This analysis can not discriminate between fatty acids in the sn-1 vs. sn-3 positions.

TABLE 14

| | 16:0 | 16:1 | 18:0 | 18:1 | 18:2_Δ6,9 | 18:2 | 18:3_Δ6,9,12 | 8:3 | 18:4 | 20:0 | 20:1 |
|---|---|---|---|---|---|---|---|---|---|---|---|
| Control | | | | | | | | | | | |
| sn2 composition | 1.23 | 0.15 | 0.37 | 64.77 | 0.00 | 29.45 | 0.06 | 2.01 | 0.00 | 0.21 | 0.57 |
| whole oil composition | 4.33 | 0.20 | 3.32 | 69.29 | 0.18 | 18.51 | 0.00 | 1.35 | 0.06 | 0.91 | 1.17 |
| mean sn1, sn3 composition* | 5.88 | 0.23 | 4.80 | 71.55 | 0.27 | 13.04 | −0.03 | 1.02 | 0.09 | 1.26 | 1.47 |
| 5538-19 | | | | | | | | | | | |
| sn2 composition | 1.65 | 0.27 | 4.12 | 57.21 | 5.61 | 14.55 | 12.45 | 1.38 | 0.32 | 0.43 | 1.00 |
| whole oil composition | 5.44 | 0.33 | 4.09 | 57.51 | 4.53 | 10.57 | 13.16 | 1.03 | 0.50 | 1.07 | 1.07 |
| mean sn1, sn3 composition* | 7.34 | 0.36 | 4.08 | 57.66 | 3.99 | 8.58 | 13.52 | 0.86 | 0.59 | 1.39 | 1.11 |
| 5538-29 | | | | | | | | | | | |
| sn2 composition | 1.24 | 0.27 | 1.56 | 56.35 | 6.35 | 17.85 | 12.99 | 1.60 | 0.38 | 0.14 | 0.40 |
| whole oil composition | 4.96 | 0.32 | 3.73 | 54.92 | 4.99 | 12.11 | 13.66 | 1.10 | 0.50 | 0.99 | 1.11 |
| mean sn1, sn3 composition* | 6.82 | 0.35 | 4.82 | 54.21 | 4.31 | 9.24 | 14.00 | 0.85 | 0.56 | 1.42 | 1.47 |

*calculated from the mag and whole oil composition for each analyte

Example 14

Fatty Acid Compositions of Transgenic Plants

Δ5 and Δ6 transgenic plants were analyzed for their fatty acid content.

The following protocol was used for oil extraction:
1. About 400 mg of seed were weighed out in duplicate for each sample.
2. The seeds were crushed in a motar and pestle. The mortar and pestle was rinsed twice with 3 ml (2:1) (v:v) $CHCl_3:CH_3OH$/MeOH. An additional 6 ml (2:1) was added to the 20 ml glass vial (oil extracted in 12 ml total 2:1).
3. Samples were vortexed and placed on an orbital shaker for 2 hours with occasional vortexing.
4. 5 ml of 1M NaCl was added to each sample. Sample was vortexed then spun in centrifuge at 2000 rpm for 5 minutes. Lower phase was drawn off using a pasteur pipette.
5. Upper phase was re-extracted with an additional 5 ml. Sample was vortexed then spun in centrifuge at 2000 rpm for 5 minutes. The lower phase was drawn off using a pasteur pipette and added to previous lower phase.
6. $CHCl_3:CH_3OH$/MeOH was evaporated under nitrogen using evaporative cooling. Vial containing extracted oil was sealed under nitrogen. Between 120 mg-160 mg oil was extracted for each sample.

For GC-MS analysis, fatty acid methyl esters were dissolved in an appropriate volume of hexane and analyzed using a Hewlett-Packard 5890 Series II Plus gas chromatograph (Hewlett Packard, Palo Alto, Calif.) equipped with a 30 m×0.32 mm i.d. Omegawax 320 fused sillica capillary column (Supelco, Bellefonte, Pa.) and a Hewlett-Packard 5972

Series mass selective detector. Mass spectra were interpreted by comparison to the mass spectra in NIST/EPA/NIH Chemical Structure Database using a MS Chem Station (#G1036A) (Hewlett Packard).

Transgenic line 5531-6 was analyzed in duplicate (A, B) and compared to control line LP004-6. The fatty acid profile results are shown in Table 15.

Transgenic line 5538-19 was analyzed in duplicate (A, B) and compared to control line LP004-6. The fatty acid profile results are shown in Table 16.

TABLE 15

Fatty Acid Profile

| | CONTROL LP004-6A LRL-2043 001f0102.d | CONTROL LP004-6B LRL-2044 001f0103.d | TRANSGENIC 5531-6A LRL-2042 001f0101.d | TRANSGENIC 5531-6B LRL-2045 001f0104.d |
|---|---|---|---|---|
| C12:0 | | | | |
| C13:0 | | | | |
| C14:0 | | 0.053 | | 0.061 |
| C14:1 | | | | |
| C15:0 isomer | | | | |
| C15:0 | | | | |
| C16:0 | 4.107 | 4.034 | 4.257 | 4.224 |
| C16:1 | 0.181 | 0.173 | 0.200 | 0.199 |
| C16:2 | 0.061 | 0.065 | 0.081 | 0.060 |
| C17:0 | | | | |
| C16:3 | 0.244 | 0.246 | 0.155 | 0.151 |
| C16:4 | | | | |
| C18:0 | 2.608 | 2.714 | 3.368 | 3.417 |
| C18:1w9 | 65.489 | 66.454 | 59.529 | 59.073 |
| C18:1w7 | 2.297 | 2.185 | 2.388 | 2.393 |
| C18:2 5, 9 | | | 6.144 | 6.269 |
| C18:2w6 | 19.828 | 18.667 | 18.872 | 19.059 |
| C18:3 5, 9, 12 | | | 0.469 | 0.496 |
| C18:3w6 | | 0.060 | | |
| C18:3w3 | 1.587 | 1.578 | 1.428 | 1.418 |
| C18:4w6 | | | | |
| C18:4w3 | | | | |
| C20:0 | 0.962 | 0.998 | 1.009 | 1.022 |
| C20:1w11 | 1.336 | 1.335 | 1.058 | 1.065 |
| C20:1w9 | | | | |
| C20:1w7 | | | 0.076 | 0.080 |
| C20:2w6 | 0.073 | 0.073 | | 0.052 |
| C20:3w6 | | | | |
| C20:4w6 | | | | |
| C20:3w3 | | | | |
| C20:4w3 | | | | |
| C20:5w3 | | | | |
| C22:0(1.000) | 0.542 | 0.558 | 0.463 | 0.467 |
| C22:1w11 | | 0.038 | | |
| C22:1w9 | | | | |
| C22:1w7 | | 0.034 | | |
| C21:5 | | | | |
| C23:0 | | 0.029 | | |
| C22:4w6 | | | | |
| C22:5w6 | | | | |
| C22:5w3 | | | | |
| C24:0 | 0.373 | 0.391 | 0.280 | 0.283 |
| C22:6w3 | 0.314 | 0.317 | 0.223 | 0.212 |
| C24:1w9 | | | | |
| TOTAL | 100.00 | 100.00 | 100.00 | 100.00 |

TABLE 16

Fatty Acid Profile

| | 5538-19A TRANSGENIC LRL-2166 | 5538-19B TRANSGENIC LRL-2167 | LP004-6A CONTROL LRL-2168 | LP004-6B CONTROL LRL-2169 |
|---|---|---|---|---|
| C6:0 | 0.004 | 0.005 | | |
| C8:0 | 0.007 | 0.007 | 0.004 | 0.005 |
| C10:0 | 0.012 | 0.012 | 0.008 | 0.008 |
| C12:0 | 0.020 | 0.020 | 0.011 | 0.012 |
| C13:0 | | | | |
| C14:0 | 0.099 | 0.108 | 0.050 | 0.050 |
| C14:1w5 | | | | |
| C15:0 | 0.059 | 0.068 | 0.017 | 0.019 |
| C16:0 | 5.272 | 5.294 | 4.049 | 4.057 |
| C16:1 | 0.350 | 0.417 | 0.197 | 0.208 |
| C16:2 | 0.199 | 0.187 | 0.076 | 0.077 |
| C17:0 | 0.092 | 0.089 | 0.078 | 0.077 |
| C16:3 | 0.149 | 0.149 | 0.192 | 0.198 |
| C16:4 | | 0.010 | | |
| C18:0 | 3.815 | 3.771 | 2.585 | 2.638 |
| C18:1 | 57.562 | 57.051 | 68.506 | 68.352 |
| C18:2 (6, 9) | 4.246 | 4.022 | | |
| C18:2w6 | 10.900 | 11.589 | 19.098 | 19.122 |
| C18:2w3 | 0.020 | 0.008 | 0.008 | 0.009 |
| C18:3w6 | 12.565 | 12.595 | 0.013 | 0.015 |
| C18:3w3 | 1.084 | 1.137 | 1.501 | 1.542 |
| C18:4 | 0.017 | 0.013 | 0.011 | 0.008 |
| C18:4 | 0.028 | 0.024 | | |
| C20:0 | 1.138 | 1.104 | 0.937 | 0.943 |
| C20:1 | 1.115 | 1.085 | 1.330 | 1.327 |
| C20:2w6 | 0.150 | 0.143 | 0.068 | 0.071 |
| C20:3w6 | 0.026 | 0.025 | 0.014 | 0.012 |
| C20:4w6 | | | | |
| C20:3w3 | | | | |
| C20:4w3 | | | | |
| C20:5w3 | | | | |
| C22:0 | 0.506 | 0.484 | 0.535 | 0.539 |
| C22:1 | 0.017 | 0.020 | 0.032 | 0.032 |
| C21:5 | | 0.040 | 0.030 | 0.031 |
| C22:4w6 | 0.038 | 0.064 | 0.015 | 0.014 |
| C22:5w6 | | | | |
| C22:5w3 | 0.023 | 0.018 | 0.021 | 0.017 |
| C24:0 | 0.352 | 0.321 | 0.353 | 0.362 |
| C22:6w3 | 0.009 | | | |
| C24:1w9 | 0.129 | 0.121 | 0.260 | 0.255 |
| TOTAL | 100.00 | 100.00 | 100.00 | 100.00 |

Example 15

Combined Expression of Δ6 and Δ12 Desaturases in
*B. napus* Achieved by Crossing Plants containing either the Δ6 or the Δ12 desaturase were crossed and individual F1 half-seeds were analyzed for fatty acid composition by GC. Data from one such cross are given in Table 17. The parents for the cross were 5538-LP004-25-2-25 (Δ6 expressor) and 5542-SP30021-10-16 (Δ12 expressor). Reciprocal crosses were made and the results of 25 individual F1 seeds of each are shown in the table. Crosses are described such that the first parent indicated is the female. Both sets of crosses gave approximately the same results. Compared to the parents, the $\Delta^{6,9}$ 18:2 decreased, and the GLA increased. $\Delta^{9,12}$ 18:2 levels are increased in most of the F1's as well. Note that these are F1 seeds and only contain one set of each desaturase. In future generations and selection of events homozygous for each desaturase, the F2 GLA levels obtained may be even higher.

Combining traits by crossing may be preferable to combining traits on one T-DNA in some situations. Particularly if both genes are driven off of the same promoter (in this case napin), issues of promoter silencing may favor this approach over putting multiple cDNAs on one construct.

Alternatively, in some cases, combining multiple cDNAs on one T-DNA may be the method of choice. The results are shown in Table 17.

For seed specific expression, the coding regions of the desaturase cDNAs are placed under control of the 5' regulatory region of *Glycine max* alpha-type beta conglycinin storage protein gene. The specific region that can be used is nucleotides 78-921 of gi 169928 (Doyle, J. J., Schuler, M. A.,

TABLE 17

| STRAIN ID | 16:0 | 16:1 | 18:0 | 18:1 | 18:2_ Δ6,9 | 18:2_ Δ9,12 | 18:3_ Δ6,9,12 | 18:3_ Δ9,12,11 | 18:4 | 20:0 | 20:1 |
|---|---|---|---|---|---|---|---|---|---|---|---|
| 5538-LP004-25-2-25 | 4.23 | 0.13 | 2.4 | 61.78 | 8.77 | 6.34 | 11.58 | 0.92 | 0 | 0 | 0 |
| 5542-SP30021-10-16 | 4.09 | 0.1 | 2.03 | 38.4 | 0 | 41.88 | 0 | 11.06 | 0.02 | 0.75 | 1.03 |
| (5538-LP004-25-2-25 × 5542-SP30021-10-16) | 3.9 | 0.04 | 2.31 | 38.58 | 0 | 27.91 | 20.94 | 2.67 | 0.65 | 0.92 | 1.28 |
| (5538-LP004-25-2-25 × 5542-SP30021-10-16) | 3.5 | 0.04 | 1.88 | 36.24 | 0 | 28.68 | 22.54 | 3.36 | 0.85 | 0.78 | 1.32 |
| (5538-LP004-25-2-25 × 5542-SP30021-10-16) | 3.51 | 0.03 | 1.98 | 38.36 | 0 | 29.48 | 19.95 | 3.06 | 0.68 | 0.79 | 1.38 |
| (5538-LP004-25-2-25 × 5542-SP30021-10-16) | 3.95 | 0.04 | 1.86 | 38.65 | 0 | 28.08 | 20.81 | 2.92 | 0.75 | 0.76 | 1.42 |
| (5538-LP004-25-2-25 × 5542-SP30021-10-16) | 4.26 | 0.05 | 2.44 | 40.25 | 0.01 | 28.81 | 18.08 | 2.74 | 0.53 | 0.88 | 1.24 |
| (5538-LP004-25-2-25 × 5542-SP30021-10-16) | 4.13 | 0.04 | 2.33 | 34.48 | 0 | 26.73 | 26.2 | 2.32 | 0.75 | 0.9 | 1.27 |
| (5538-LP004-25-2-25 × 5542-SP30021-10-16) | 3.8 | 0.04 | 2.15 | 38.34 | 0 | 28.95 | 20.64 | 2.63 | 0.65 | 0.81 | 1.3 |
| (5538-LP004-25-2-25 × 5542-SP30021-10-16) | 3.96 | 0.05 | 1.59 | 36.43 | 0 | 29.05 | 21.85 | 3.47 | 0.86 | 0.68 | 1.32 |
| (5538-LP004-25-2-25 × 5542-SP30021-10-16) | 4.04 | 0.04 | 2.5 | 37.75 | 0 | 27.23 | 22.89 | 1.95 | 0.55 | 0.99 | 1.26 |
| (5538-LP004-25-2-25 × 5542-SP30021-10-16) | 3.53 | 0.04 | 1.8 | 34.88 | 0 | 29.17 | 23.42 | 3.42 | 0.9 | 0.74 | 1.3 |
| (5538-LP004-25-2-25 × 5542-SP30021-10-16) | 3.43 | 0.04 | 1.89 | 37.12 | 0 | 29.52 | 20.91 | 3.35 | 0.8 | 0.79 | 1.35 |
| (5538-LP004-25-2-25 × 5542-SP30021-10-16) | 3.58 | 0.03 | 2.55 | 39.54 | 0 | 28.81 | 19.34 | 2.44 | 0.54 | 0.98 | 1.34 |
| (5538-LP004-25-2-25 × 5542-SP30021-10-16) | 3.53 | 0.03 | 2.33 | 39.26 | 0 | 29.07 | 19.5 | 2.61 | 0.59 | 0.91 | 1.37 |
| (5538-LP004-25-2-25 × 5542-SP30021-10-16) | 3.4 | 0.02 | 2.41 | 45.53 | 0 | 28.94 | 13.71 | 2.51 | 0.37 | 0.91 | 1.44 |
| (5538-LP004-25-2-25 × 5542-SP30021-10-16) | 3.49 | 0.03 | 2.57 | 40.95 | 0 | 28.52 | 17.97 | 2.63 | 0.58 | 0.99 | 1.43 |
| (5538-LP004-25-2-25 × 5542-SP30021-10-16) | 3.65 | 0.04 | 2.11 | 38.02 | 0 | 29.13 | 20.53 | 2.85 | 0.66 | 0.86 | 1.33 |
| (5538-LP004-25-2-25 × 5542-SP30021-10-16) | 3.97 | 0.03 | 1.99 | 34.95 | 0.01 | 27.15 | 25.71 | 2.38 | 0.79 | 0.81 | 1.38 |
| (5538-LP004-25-2-25 × 5542-SP30021-10-16) | 3.81 | 0.05 | 1.46 | 38.3 | 0 | 31.51 | 17.67 | 3.83 | 0.75 | 0.61 | 1.33 |
| (5538-LP004-25-2-25 × 5542-SP30021-10-16) | 3.98 | 0.05 | 2.03 | 37.14 | 0 | 30.09 | 20.28 | 2.79 | 0.72 | 0.8 | 1.36 |
| (5538-LP004-25-2-25 × 5542-SP30021-10-16) | 4.03 | 0.04 | 2.52 | 42.9 | 0 | 27.79 | 16.66 | 2.64 | 0.54 | 0.9 | 1.29 |
| (5538-LP004-25-2-25 × 5542-SP30021-10-16) | 4.03 | 0.04 | 2.27 | 40.72 | 0 | 29.37 | 17.56 | 2.53 | 0.53 | 0.86 | 1.35 |
| (5538-LP004-25-2-25 × 5542-SP30021-10-16) | 3.98 | 0.04 | 2.61 | 39.91 | 0 | 28.06 | 19.15 | 2.69 | 0.6 | 0.96 | 1.26 |
| (5538-LP004-25-2-25 × 5542-SP30021-10-16) | 3.73 | 0.03 | 1.89 | 40.22 | 0 | 29.44 | 18.21 | 3 | 0.67 | 0.73 | 1.39 |
| (5538-LP004-25-2-25 × 5542-SP30021-10-16) | 4.02 | 0.04 | 2.14 | 42.58 | 0 | 30.36 | 15.18 | 2.43 | 0.42 | 0.82 | 1.3 |
| (5542-SP30021-10-16 × 5538-LP004-25-2-25) | 4.14 | 0.06 | 2.23 | 30.67 | 0 | 30.38 | 25.47 | 3.12 | 0.91 | 0.9 | 1.29 |
| (5542-SP30021-10-16 × 5538-LP004-25-2-25) | 4.05 | 0.07 | 1.7 | 37.03 | 0.04 | 32.1 | 15.97 | 5.38 | 0.96 | 0.69 | 1.28 |
| (5542-SP30021-10-16 × 5538-LP004-25-2-25) | 4.01 | 0.07 | 1.58 | 38.02 | 0.05 | 33.65 | 13.92 | 5.15 | 0.89 | 0.66 | 1.28 |
| (5542-SP30021-10-16 × 5538-LP004-25-2-25) | 4.07 | 0.06 | 2.01 | 31.63 | 0.05 | 31.13 | 23.09 | 3.94 | 1.1 | 0.83 | 1.28 |
| (5542-SP30021-10-16 × 5538-LP004-25-2-25) | 4.03 | 0.05 | 1.94 | 31.88 | 0 | 30.98 | 23.71 | 3.45 | 0.99 | 0.82 | 1.3 |
| (5542-SP30021-10-16 × 5538-LP004-25-2-25) | 3.92 | 0.06 | 1.71 | 35.77 | 0.03 | 33.15 | 16.39 | 5.28 | 0.98 | 0.68 | 1.32 |
| (5542-SP30021-10-16 × 5538-LP004-25-2-25) | 4.09 | 0.08 | 1.57 | 34.6 | 0.03 | 33.73 | 16.73 | 5.48 | 0.99 | 0.66 | 1.28 |
| (5542-SP30021-10-16 × 5538-LP004-25-2-25) | 3.94 | 0.07 | 1.59 | 34.03 | 0.04 | 31.35 | 19.76 | 5.29 | 1.22 | 0.67 | 1.28 |
| (5542-SP30021-10-16 × 5538-LP004-25-2-25) | 4.13 | 0.06 | 1.85 | 31.44 | 0.06 | 31.28 | 23.77 | 3.52 | 1.04 | 0.79 | 1.22 |
| (5542-SP30021-10-16 × 5538-LP004-25-2-25) | 4.14 | 0.06 | 1.96 | 31.11 | 0.04 | 31.88 | 23.3 | 3.6 | 1.01 | 0.82 | 1.27 |
| (5542-SP30021-10-16 × 5538-LP004-25-2-25) | 3.98 | 0.07 | 1.58 | 35.06 | 0 | 32.06 | 18.1 | 5.33 | 1.12 | 0.67 | 1.28 |
| (5542-SP30021-10-16 × 5538-LP004-25-2-25) | 3.89 | 0.06 | 1.59 | 32.51 | 0.05 | 29.44 | 22.91 | 5.33 | 1.54 | 0.67 | 1.25 |
| (5542-SP30021-10-16 × 5538-LP004-25-2-25) | 4 | 0.07 | 1.69 | 32.1 | 0.05 | 30.49 | 22.77 | 4.66 | 1.32 | 0.75 | 1.26 |
| (5542-SP30021-10-16 × 5538-LP004-25-2-25) | 4.06 | 0.05 | 1.93 | 30.77 | 0.07 | 28.37 | 27.21 | 3.37 | 1.19 | 0.84 | 1.25 |
| (5542-SP30021-10-16 × 5538-LP004-25-2-25) | 4.1 | 0.06 | 1.9 | 31.77 | 0.05 | 32.33 | 22.03 | 3.92 | 0.98 | 0.78 | 1.27 |
| (5542-SP30021-10-16 × 5538-LP004-25-2-25) | 3.94 | 0.07 | 1.67 | 34.74 | 0.03 | 33.63 | 17.1 | 5.16 | 0.99 | 0.68 | 1.26 |
| (5542-SP30021-10-16 × 5538-LP004-25-2-25) | 3.71 | 0.06 | 1.65 | 33.05 | 0 | 33.22 | 19.73 | 4.7 | 1.07 | 0.68 | 1.39 |
| (5542-SP30021-10-16 × 5538-LP004-25-2-25) | 3.84 | 0.06 | 1.71 | 34.16 | 0.04 | 34.52 | 16.74 | 5.18 | 0.97 | 0.68 | 1.34 |
| (5542-SP30021-10-16 × 5538-LP004-25-2-25) | 4 | 0.07 | 1.66 | 34.97 | 0.07 | 33.08 | 17.07 | 5.27 | 1.1 | 0.67 | 1.28 |
| (5542-SP30021-10-16 × 5538-LP004-25-2-25) | 4.16 | 0.06 | 1.99 | 35.44 | 0.05 | 31.89 | 18.95 | 3.68 | 0.89 | 0.81 | 1.29 |
| (5542-SP30021-10-16 × 5538-LP004-25-2-25) | 4.05 | 0.08 | 1.46 | 33.49 | 0 | 31.96 | 18.81 | 6.2 | 1.32 | 0.61 | 1.28 |
| (5542-SP30021-10-16 × 5538-LP004-25-2-25) | 4.2 | 0.06 | 1.93 | 35.06 | 0.06 | 33.69 | 17.38 | 4 | 0.86 | 0.78 | 1.21 |
| (5542-SP30021-10-16 × 5538-LP004-25-2-25) | 4.07 | 0.06 | 1.74 | 36 | 0.06 | 32.18 | 17.86 | 4.32 | 0.96 | 0.73 | 1.27 |
| (5542-SP30021-10-16 × 5538-LP004-25-2-25) | 4.11 | 0.05 | 2.24 | 29.64 | 0.04 | 28.64 | 27.94 | 3.06 | 1.12 | 0.97 | 1.26 |

Example 16

Expression of *M. alpina* Desaturases in Soybean

The *M. alpina* desaturases can be used to drive production of GLA and other PUFAs in soybean by use of the following expression constructs. Two means by which exogenous DNA can be inserted into the soybean genome are *Agrobacterium* infection or particle gun. Particle gun transformation is disclosed in U.S. Pat. No. 5,503,998. Plants can be selected using a glyphosate resistance marker (4, 971, 908). *Agrobacterium* transformation of soybean is well established to one of ordinary skill in the art.

Godette, W. D., Zenger, V., Beachy, R. N., and Slightom. J. L., 1986 J. Biol. Chem. 261 (20), 9228-9238). The 3' regulatory region that can be used is from the pea ribulose 1,5 bisphosphate carboxylase/oxygenase small subunit (rbcS) gene. The specific sequences to be used are nucleotides 1-645 of gi 169145 (Hunt, A. G. 1988 DNA 7: 329-336).

Since soybean seeds contain more 18:2, and perhaps more endogenous Δ12 desaturase activity than *Brassica*, the effect of the *Mortierella* Δ12 desaturase on achieving optimal GLA levels can be tested as follows. A construct containing the Δ6 cDNA can be used to see if $\Delta^{6,9}$ 18:2 is produced along with GLA. A construct containing the Δ12 desaturase can be used to see if the amount of 18:2 can be increased in soybean. A construct containing both the Δ6 and Δ12 desaturases can be used to produce optimal levels of GLA. Alternatively, plants containing each of the single desaturases may be crossed if necessary to combine the genes.

Similar constructs may be made to express the Δ5 desaturase alone, or in combination with Δ12 and/or Δ6 desaturases.

Example 17

Human Desaturase Gene Sequences

Human desaturase gene sequences potentially involved in long chain polyunsaturated fatty acid biosynthesis were isolated based on homology between the human cDNA sequences and *Mortierella alpina* desaturase gene sequences. The three conserved "histidine boxes" known to be conserved among membrane-bound desaturases were found. As with some other membrane-bound desaturases the final HXXHH histidine box motif was found to be QXXHH. The amino acid sequence of the putative human desaturases exhibited homology to *M. alpina* Δ5, Δ6, Δ9, and Δ12 desaturases.

The *M. alpina* Δ5 desaturase and Δ6 desaturase cDNA sequences were used to search the LifeSeq database of Incyte Pharmaceuticals, Inc., Palo Alto, Calif. 94304. The Δ5 desaturase sequence was divided into fragments; 1) amino acid no. 1-150, 2) amino acid no. 151-300, and 3) amino acid no. 301-446. The Δ6 desaturase sequence was divided into three fragments; 1) amino acid no. 1-150, 2) amino acid no. 151-300, and 3) amino acid no. 301-457. These polypeptide fragments were searched against the database using the "tblastn" algorithm. This algorithm compares a protein query sequence against a nucleotide sequence database dynamically translated in all six reading frames (both strands).

The polypeptide fragments 2 and 3 of *M. alpina* Δ5 and Δ6 have homologies with the CloneID sequences as outlined in Table 18. The CloneID represents an individual sequence from the Incyte LifeSeq database. After the "tblastn" results have been reviewed, Clone Information was searched with the default settings of Stringency of >=50, and Productscore <=100 for different CloneID numbers. The Clone Information Results displayed the information including the ClusterID, CloneID, Library, HitID, Hit Description. When selected, the ClusterID number displayed the clone information of all the clones that belong in that ClusterID. The Assemble command assembles all of the CloneID which comprise the ClusterID. The following default settings were used for GCG (Genetics Computer Group, University of Wisconsin Biotechnology Center, Madison, Wis. 53705) Assembly:

| Word Size: | 7 |
|---|---|
| Minimum Overlap: | 14 |
| Stringency: | 0.8 |
| Minimum Identity: | 14 |
| Maximum Gap: | 10 |
| Gap Weight: | 8 |
| Length Weight: | 2 |

GCG Assembly Results displayed the contigs generated on the basis of sequence information within the CloneID. A contig is an alignment of DNA sequences based on areas of homology among these sequences. A new sequence (consensus sequence) was generated based on the aligned DNA sequences within a contig. The contig containing the CloneID was identified, and the ambiguous sites of the consensus sequence was edited based on the alignment of the CloneIDs (see SEQ ID NO:31-SEQ ID NO:35) to generate the best possible sequence. The procedure was repeated for all six CloneID listed in Table 18. This produced five unique contigs. The edited consensus sequences of the 5 contigs were imported into the Sequencher software program (Gene Codes Corporation, Ann Arbor, Mich. 48 105). These consensus sequences were assembled. The contig 2511785 overlaps with contig 3506132, and this new contig was called 2535 (SEQ ID NO:37). The contigs from the Sequencher program were copied into the Sequence Analysis software package of GCG.

Each contig was translated in all six reading frames into protein sequences. The *M. alpina* Δ5 (MA29) and Δ6 (MA524) sequences were compared with each of the translated contigs using the FastA search (a Pearson and Lipman search for similarity between a query sequence and a group of sequences of the same type (nucleic acid or protein)). Homology among these sequences suggest the open reading frames of each contig. The homology among the *M. alpina* Δ5 and Δ6 to contigs 2535 and 3854933 were utilized to create the final contig called 253538a. FIG. 9 is the FastA match of the final contig 253538a and MA29, and FIG. 10 is the FastA match of the final contig 253538a and MA524. The DNA sequences for the various contigs are presented in SEQ ID NO:31-SEQ ID NO:37 The various peptide sequences are shown in SEQ ID NO:38 SEQ ID NO: 44.

Although the open reading frame was generated by merging the two contigs, the contig 2535 shows that there is a unique sequence in the beginning of this contig which does not match with the contig 3854933. Therefore, it is possible that these contigs were generated from independent desaturase like human genes.

The contig 253538a contains an open reading frame encoding 432 amino acids. It starts with Gln (CAG) and ends with the stop codon (TGA). The contig 253538a aligns with both *M. alpina* Δ5 and Δ6 sequences, suggesting that it could be either of the desaturases, as well as other known desaturases which share homology with each other. The individual contigs listed in Table 18, as well as the intermediate contig 2535 and the final contig 253538a can be utilized to isolate the complete genes for human desaturases.

Uses of the Human Desaturases

These human sequences can be expressed in yeast and plants utilizing the procedures described in the preceding examples. For expression in mammalian cells and transgenic animals, these genes may provide superior codon bias. In addition, these sequences can be used to isolate related desaturase genes from other organisms.

TABLE 18

| Sections of the Desaturases | Clone ID from LifeSeq Database | Keyword |
|---|---|---|
| 151-300 Δ5 | 3808675 | fatty acid desaturase |
| 301-446 Δ5 | 354535 | Δ6 |
| 151-300 Δ6 | 3448789 | Δ6 |
| 151-300 Δ6 | 1362863 | Δ6 |
| 151-300 Δ6 | 2394760 | Δ6 |
| 301-457 Δ6 | 3350263 | Δ6 |

Example 18

Identification of Homologues to *M. alpina* Δ5 and Δ6 Desaturases

A nucleic acid sequence that encodes a putative Δ5 desaturase was identified through a TBLASTN search of the expressed sequence tag databases through NCBI using amino acids 100-446 of Ma29 as a query. The truncated portion of the Ma29 sequence was used to avoid picking up homologies based on the cytochrome b5 portion at the N-terminus of the desaturase. The deduced amino acid sequence of an est from *Dictyostelium discoideum* (accession # C25549) shows very significant homology to Ma29 and lesser, but still significant homology to Ma524. The DNA sequence is presented as SEQ ID NO:45. The amino acid sequence is presented as SEQ ID NO:46.

Example 19

Identification of *M. alpina* Δ5 and Δ6 Homologues in Other PUFA-Producing Organisms To look for desaturases involved in PUFA production, a cDNA library was constructed from total RNA isolated from *Phaeodactylum tricornutum*. A plasmid-based cDNA library was constructed in pSPORT1 (GIBCO-BRL) following manufacturer's instructions using a commercially available kit (GIBCO-BRL). Random cDNA clones were sequenced and nucleic acid sequences that encode putative Δ5 or Δ6 desaturases were identified through BLAST search of the databases and comparison to Ma29 and Ma524 sequences.

One clone was identified from the *Phaeodactylum* library with homology to Ma29 and Ma524; it is called 144-011-B12. The DNA sequence is presented as SEQ ID NO:47. The amino acid sequence is presented as SEQ ID NO:48.

Example 20

Identification of *M. alpina* Δ5 and Δ6 Homologues in Other PUFA-Producing Organisms To look for desaturases involved in PUFA production, a cDNA library was constructed from total RNA isolated from *Schizochytrium* species. A plasmid-based cDNA library was constructed in pSPORT1 (GIBCO-BRL) following manufacturer's instructions using a commercially available kit (GIBCO-BRL). Random cDNA clones were sequenced and nucleic acid sequences that encode putative Δ5 or Δ6 desaturases were identified through BLAST search of the databases and comparison to Ma29 and Ma524 sequences.

One clone was identified from the *Schizochytrium* library with homology to Ma29 and Ma524; it is called 81-23-C7. This clone contains a ~1 kb insert. Partial sequence was obtained from each end of the clone using the universal forward and reverse sequencing primers. The DNA sequence from the forward primer is presented as SEQ ID NO:49. The peptide sequence is presented as SEQ ID NO:50. The DNA sequence from the reverse primer is presented as SEQ ID NO:51. The amino acid sequence from the reverse primer is presented as SEQ ID NO:52.

Example 21

Nutritional Compositions

The PUFAs of the previous examples can be utilized in various nutritional supplements, infant formulations, nutritional substitutes and other nutrition solutions.

I. Infant Formulations

A. ISOMIL® Soy Formula with Iron.

Usage: As a beverage for infants, children and adults with an allergy or sensitivity to cow's milk. A feeding for patients with disorders for which lactose should be avoided: lactase deficiency, lactose intolerance and galactosemia.

Features:
Soy protein isolate to avoid symptoms of cow's-milk-protein allergy or sensitivity
Lactose-free formulation to avoid lactose-associated diarrhea
Low osmolaity (240 mOsm/kg water) to reduce risk of osmotic diarrhea.
Dual carbohydrates (corn syrup and sucrose) designed to enhance carbohydrate absorption and reduce the risk of exceeding the absorptive capacity of the damaged gut.
1.8 mg of Iron (as ferrous sulfate) per 100 Calories to help prevent iron deficiency.
Recommended levels of vitamins and minerals.
Vegetable oils to provide recommended levels of essential fatty acids.
Milk-white color, milk-like consistency and pleasant aroma.
Ingredients: (Pareve, ®) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

B. ISOMIL® DF Soy Formula for Diarrhea.

Usage: As a short-term feeding for the dietary management of diarrhea in infants and toddlers.

Features:
First infant formula to contain added dietary fiber from soy fiber specifically for diarrhea management.
Clinically shown to reduce the duration of loose, watery stools during mild to severe diarrhea in infants.
Nutritionally complete to meet the nutritional needs of the infant.
Soy protein isolate with added L-methionine meets or exceeds an infant's requirement for all essential amino acids.
Lactose-free formulation to avoid lactose-associated diarrhea.
Low osmolality (240 mOsm/kg water) to reduce the risk of osmotic diarrhea.
Dual carbohydrates (corn syrup and sucrose) designed to enhance carbohydrate absorption and reduce the risk of exceeding the absorptive capacity of the damaged gut.
Meets or exceeds the vitamin and mineral levels recommended by the Committee on Nutrition of the American Academy of Pediatrics and required by the Infant Formula Act.
1.8 mg of iron (as ferrous sulfate) per 100 Calories to help prevent iron deficiency.
Vegetable oils to provide recommended levels of essential fatty acids.
Ingredients: (Pareve, ®) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono- and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

C. ISOMIL® SF Sucrose-Free Soy Formula with Iron.

Usage: As a beverage for infants, children and adults with an allergy or sensitivity to cow's-milk protein or an intolerance to sucrose. A feeding for patients with disorders for which lactose and sucrose should be avoided.

Features:

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve, ®) 75% water, 11.8% hydrolyzed cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

D. ISOMIL® 20 Soy Formula with Iron Ready to Feed, 20 Cal/fl oz.

Usage: When a soy feeding is desired.

Ingredients: (Pareve, ®) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin $D_3$ and cyanocobalamin.

E. SIMILAC® Infant Formula

Usage: When an infant formula is needed: if the decision is made to discontinue breastfeeding before age 1 year, if a supplement to breastfeeding is needed or as a routine feeding if breastfeeding is not adopted.

Features:

Protein of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (®-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamid, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin $D_3$ and cyanocobalamin.

F. SIMILAC NEOCARE® Premature Infant Formula with Iron

Usage: For premature infants' special nutritional needs after hospital discharge. SIMILAC NEOCARE® infant formula is a nutritionally complete formula developed to provide premature infants with extra calories, protein, vitamins and minerals needed to promote catch-up growth and support development.

Features:

Reduces the need for caloric and vitamin supplementation. More calories (22 Cal/fl oz) then standard term formulas (20 Cal/fl oz).

Highly absorbed fat blend, with medium-chain triglycerides (MCT oil) to help meet the special digestive needs of premature infants.

Higher levels of protein, vitamins and minerals per 100 Calories to extend the nutritional support initiated in-hospital.

More calcium and phosphorus for improved bone mineralization.

Ingredients: ®-D Corn syrup solids, nonfat milk, lactose, whey protein concentrate, soy oil, high-oleic safflower oil, fractionated coconut oil (medium-chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin $D_3$ and cyanocobalamin.

G. SIMILAC NATURAL CARE® Low-Iron Human Milk Fortifier Ready to Use, 24 Cal/fl oz.

Usage: Designed to be mixed with human milk or to be fed alternatively with human milk to low-birth-weight infants.

Ingredients: ®-D Water, nonfat milk, hydrolyzed cornstarch, lactose, fractionated coconut oil (medium-chain triglycerides), whey protein concentrate, soil oil, coconut oil, calcium phosphate tribasic, potassium citrate, magnesium chloride, sodium citrate, ascorbic acid, calcium carbonate, mono- and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin $D_3$, sodium selenite and cyanocobalamin.

Various PUFAs of this invention can be substituted and/or added to the infant formulae described above and to other infant formulae known to those in the art.

II. Nutritional Formulations

A. ENSURE® Food Supplement

Usage: ENSURE® food supplement is a low-residue liquid food designed primarily as an oral nutritional supplement to be used with or between meals or, in appropriate amounts, as a meal replacement. ENSURE® food supplement is lactose- and gluten-free, and is suitable for use in modified diets, including low-cholesterol diets. Although it is primarily an oral supplement, it can be fed by tube.

Patient Conditions:
  For patients on modified diets
  For elderly patients at nutrition risk
  For patients with involuntary weight loss
  For patients recovering from illness or surgery
  For patients who need a low-residue diet Ingredients:
  ⓧ-D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. Ensure® Bars

Usage: ENSURE® BARS are complete, balanced nutrition for supplemental use between or with meals. They provide a delicious, nutrient-rich alternative to other snacks. ENSURE® BARS contain <1 g lactose/bar, and Chocolate Fudge Brownie flavor is gluten-free. (Honey Graham Crunch flavor contains gluten.)

Patient Conditions:
  For patients who need extra calories, protein, vitamins and minerals
  Especially useful for people who do not take in enough calories and nutrients
  For people who have the ability to chew and swallow
  Not to be used by anyone with a peanut allergy or any type of allergy to nuts.

Ingredients:
  Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flafors, Canola Oil, High-Oleic Safflower Oil, Nonfat Dry Milk, Whey Powder, Soy Lecithin and Corn Oil. Manufactured in a facility that processes nuts.

Vitamins and Minerals:
  Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta-Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin $D_3$ and Cyanocobalamin.

Protein:

Honey Graham Crunch—The protein source is a blend of soy protein isolate and milk proteins.

| Soy protein isolate | 74% |
| Milk proteins | 26% |

Fat:

Honey Graham Crunch—The fat source is a blend of partially hydrogenated cottonseed and soybean, canola, high oleic safflower, and corn oils, and soy lecithin.

| Partially hydrogenated cottonseed and soybean oil | 76% |
| Canola oil | 8% |
| High-oleic safflower oil | 8% |
| Corn oil | 4% |
| Soy lecithin | 4% |

Carbohydrate:

Honey Graham Crunch—The carbohydrate source is a combination of high-fructose corn syrup, brown sugar, maltodextrin, honey, crisp rice, glycerine, soy polysaccharide, and oat bran.

| High-fructose corn syrup | 24% |
| Brown sugar | 21% |
| Maltodextrin | 12% |
| Honey | 11% |
| Crisp rice | 9% |
| Glycerine | 9% |
| Soy polysaccharide | 7% |
| Oat bran | 7% |

C. Ensure® High Protein

Usage: ENSURE® HIGH PROTEIN is a concentrate, high-protein liquid food designed for people who require additional calories, protein, vitamins, and minerals in their diets. It can be used as an oral nutritional supplement with or between meals or, in appropriate amounts, as a meal replacement. ENSURE® HIGH PROTEIN is lactose- and gluten-free, and is suitable for use by people recovering from general surgery or hip fractures and by patients at risk for pressure ulcers.

Patient Conditions
  For patients who require additional calories, protein, vitamins, and minerals, such as patients recovering from general surgery or hip fractures, patients at risk for pressure ulcers, and patients on low-cholesterol diets Features—
  Low in saturated fat
  Contains 6 g of total fat and <5 mg of cholesterol per serving
  Rich, creamy taste
  Excellent source of protein, calcium, and other essential vitamins and minerals
  For low-cholesterol diets
  Lactose-free, easily digested Ingredients:

Vanilla Supreme: -®-D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folio Acid, Sodium Motybdate, Chromium Chloride, Biotin, Potassium Iodide, Sodium Selenate, Phylloquinone, Vitamin D.3 and Cyanocobalarnin.

Protein:

The protein source is a blend of two high-biologic-value proteins: casein and soy.

| | |
|---|---|
| Sodium and calcium caseinates | 85% |
| Soy protein isolate | 15% |

Fat:

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE® HIGH PROTEIN meets American Heart Association (AHA) guidelines. The 6 grams of fat in ENSURE® HIGH PROTEIN represent 24% of the total calories, with 2.6% of the fat being from saturated fatty acids and 7.9% from poly unsaturated fatty acids. These values are within the AHA guidelines of $\leq 30\%$ of total calories from fat, $\leq 10\%$ of the calories from saturated fatty acids and $\leq 10\%$ of total calories from polyunsaturated fatty acids.

Carbohydrate:

ENSURE® HIGH PROTEIN contains a combination of maltodextrin and sucrose. The mild sweetness and flavor variety (vanilla supreme, chocolate royal, wild berry, and banana), plus VARI-FLAVORS® Flavor Pacs food flavors in pecan, cherry, strawberry, lemon, and orange, help to prevent flavor fatigue and aid in patient compliance.

Vanilla and Other Nonchocolate Flavors

| | |
|---|---|
| Sucrose | 60% |
| Maltodextrin | 40% |

Chocolate

| | |
|---|---|
| Sucrose | 70% |
| Maltodextrin | 30% |

D. ENSURE® LIGHT

Usage: ENSURE® LIGHT is a low-fat liquid food designed for use as an oral nutritional supplement with or between meals. ENSURE® LIGHT is lactose- and gluten-free, and is suitable for use in modified diets, including low-cholesterol diets.

Patient Conditions:

For normal-weight or overweight patients who need extra nutrition in a supplement that contains 50% less fat and 20% fewer calories than ENSURE For healthy adults who don't eat right and need extra nutrition Features:

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients:

French Vanilla: ®-D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin $D_3$ and Cyanocobalamin.

Protein:

The protein source is calcium caseinate.

| | |
|---|---|
| Calcium caseinate | 100% |

Fat

The fat source is a blend of two oils: high-oleic safflower and canola.

| | |
|---|---|
| High-oleic safflower oil | 70% |
| Canola oil | 30% |

The level of fat in ENSURE® LIGHT meets American Heart Association (AHA) guidelines. The 3 grams of fat in ENSURE® LIGHT represent 13.5% of the total calories, with 1.4% of the fat being from saturated fatty acids and 2.6% from polyunsaturated fatty acids. These values are within the AHA guidelines of $\leq 30\%$ of total calories from fat, $\leq 10\%$ of the calories from saturated fatty acids and $\leq 10\%$ of total calories from polyunsaturated fatty acids.

Carbohydrate

ENSURE® LIGHT contains a combination of maltodextrin and sucrose. The chocolate flavor contains corn syrup as well. The mild sweetness and flavor variety (French vanilla, chocolate supreme, strawberry swirl), plus VARI-FLA-VORS® Flavor Pacs food flavors in pecan, cherry, strawberry, lemon, and orange, help to prevent flavor fatigue and aid in patient compliance.

Vanilla and Other Nonchocolate Flavors

| | |
|---|---|
| Sucrose | 51% |
| Maltodextrin | 49% |

Chocolate

| | |
|---|---|
| Sucrose | 47.0% |
| Corn Syrup | 26.5% |
| Maltodextrin | 26.5% |

Vitamins and Minerals

An 8-fl-oz serving of ENSURE® LIGHT provides at least 25% of the RDIs for 24 key vitamins and minerals.

Caffeine

Chocolate flavor contains 2.1 mg caffeine/8 fl oz.

E. ENSURE PLUS® Liquid Nutritive Preparation

Usage: ENSURE PLUS® liquid nutritive preparation is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS® liquid nutritive preparation is lactose- and gluten-free. Although it is primarily an oral nutritional supplement, it can be fed by tube.

Patient Conditions:

For patients who require extra calories and nutrients, but a normal concentration of protein, in a limited volume For patients who need to gain or maintain healthy weight Features Rich, creamy taste Good source of essential vitamins and minerals Ingredients Vanilla: ®-D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin $D_3$.

Protein

The protein source is a blend of two high-biologic-value proteins: casein and soy.

| | |
|---|---|
| Sodium and calcium caseinates | 84% |
| Soy protein isolate | 16% |

Fat

| | |
|---|---|
| The fat source is corn oil. | |
| Corn oil | 100% |

Carbohydrate

ENSURE PLUS® liquid nutritive preparation contains a combination of maltodextrin and sucrose. The mild sweetness and flavor variety (vanilla, chocolate, strawberry, coffee, butter pecan, and eggnog), plus VARI-FLAVORS® Flavor Pacs food flavors in pecan, cherry, strawberry, lemon, and orange, help to prevent flavor fatigue and aid in patient compliance.

Vanilla, Strawberry, Butter Pecan, and Coffee Flavors

| | |
|---|---|
| Corn Syrup | 39% |
| Maltodextrin | 38% |
| Sucrose | 23% |

Chocolate and Eggnog Flavors

| | |
|---|---|
| Corn Syrup | 36% |
| Maltodextrin | 34% |
| Sucrose | 30% |

Vitamins and Minerals

An 8-fl-oz serving of ENSURE PLUS® liquid nutritive preparation provides at least 15% of the RDIs for 25 key Vitamins and minerals.

Caffeine

Chocolate flavor contains 3.1 mg Caffeine/8 fl oz. Coffee flavor contains a trace amount of caffeine.

F. ENSURE PLUS® HN Liquid Nutritive Preparation

Usage: ENSURE PLUS® HN liquid nutritive preparation is a nutritionally complete high-calorie, high-nitrogen liquid food designed for people with higher calorie and protein needs or limited volume tolerance. It may be used for oral supplementation or for total nutritional support by tube. ENSURE PLUS® HN liquid nutritive preparation is lactose- and gluten-free.

Patient Conditions:

For patients with increased calorie and protein needs, such as following surgery or injury For patients with limited volume tolerance and early satiety Features For supplemental or total nutrition For oral or tube feeding 1.5 CaVmL High nitrogen Calorically dense Ingredients Vanilla: ®-D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin $D_3$.

G. ENSURE® POWDER

Usage: ENSURE® POWDER (reconstituted with water) is a low-residue liquid food designed primarily as an oral nutritional supplement to be used with or between meals. ENSURE® POWDER is lactose- and gluten-free, and is suitable for use in modified diets, including low-cholesterol diets.

Patient Conditions:
    For patients on modified diets
    For elderly patients at nutrition risk
    For patients recovering from illness/surgery
    For patients who need a low-residue diet Features
    Convenient, easy to mix
    Low in saturated fat
    Contains 9 g of total fat and <5 mg of cholesterol per serving
    High in vitamins and minerals
    For low-cholesterol diets
    Lactose-free, easily digested Ingredients: ®-D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin $D_3$ and Cyanocobalamin.

Protein

The protein source is a blend of two high-biologic-value proteins: casein and soy.

| | |
|---|---|
| Sodium and calcium caseinates | 84% |
| Soy protein isolate | 16% |

Fat

| | |
|---|---|
| Corn oil | 100% |

Carbohydrate

ENSURE® POWDER contains a combination of corn syrup, maltodextrin, and sucrose. The mild sweetness of ENSURE® POWDER, plus VARI-FLAVORS® Flavor Pacs food flavors in pecan, cherry, strawberry, lemon, and orange, helps to prevent flavor fatigue and aid in patient compliance.

Vanilla

| | |
|---|---|
| Corn Syrup | 35% |
| Maltodextrin | 35% |
| Sucrose | 30% |

H. ENSURE® PUDDING

Usage: ENSURE® PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE® PUDDING is gluten-free.

Patient Conditions:
    For patients on consistency-modified diets (e.g., soft, pureed, or full liquid)
    For patients with swallowing impairments Features
    Rich and creamy, good taste
    Good source of essential vitamins and minerals Convenient-needs no refrigeration
    Gluten-free Nutrient Profile per 5 oz: Calories 250, Protein 10.9%, Total Fat 34.9%, Carbohydrate 54.2%

Ingredients:

Vanilla: ®-D Nonfat Milk, Water, Sugar (Sucrose), Partially Hydrogenated Soybean Oil, Modified Food Starch, Magnesium Sulfate. Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein

| | |
|---|---|
| Nonfat milk | 100% |

Fat

| | |
|---|---|
| Hydrogenated soybean oil | 100% |

Carbohydrate

ENSURE® PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and Other Nonchocolate Flavors

| | |
|---|---|
| Sucrose | 56% |
| Lactose | 27% |
| Modified food starch | 17% |

Chocolate

| | |
|---|---|
| Sucrose | 58% |
| Lactose | 26% |
| Modified food starch | 16% |

Usage: ENSURE® WITH FIBER is a fiber-containing, nutritionally complete liquid food designed for people who can benefit from increased dietary fiber and nutrients. ENSURE® WITH FIBER is suitable for people who do not require a low-residue diet. It can be fed orally or by tube, and can be used as a nutritional supplement to a regular diet or, in appropriate amounts, as a meal replacement. ENSURE® WITH FIBER is lactose- and gluten-free, and is suitable for use in modified diets, including low-cholesterol diets.

Patient Conditions

For patients who can benefit from increased dietary fiber and nutrients

Features

New advanced formula-low in saturated fat, higher in vitamins and minerals

Contains 6 g of total fat and <5 mg of cholesterol per serving

Rich, creamy taste

Good source of fiber

Excellent source of essential vitamins and minerals

For low-cholesterol diets

Lactose- and gluten-free

Ingredients

Vanilla: ⓐ-D Water, Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin $D_3$ and Cyanocobalamin.

Protein

The protein source is a blend of two high-biologic-value proteins-casein and soy.

| Sodium and calcium caseinates | 80% |
|---|---|
| Soy protein isolate | 20% |

Fat

The fat source is a blend of three oils: high-oleic safflower, canola, and corn.

| High-oleic safflower oil | 40% |
|---|---|
| Canola oil | 40% |
| Corn oil | 20% |

The level of fat in ENSURE® WITH FIBER meets American Heart Association (AHA) guidelines. The 6 grams of fat in ENSURE® WITH FIBER represent 22% of the total calories, with 2.01% of the fat being from saturated fatty acids and 6.7% from polyunsaturated fatty acids. These values are within the AHA guidelines of ≦30% of total calories from fat, ≦10% of the calories from saturated fatty acids and ≦10% of total calories from polyunsaturated fatty acids.

Carbohydrate

ENSURE® WITH FIBER contains a combination of maltodextrin and sucrose. The mild sweetness and flavor variety (vanilla, chocolate, and butter pecan), plus VARI-FLA-VORS® Flavor Pacs food flavors in pecan, cherry, strawberry, lemon, and orange, help to prevent flavor fatigue and aid in patient compliance.

Vanilla and Other Nonchocolate Flavors

| Maltodextrin | 66% |
|---|---|
| Sucrose | 25% |
| Oat Fiber | 7% |
| Soy Fiber | 2% |

Chocolate

| Maltodextrin | 55% |
|---|---|
| Sucrose | 36% |
| Oat Fiber | 7% |
| Soy Fiber | 2% |

Fiber

The fiber blend used in ENSURE® WITH FIBER consists of oat fiber and soy polysaccharide. This blend results in approximately 4 grams of total dietary fiber per 8-fl-oz can. The ratio of insoluble to soluble fiber is 95:5.

The various nutritional supplements described above and known to others of skill in the art can be substituted and/or supplemented with the PUFAs of this invention.

J. OXEPA® Nutritional Product

OXEPA® is a low-carbohydrate, calorically dense enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs.

The distribution of Calories in OXEPA® nutritional product is shown in Table 7.

TABLE 7

Caloric Distribution of OXEPA ® Nutritional Product

|  | per 8 fl oz. | per liter | % of Cal |
|---|---|---|---|
| Calories | 355 | 1,500 | — |
| Fat(g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

OXEPA® nutritional product contains 22.2 g of fat per 8-fl oz serving (93.7 g/L).

The fat source is a oil blend of 31.8% canola oil, 25% medium-chain triglycerides (MCTs), 20% borage oil, 20% fish oil, and 3.2% soy lecithin. The typical fatty acid profile of OXEPA® nutritional product is shown in Table 8.

OXEPA® nutritional product provides a balanced amount of polyunsaturated, monounsaturated, and saturated fatty acids, as shown in Table 10.

Medium-chain triglycerides (MCTs)—25% of the fat blend—aid gastric emptying because they are absorbed by the intestinal tract without emulsification by bile acids.

The various fatty acid components of OXEPA® nutritional product can be substituted and/or supplemented with the PUFAs of this invention.

TABLE 8

Typical Fatty Acid Profile

|  | % Total Fatty Acids | g/8 fl oz* | g/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic (16:1n-7) | 1.82 | 0.38 | 1.62 |
| Stearic (18:0) | 1.84 | 0.39 | 1.64 |
| Oleic (18:1n-9) | 24.44 | 5.16 | 21.75 |
| Linoleic (18:2n-6) | 16.28 | 3.44 | 14.49 |
| α-Linolenic (18:3n-3) | 3.47 | 0.73 | 3.09 |
| γ-Linolenic (18:3n-6) | 4.82 | 1.02 | 4.29 |
| Eicosapentaenoic (20:5n-3) | 5.11 | 1.08 | 4.55 |
| n-3-Docosapentaenoic (22:5n-3) | 0.55 | 0.12 | 0.49 |
| Docosahexaenoic (22:6n-3) | 2.27 | 0.48 | 2.02 |
| Others | 7.55 | 1.52 | 6.72 |

*Fatty acids equal approximately 95% of total fat.

TABLE 9

Fat Profile of OXEPA ® Nutritional Product

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz |
|  | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of OXEPA® nutritional product is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

OXEPA® nutritional product is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in OXEPA® nutritional product is also sufficient to minimize gluconeogenesis, if energy needs are being met.

Protein:

OXEPA® nutritional product contains 14.8 g of protein per 8-fl-oz serving (62.5 g/L).

The total calorie/nitrogen ratio (150:1) meets the need of stressed patients.

OXEPA® nutritional product provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of OXEPA® nutritional product are 86.8% sodium caseinate an 13.2% calcium caseinate.

As demonstrated in Table 11, the amino acid profile of the protein system in OXEPA® nutritional product meets or surpasses the standard for high quality protein set by the National Academy of Sciences.

OXEPA® nutritional product is gluten-free.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for producing a plant comprising a tissue and/or part thereof with an altered fatty acid profile comprising:
   growing a plant comprising a tissue and/or part thereof comprising a plurality of cells, each of said plurality comprising a nucleic acid comprising the sequence depicted in SEQ ID NO:1, said nucleic acid operably linked to transcription and translation control signals functional in said cells, wherein a polypeptide encoded by said nucleic acid is expressed in sufficient amount in said tissue and/or part to alter the fatty acid profile thereof.

2. The method of claim 1, wherein said tissue and/or part is a seed of said plant.

3. The method of claim 1, wherein said tissue and/or part is a leaf of said plant.

4. The method of claim 1, wherein said tissue and/or part is a fruit of said plant.

5. The method of claim 1, wherein said tissue and/or part is a flower of said plant.

6. The method of claim 1, wherein said tissue and/or part is a root of said plant.

7. The method of claim 1, wherein at least one of said transcription and translation control signals is endogenous to said plant.

8. A method for producing a plant comprising a tissue and/or part thereof with an altered fatty acid profile comprising:
   growing a plant comprising a tissue and/or part thereof comprising a plurality of cells, each of said plurality comprising a nucleic acid with at least 95% homology to the sequence depicted in SEQ ID NO:1, said nucleic acid operably linked to transcription and translation control signals function in said cells, wherein a polypeptide encoded by said nucleic acid forms a monounsaturated bond between carbons 6 and 7 of a fatty acid as numbered from a carboxy terminus thereof, wherein said polypeptide is expressed in sufficient amount in said tissue and/or part to alter the fatty acid profile thereof.

9. The method of claim 8, wherein said tissue and/or part is a seed of said plant.

10. The method of claim 8, wherein said tissue and/or part is a leaf of said plant.

11. The method of claim 8, wherein said tissue and/or part is a fruit of said plant.

12. The method of claim 8, wherein said tissue and/or part is a flower of said plant.

13. The method of claim 8, wherein said tissue and/or part is a root of said plant.

14. The method of claim 8, wherein at least one of said transcription and translation control signals is endogenous to said plant.

15. A method for producing a plant comprising a tissue and/or part thereof with an altered fatty acid profile comprising:
   growing a plant comprising a tissue and/or plant thereof comprising a plurality of cells, each of said plurality comprising a nucleic acid operably linked to transcription and translation control signals functional in said cells, wherein said nucleic acid encodes a deletion mutant of the polypeptide depicted in SEQ ID NO:2, wherein a polypeptide encoded by said nucleic acid forms a monounsaturated bond between carbons 6 and 7 of a fatty acid as numbered from a carboxy terminus thereof, wherein said polypeptide is expressed in sufficient amount in said tissue and/or part to alter the fatty acid profile thereof.

16. A method for producing a plant comprising a tissue and/or part thereof with an altered fatty acid profile comprising:
growing a plant comprising a tissue and/or part thereof comprising a plurality of cells, each of said plurality comprising a polypeptide comprising the amino acid sequence depicted in SEQ ID NO:2, wherein said polypeptide is expressed in sufficient amount in said tissue and/or part to alter the fatty acid profile thereof.

17. The method of claim 16, wherein said tissue and/or part is a seed of said plant.

18. The method of claim 16, wherein said tissue and/or part is a leaf of said plant.

19. The method of claim 16, wherein said tissue and/or part is a fruit of said plant.

20. The method of claim 16, wherein said tissue and/or part is a flower of said plant.

21. The method of claim 16, wherein said tissue and/or part is a root of said plant.

22. A method for producing a plant comprising a tissue and/or part thereof with an altered fatty acid profile comprising:
growing a plant comprising a tissue and/or part thereof comprising a plurality of cells, each of said plurality comprising a polypeptide with at least 95% homology to the sequence depicted in SEQ ID NO:2, wherein said polypeptide forms a monounsaturated bond between carbons 6 and 7 of a fatty acid as numbered from a carboxy terminus thereof, wherein said polypeptide is expressed in sufficient amount in said tissue and/or part to alter the fatty acid profile thereof.

23. A method for producing a plant comprising a tissue and/or part thereof with an altered fatty acid profile comprising:
growing a plant comprising a tissue and/or part thereof comprising a plurality of cells, each of said plurality comprising a nucleic acid that hybridizes preferentially to a complement of the sequence depicted in SEQ ID NO:1 under hybridization conditions suitable for selectively screening a recombinant DNA library using a probe comprising said complement, said recombinant DNA library comprising sequences obtained from a *Mortierella* species, said nucleic acid operably linked to transcription and translation control signals functional in said cells, wherein a polypeptide encoded by said nucleic acid forms a monounsaturated bond between carbons 6 and 7 of a fatty acid as numbered from a carboxy terminus thereof, wherein said polypeptide is expressed in sufficient amount in said tissue and/or part to alter the fatty acid profile thereof.

24. A method for producing oil with an altered fatty acid profile comprising extracting said oil with an altered fatty acid profile from at least a plant tissue and/or part produced by growing a plant comprising the tissue and/or part, said tissue and/or part comprising a plurality of cells, each of said plurality comprising a nucleic acid comprising the sequence depicted in SEQ ID NO:1, said nucleic acid operably linked to transcription and translation control signals functional in said cells, wherein a polypeptide encoded by said nucleic acid is expressed in sufficient amount in said tissue and/or part to alter the fatty acid profile of said oil, wherein the fatty acid profile is altered as compared to that of oil extracted from a parental strain of said plant not expressing said polypeptide.

25. The method of claim 24, further comprising purifying a component of said oil.

26. The method of claim 25, wherein said component is a phospholipid.

27. The method of claim 25, wherein said component is a sulfolipid.

28. The method of claim 25, wherein said component is a glycolipid.

29. The method of claim 25, wherein said component is a acylglycerol.

30. The method of claim 29, wherein said component is a monoacylglycerol.

31. The method of claim 29, wherein said component is a diacylglycerol.

32. The method of claim 29, wherein said component is a triacylglycerol.

33. A method for producing oil with an altered fatty acid profile comprising extracting said oil from at least a plant tissue and/or part produced by growing a plant comprising the tissue and/or part, said tissue and/or part comprising a plurality of cells, each of said plurality comprising a nucleic acid with at least 95% homology to the sequence depicted in SEQ ID NO:1, said nucleic acid operably linked to transcription and translation control signals function in said cells, wherein a polypeptide encoded by said nucleic acid forms a monounsaturated bond between carbons 6 and 7 of a fatty acid as numbered from a carboxy terminus thereof, wherein said polypeptide is expressed in sufficient amount in said tissue and/or part to alter the fatty acid profile of said oil, wherein the fatty acid profile is altered as compared to that of oil extracted from a parental strain of said plant not expressing said polypeptide.

34. A method for producing oil with an altered fatty acid profile comprising extracting said oil with an altered fatty acid profile from at least a plant tissue and/or part produced by growing a plant comprising the tissue and/or part, said tissue and/or part comprising a plurality of cells, each of said plurality comprising a polypeptide comprising the amino acid sequence depicted in SEQ ID NO:2, wherein said polypeptide is expressed in sufficient amount in said tissue and/or part to alter the fatty acid profile of said oil, wherein the fatty acid profile is altered as compared to that of oil extracted from a parental strain of said plant not expressing said polypeptide.

35. A method for producing oil with an altered fatty acid profile comprising extracting said oil with an altered fatty acid profile from at least a plant tissue and/or part produced by growing a plant comprising the tissue and/or part, said tissue and/or part comprising a plurality of cells, each of said plurality comprising a polypeptide with at least 95% homology to the sequence depicted in SEQ ID NO:2, said polypeptide forms a monounsaturated bond between carbons 6 and 7 of a fatty acid as numbered from a carboxy terminus thereof, wherein said polypeptide is expressed in sufficient amount in said tissue and/or part to alter the fatty acid profile of said oil, wherein the fatty acid profile is altered as compared to that of oil extracted from a parental strain of said plant not expressing said polypeptide.

36. A plant comprising a tissue and/or part thereof comprising a plurality of cells, each of said plurality comprising a nucleic acid comprising the sequence depicted in SEQ ID NO:1, said nucleic acid operably linked to transcription and translation control signals functional in said cells, wherein a polypeptide encoded by said nucleic acid is expressed in sufficient amount in said tissue and/or part to alter the fatty acid profile of said oil, wherein the fatty acid profile is altered as compared to that of oil extracted from a parental strain of said plant not expressing said polypeptide.

37. A seed isolated from the plant of claim 36.
38. A leaf isolated from the plant of claim 36.
39. A fruit isolated from the plant of claim 36.
40. A flower isolated from the plant of claim 36.
41. A root isolated from the plant of claim 36.
42. A plant comprising a tissue and/or part thereof comprising a plurality of cells, each of said plurality comprising a nucleic acid with at least 95% homology to the sequence depicted in SEQ ID NO:1, said nucleic acid operably linked to transcription and translation control signals functional in said tissue and/or part, wherein a polypeptide encoded by said nucleic acid forms a monounsaturated bond between carbons 6 and 7 of a fatty acid as numbered from a carboxy terminus thereof, wherein said polypeptide is expressed in sufficient amount in said tissue and/or part to alter the fatty acid profile of an oil of said tissue and/or part, wherein the fatty acid profile is altered as compared to that of oil extracted from a parental strain of said plant not expressing said polypeptide.
43. A seed isolated from the plant of claim 42.
44. A leaf isolated from the plant of claim 42.
45. A fruit isolated from the plant of claim 42.
46. A flower isolated from the plant of claim 42.
47. A root isolated from the plant of claim 42.
48. A plant comprising a tissue and/or part thereof comprising a plurality of cells, each of said plurality comprising a polypeptide comprising the amino acid sequence depicted in SEQ ID NO:2, wherein said polypeptide is expressed in sufficient amount in said tissue and/or part to alter the fatty acid profile of said oil, wherein the fatty acid profile is altered as compared to that of oil extracted from a parental strain of said plant not expressing said polypeptide.
49. A seed isolated from the plant of claim 48.
50. A leaf isolated from the plant of claim 48.
51. A fruit isolated from the plant of claim 48.
52. A flower isolated from the plant of claim 48.
53. A root isolated from the plant of claim 48.
54. A plant comprising a tissue and/or part thereof comprising a plurality of cells, each of said plurality comprising a polypeptide with at least 95% homology to the sequence depicted in SEQ ID NO:2, wherein said polypeptide forms a monounsaturated bond between carbons 6 and 7 of a fatty acid as numbered from a carboxy terminus thereof, wherein said polypeptide is expressed in sufficient amount in said tissue and/or part to alter the fatty acid profile of an oil of said tissue and/or part, wherein the fatty acid profile is altered as compared to that of oil extracted from a parental strain of said plant not expressing said polypeptide.
55. A seed isolated from the plant of claim 54.
56. A leaf isolated from the plant of claim 54.
57. A fruit isolated from the plant of claim 54.
58. A flower isolated from the plant of claim 54.
59. A root isolated from the plant of claim 54.
60. A method for producing oil with an increased amount of a polyunsaturated fatty acid and/or a conjugated form thereof, comprising extracting said oil from at least a plant tissue and/or part produced by growing a plant comprising the tissue and/or part, said tissue and/or part comprising a plurality of cells, each of said plurality comprising a nucleic acid comprising the sequence depicted in SEQ ID NO:1, said nucleic acid operably linked to transcription and translation control signals functional in said cells, wherein a polypeptide encoded by said nucleic acid is expressed in said tissue and/or part and is used to produce said increased amount of the polyunsaturated fatty acid and/or conjugated form of said oil, wherein the fatty acid profile is altered as compared to that of oil extracted from a parental strain of said plant not expressing said polypeptide.
61. A method for producing oil with an increased amount of a polyunsaturated fatty acid and/or a conjugated form thereof, comprising extracting said oil from at least a plant tissue and/or part produced by growing the plant of claim 54.

* * * * *